United States Patent
Zimring

(10) Patent No.: US 11,085,937 B2
(45) Date of Patent: Aug. 10, 2021

(54) COMPOSITION AND METHODS FOR ASSESSING SENSITIVITY AND SPECIFICITY OF ANTIBODY DETECTION REAGENTS

(71) Applicant: Bloodworks, Seattle, WA (US)

(72) Inventor: James Charles Zimring, Seattle, WA (US)

(73) Assignee: Bloodworks, Seattle, WA (US)

( * ) Notice: Subject to any disclaimer, the term of this patent is extended or adjusted under 35 U.S.C. 154(b) by 399 days.

(21) Appl. No.: 15/762,532

(22) PCT Filed: Sep. 23, 2016

(86) PCT No.: PCT/US2016/053311
§ 371 (c)(1),
(2) Date: Mar. 22, 2018

(87) PCT Pub. No.: WO2017/053703
PCT Pub. Date: Mar. 30, 2017

(65) Prior Publication Data
US 2019/0049471 A1 Feb. 14, 2019
US 2020/0191805 A9 Jun. 18, 2020

Related U.S. Application Data

(60) Provisional application No. 62/368,069, filed on Jul. 28, 2016, provisional application No. 62/232,310, filed on Sep. 24, 2015.

(51) Int. Cl.
*G01N 33/80* (2006.01)
*G01N 33/68* (2006.01)
*G01N 33/53* (2006.01)
*C07K 16/28* (2006.01)

(52) U.S. Cl.
CPC ......... *G01N 33/80* (2013.01); *C07K 16/2896* (2013.01); *G01N 33/53* (2013.01); *G01N 33/6854* (2013.01)

(58) Field of Classification Search
None
See application file for complete search history.

(56) References Cited

U.S. PATENT DOCUMENTS 10,253,109 B2 * 4/2019 Zimring .............. C07K 16/2896
2013/0288387 A1 10/2013 Blancher et al.
2014/0038210 A1 2/2014 Essig et al.
2015/0037819 A1 2/2015 Blancher et al.

FOREIGN PATENT DOCUMENTS

WO WO-2012162068 A2 * 11/2012 ......... C07K 16/2803

OTHER PUBLICATIONS

PCT International Search Report and Written Opinion, International Application No. PCT/US2016/053311 dated Apr. 7, 2017, 19 pp.
Boyland, et al., "Delayed hemolytic transfusion reaction caused by anti-Fyb in a splenectomized patient," Transfusion, vol. 22, No. 5, 1982, p. 402.
Campbell, et al., "Molecular cloning of the B-CAM cell surface glycoprotein of epithelial cancers: a novel member of the immunoglobulin superfamily," Cancer Res., vol. 54, No. 22, 1994, pp. 5761-5765.
Chaudhuri, et al., "Detection of Duffy antigen in the plasma membranes and caveolae of vascular endothelial and epithelial cells of nonerythroid organs," Blood, vol. 89, No. 2, 1997, pp. 701-712.
Daniels et al., "Causes of fetal anemia in hemolytic disease due to anti-K," Transfusion, vol. 43, No. 1, 2003, pp. 115-116.
Daniels, et al., "International Society of Blood Transfusion Committee on Terminology for Red Cell Surface Antigens: Cape Town report," Vox Sanguinis, vol. 92, No. 2007, pp. 250-253.
El Nemer, et al., "Organization of the human LU gene and molecular basis of the Lu(a)/Lu(b) blood group polymorphism," Blood, vol. 89, No. 12, 1997, pp. 4608-4616.
Goodrick et al., "Haemolytic disease of the fetus and newborn due to anti-Fy(a) and the potential clinical value of Duffy genotyping in pregnancies at risk," Transfusion Medicine, vol. 7, No. 4, 1997, pp. 301-304.
Hendrickson, et al., "Recipient inflammation affects the frequency and magnitude of immunization to transfused red blood cells," Transfusion, vol. 46 No. 9, 2006, pp. 1526-1536.
Inderbitzen, et al., "An example of HDN probably due to anti-Lua," Transfusion, vol. 22, No. 6, 1982, p. 542.
International Preliminary Report on Patentability dated Apr. 5, 2018 in International Application No. PCT/US16/53311, 9 pages.
Iwamoto, et al., "Genomic organization of the glycoprotein D gene: Duffy blood group Fya/Fyb alloantigen system is associated with a polymorphism at the 44-amino acid residue," Blood, vol. 85, No. 3, 1995, pp. 622-626.
Iwamoto, et al., "Identification of a novel exon and spliced form of Duffy mRNA that is the predominant transcript in both erythroid and postcapillary venule endothelium," Blood, vol. 87, No. 1, 1996, pp. 378-385.
Lee, "Molecular basis of Kell blood group phenotypes," Vox Sanguinis, vol. 73, No. 1, 1997, pp. 1-11.
Mallinson, et al., "Mutations in the erythrocyte chemokine receptor (Duffy) gene: the molecular basis of the Fya/Fyb antigens and identification of a deletion in the Duffy gene of an apparently healthy individual with the Fy(a-b-) phenotype," Br. J. Haematol. vol. 90, No. 4, 1995, pp. 823-882.
Parsons, et al., "The Lutheran blood group glycoprotein, another member of the immunoglobulin superfamily, is widely expressed in human tissues and is developmentally regulated in human liver," PNAS, vol. 92, No. 12, 1995, pp. 5496-5500.
Ridgwell et al., "Production of soluble recombinant proteins with Kell, Duffy and Lutheran blood group antigen activity, and their use in screening human sera for Kell, Duffy and Lutheran antibodies," Transfus. Med., vol. 17, No. 5, 2007, pp. 384-394.

(Continued)

*Primary Examiner* — Ellen J Marcsisin
(74) *Attorney, Agent, or Firm* — Lee & Hayes PC; C. Rachal Winger; Thu Nguyen

(57) ABSTRACT

Compositions and methods which are useful for determining the sensitivity and specificity of antibody detection reagents are disclosed.

13 Claims, 36 Drawing Sheets

Specification includes a Sequence Listing.

(56) References Cited

OTHER PUBLICATIONS

Russo, et al., "Expression of Kell blood group protein in nonerythroid tissues," Blood, vol. 96, No. 1, 2000, pp. 340-346.
Sosler, et al., "The prevalence of immunization to Duffy antigens in a population of known racial distribution," Transfusion, vol. 29, No. 6, 1989, pp. 505-507.
Tournamille, et al., "Molecular basis and PCR-DNA typing of the Fya/fyb blood group polymorphism," Human Genetics, vol. 95, No. 4, 1995, pp. 407-410.
Vaughan, et al., "Inhibition of erythroid progenitor cells by anti-Kell antibodies in fetal alloimmune anemia," N. Engl. J. Med., vol. 338, No. 12, 1998, pp. 798-803.
Vescio, et al., "Hemolytic disease of the newborn caused by anti-Fyb," Transfusion, vol. 27, No. 4, 1987, p. 366.

* cited by examiner

Heavy chain sequence of Puma1 and Puma2

Sequence G
(SEQ ID NO: 114)
EVQLQQSGPELVKPGASVKMSCKASGYTFT<u>DYYMK</u>WVKQSHGKSLEWIG<u>DLNPNNGDTFYNQKFKG</u>KATLTVDKSSS
TAYIQLNSLTSEDSAVYYC<u>AREAGSSEGSSCNYWG</u>QGTTLTVS (SEQ ID NO: 115)
(SEQ ID NO: 3)
Or:
(SEQ ID NO: 116)

```
142  angtctctccacagacactgaacacactgactcctccaacatgga
     M  S  S  P  Q  T  L  N  T  L  T  P  T  M  G
187  tggagctggatcttctctcttctcttgtcaggaactggaggtgtc
     W  S  W  I  F  L  F  L  S  G  T  G  G  V
232  ctctctgaggtccaactgcaacagtctggacctgagctggtgaag
     L  S  E  V  Q  L  Q  Q  S  G  P  E  L  V  K
277  cctggggcttcagtgaag  tcctgcaaggcttctggatacacc
     P  G  A  S  V  K     S  C  K  A  S  G  Y  T
322  ttcactgactactac   aagtggtgaagcagagccatggaag
     F  T  D  Y  Y     K  W  V  K  Q  S  H  G  K
367  agccttgagtggattggagatcttaatcctaacaatggtgatact
     S  L  E  W  I  G  D  L  N  P  N  N  G  D  T
412  ttctacaaccagaagttcaagggcaaggccacattgactgtagac
     F  Y  N  Q  K  F  K  G  K  A  T  L  T  V  D
457  aagtcctccagcacagcctacatccagctcaacagccttacatct
     K  S  S  S  T  A  Y  I  Q  L  N  S  L  T  S
502  gaggactctgcagtctattactgtgcaagagaggggggaagttcc
     E  D  S  A  V  Y  Y  C  A  R  E  A  G  S  S
547  ttcggtagtagctgtaattattgggcaaggccaccattctcaca
     F  G  S  S  C  N  Y  W  G  Q  G  T  T  L  T
592  gtctcctcagccagcaaaacggcccccatctgtctatccactgcc
     V  S  S  A  K  T  T  A  P  S  V  Y  P  L  A
637  aatcgaattcccgcgccantgccggccggaagcantgcgacgt
     N  R  I  P  A  A  A  M  M  A  A  G  S  M  R
682  cgggcccaattcgcccctatag 702        (SEQ ID NO: 4)
     R  A  Q  F  A  L  *                (SEQ ID NO: 5)
``` ccatctgtctatccactgcc (SEQ ID NO: 6) matches reverse complement DNA sequence of 3' primer for heavy chain

FIG. 1

Light chain sequence of Puma1 and Puma2

Sequence B
(SEQ ID NO: 117) (SEQ ID NO: 118)
SVVMTQTPKFLLVSAGDRVTITCKASQDVSTAVAWYQQKPGQSPKLLIYASNRYTGVPDRFTGSGYGTDFTFTISTVQ
AEDLAVYFCQQDYSSPYTFGGGTKLEIK (SEQ ID NO: 7)

Or:

(SEQ ID NO: 119)

```
778  atgaagtcacagaccaggtcttcgtatttctactgctctgtgtg
     M  K  S  Q  T  Q  V  F  F  L  L  L  C  V
733  tctggagttcatggagtgttgtgacccagactcccaagttc
     S  G  V  H  G  S  V  V  T  Q  T  P  K  F
688  ctgcttgtgtcagcgggagcgggtgacagggttaccatcacctgcaaggcc
     L  L  V  S  A  G  D  R  V  T  I  T  C  K  A
643  agtcagactgtgactgtgactagcttgtaccaacagcagcca
     S  Q  T  V  S  K  D  V  A  W  Y  Q  Q  P
598  gggcagtctcctaaactgctgatatactactgcatccaatcgctac
     G  Q  S  P  K  L  L  I  Y  Y  A  S  N  R  Y
553  actggagtccctgatcgcttcactggcagtggatctgggacggat
     T  G  V  P  D  R  F  T  G  S  G  Y  G  T  D
508  ttcacttccaccatcagcactgtgcaggctgaagacctggcagttt
     F  T  F  T  I  S  T  V  Q  A  E  D  L  A  V
463  tattctgtcagcaggattatagctctccgtacacgttcgggggg
     Y  F  C  Q  Q  D  I  S  S  P  Y  T  F  G  G
418  gggaccaagctggaaataaaacggctgatgctgcaccaactgta
     G  T  K  L  E  I  K  R  A  D  A  A  P  T  V
373  tccatcttcccaccatccagtgagcagttaacatctggaggtgcc
     S  I  F  P  P  S  S  E  Q  L  T  S  G  G  A
328  tcagtcgtgtgcttcttgaacaacttctacccagaaacatcaat
     S  V  V  C  F  L  N  N  F  Y  P  R  D  I  N
283  gtcaagtggaagattgatggcagtgaacagcagacacctgtcctg
     V  K  W  K  I  D  G  S  E  R  Q  N  G  V  L
238  aacagttggactgatcaggacagcaaggacagcacctacagcag
     N  S  W  T  D  Q  D  S  K  D  S  T  Y  S
193  agcagcaccctcacattgaccaaggacgagtatgaacgacataaac
     S  S  T  L  T  L  T  K  D  E  Y  E  R  H  N
148  agtatacctgtgaggccactcacaagacatcaacttcacccatc
     S  Y  T  C  E  A  T  H  K  T  S  P  I
103  gtcaagagcttcaacaggaataqtgtaatcactcag 68 (SEQ ID NO: 8)
     V  K  S  F  N  R  N  X  C  N  H           (SEQ ID NO: 9)
```

FIG. 2

Heavy chain sequence of Puma3

Sequence F        (SEQ ID NO: 120)              (SEQ ID NO: 121)

QVQLKESGPGLLAPSQSLSITCTVSGFSLTSYGVYWVRQPPGKGLEWLGIWGDGSTNYQSVLRSRLSITKDDSKSQVFL
KLNSLQTDDTATYYCAKRGDYDVAYWGQGTLVTVSA  (SEQ ID NO: 10)
               (SEQ ID NO: 122)

```
Or: 518  atggctgtcctgctcctctgcctggtgacattcccaagg
          M  A  V  L  L  L  C  L  V  T  F  P  R
    473  tgtgtcctgtcccaggtgcagctgaaggagtcaggacctggccta
          C  V  L  S  Q  V  Q  L  K  E  S  G  P  G  L
    428  ctggcgcccttacagagcctgtccatcacatgcactgtctcaggt
          L  A  P  S  Q  S  L  S  I  T  C  T  V  S  G
    383  ttctcgttaaccagctatggtgtatactgggttcgccagcctcca
          F  S  L  T  S  Y  G  V  Y  W  V  R  Q  P  P
    338  ggaaagggtctggagtggctggtacatatgggtgacggagc
          G  K  G  L  E  W  L  G  I  W  G  D  G  S
    293  acaaattatcagttctcagatccagactgagcatcaccaag
          T  N  Y  Q  S  V  L  R  S  R  L  S  I  T  K
    248  gatgactccaagagccaagtttctttaaacctgaacagtctacaa
          D  D  S  K  S  Q  V  F  L  K  L  N  S  L  Q
    203  actgatgacacagcaacagtactactgtgccaaacggggagattac
          T  D  D  T  A  T  Y  Y  C  A  K  R  G  D  Y
    158  gacgttgcttactgggccaagggaccactctggtcactgtctctgca
          D  V  A  Y  W  G  Q  G  T  L  V  T  V  S  A
    113  gccaaaacgacaccccatctgtctatcctnnagncaatcac    g  69  (SEQ ID NO: 11)
          A  K  T  T  P  P  S  V  Y  P  X  X  N  H            (SEQ ID NO: 12)
``` ccatctgtctat (SEQ ID NO: 13)
reverse complement DNA
sequence of 3' primer for heavy

FIG. 3

Light chain sequence of Puma3

Sequence C (SEQ ID NO: 123)　　(SEQ ID NO: 124)
DIVLTQSPASLAVSLGQRAIISCXASKXVSXXGXSXMXWYQQRPGQQPKLLIYXXXXLXAGVPTRFSGSGSRTDFTLNIH
PVEEDDAATYYCQQSREFPWTFGGGTRLEIK (SEQ ID NO: 14)

```
Or:   59  atgngactcantcnctgctgctntngtgctactgctctggtt
              M  X  T  X  S  L  L  L  X  V  L  L  L  W  V
     104  ccaggctccactggtgacattgtgctgacccaatctccagcttct
              Q  G  P  T  G  D  I  V  L  T  Q  S  P  A  S
     149  ttggctgtgtctctcaggcagagggccatcatctcctgcaaggcc
              L  A  V  S  L  G  Q  R  A  I  I  S  C  K  A
     194  agccaaactgtcagtttgtgggactagttta  cactggtat
              S  Q  T  V  S  F  V  G  T  S  L  H  W  Y
     239  caacagagaccaggacaggaaccaaacctcctcatctattcgtaca
              Q  Q  R  P  G  Q  Q  P  K  L  L  I  Y  R  T
     284  tccaacctagaagtgggtccaaccaggtttagtggcaagtggg
              S  N  L  E  A  G  V  P  T  R  F  S  G  S  G
     329  tctaggacagactttcaccctcaatatccatcctgtggaggaagat
              S  R  T  D  F  T  L  N  I  H  P  V  E  E  D
     374  gatgctgcaacctattactgtcagcaaagtagggaatttccgtgg
              D  A  A  T  Y  Y  C  Q  Q  S  R  E  F  P  W
     419  acgttcggtggaggcaccaaggctggaaatcaaacggcgtgatgcc
              T  F  G  G  G  T  R  L  E  I  K  R  A  D  A
     464  gcaccaactgtatccatcttcccaccatccagtgagcagttaaca
              A  P  T  V  S  I  F  P  P  S  S  E  Q  L  T
     509  tctggaggtgcctcagtcgtgtgcttcttgaacaacttctacccc
              S  G  G  A  S  V  V  C  F  L  N  N  F  Y  P
     554  agagacatcaatgtcaagtggaagattgatggcagtgaacgacaa
              R  D  I  N  V  K  W  K  I  D  G  S  E  R  Q
     599  aatggtgtcctgaacagttggactgatcaggacagcaaagacagc
              N  G  V  L  N  S  W  T  D  Q  D  S  K  D  S
     644  acctacagcatgagcagcaccctcacattgaccaaggacgagtat
              T  Y  S  M  S  S  T  L  T  L  T  K  D  E  Y
     689  gaacgacataactgcgaagccactcacaagacatca
              E  R  H  N  S  Y  T  C  E  A  T  X  K  T  S
     734  acttcacccatcgtcaagagcttcaacaggaatgagtgtaatcac (SEQ ID NO: 16)
              T  S  P  I  V  K  S  F  N  R  N  E  C  N  H
     779       781 (SEQ ID NO: 15)
```

FIG. 4

Heavy chain sequence of Puma 4

Sequence I
EVKLEESGGGLVQPGGSMKLSCVASGFTFS NYWMHWVRQPPEKGLEWVA EIRNSNNYATHYAESVKG KFTISRDDS
　　　　　　　　　　　　　　(SEQ ID NO: 125)　　　　　　　　　　(SEQ ID NO: 126)
KSSVYLQMNDLRAEDTGIYYCTR NWDFAW FDSWGQGTLVTVSA (SEQ ID NO: 17)
　　　　　　　　　　　　(SEQ ID NO: 127)

```
Or: 122  atggagacgcacaaccctgactcacaagtctttctcttcagt
         M  E  T  H  N  P  D  S  Q  V  F  L  F  S
    167  gacaaacacagaaatagaacattcaccantacttgggactgaac
         D  K  H  R  N  R  T  F  T  M  Y  L  G  L  N
    212  tgtgttattcatagttttctcttaaaaggtgtccagagtgaagtg
         C  V  F  I  H  S  F  L  K  G  V  Q  S  E  V
    257  aagcttgaggagtctggaggaggcttggtgcaacctggaggatcc
         K  L  E  E  S  G  G  G  L  V  Q  P  G  G  S
    302  aaactctcctgtgttgcctgtgcaccatttcagtaactac
         K  L  S  C  V  A  S  G  F  T  F  S  N  Y
    347  tgg  aactgggtccgccaacctccagagagaaggggcttgaatgg
         W  M  H  W  V  R  Q  P  P  E  K  G  L  E  W
    392  gttgctgaaattagattgaactctaataattatgcaacacattat
         V  A  E  I  R  I  N  S  N  N  Y  A  T  H  Y
    437  gcggagtctgtgaagggaaattcaccatctcaagagatgattcc
         A  E  S  V  K  G  K  F  T  I  S  R  D  D  S
    482  aaaagtagtgtctacctgcaa  aacgacttaagagctgaagac
         K  S  S  V  Y  L  Q  N  D  L  R  A  E  D
    527  actggcatttattactgtctatcactggccactgggactttgcctggttt
         T  G  I  Y  Y  C  T  R  N  W  D  F  A  W  F
    572  gattcctggggccaaggggactctggtcactgtctctgcagccaaa
         D  S  W  G  Q  G  T  L  V  T  V  S  A  K
    617  acaacagcccatctgtctatccactgccaatcgaattcccgcg
         T  T  A  P  S  V  Y  P  L  A  N  R  I  P  A
    662  gccgcaaagcggccggagcagcgacgtcgggcccaattcgcc
         A  A  K  A  A  G  S  M  R  R  R  A  Q  F  A
    707  ctataan 712  (SEQ ID NO: 18)
         L  *       (SEQ ID NO: 19)
``` ccatctgtctatccactggcc (SEQ ID NO: 6) matches reverse complement DNA sequence of 3' primer for heavy chain

FIG. 5

Light chain sequence of Puma4

Sequence D (SEQ ID NO: 128) (SEQ ID NO: 129)
DIVMTQSHKFMSTSVGDRVSITC KASQDVSTAVA WYQQKPGQSPKLLIY WASTRHT GVPDRFTGSGSGTDYTLTISSV
QAEDLALYYC QQHYTTPFT FGSGTKLEIK (SEQ ID NO: 20)
(SEQ ID NO: 130)

```
Or:  811  at gggga   catcgaccagc   gcatcaag   gagtca
              M  G  E  M  H  R  T  S  M  G  I  K  M  E  S
     766  cagatccaggcoatttgtattcogtgtttctggtgtctggtgtt
              Q  I  Q  A  F  V  F  V  F  L  W  L  S  G  V
     721  gacggagacattgt    accoagtctcacaaattc    gtccaca
              D  G  D  I  V  M  T  Q  S  H  K  F  M  S  T
     676  tcagtaggagacagggtcagatcatcctgcaaggccagtcaagat
              S  V  G  D  R  V  S  I  T  C  K  A  S  Q  D
     631  gtgagtactgttgtggctgtatcaacaaccaaggccattct
              V  S  T  V  V  A  W  Y  Q  Q  R  P  G  Q  S
     586  cctaaactcctgatttactgggcatccactoggcacctggagtt
              P  K  L  L  I  Y  W  A  S  T  R  H  T  G  V
     541  cctgatcgcttcacaggcagtggatctggacagattatactctc
              P  D  R  F  T  G  S  G  S  G  T  D  Y  T  L
     496  accatcagcagtgtgcaggctgaagacctggcacttattactgt
              T  I  S  S  V  Q  A  E  D  L  A  L  Y  Y  C
     451  cagcaacattatacgactccattcacgttcggctcggggacaaag
              Q  Q  H  Y  T  T  P  F  T  F  G  S  G  T  K
     406  ttggaaataaaacggagctgatgctgcaccaacttgatcoatcttc
              L  E  I  K  R  A  D  A  A  P  T  V  S  I  F
     361  ccaccatccagtgagcagttaacatctgaaggtgcctcagtcgtg
              P  P  S  S  E  Q  L  T  S  G  G  A  S  V  V
     316  tgcttcttgaacaacttctaccoagagacaaatgtcaatgtcaagtgg
              C  F  L  N  N  F  Y  P  R  D  I  N  V  K  W
     271  aagattgatggcagtgaacgacaaaatgtgtctgaacagttgg
              K  I  D  G  S  E  R  Q  N  G  V  L  N  S  W
     226  actgatcaggacagcaaagacagcacctacagc   agcagcacc
              T  D  Q  D  S  K  D  S  T  Y  S  S  S  T
     181  ctcacattgaccaaggacgagtatgaacgacataacagctataac
              L  T  L  T  K  D  E  Y  E  R  H  N  S  Y  T
     136  tgtgaggccactcacaagacatccacttcaccoatcgtcaagagc
              C  E  A  T  H  K  T  S  T  S  P  I  V  K  S
      91  ttcaacaggaatgagtgtaatcact g 65 (SEQ ID NO: 21)
              F  N  R  N  E  C  N  H       (SEQ ID NO: 22)
```

FIG. 6

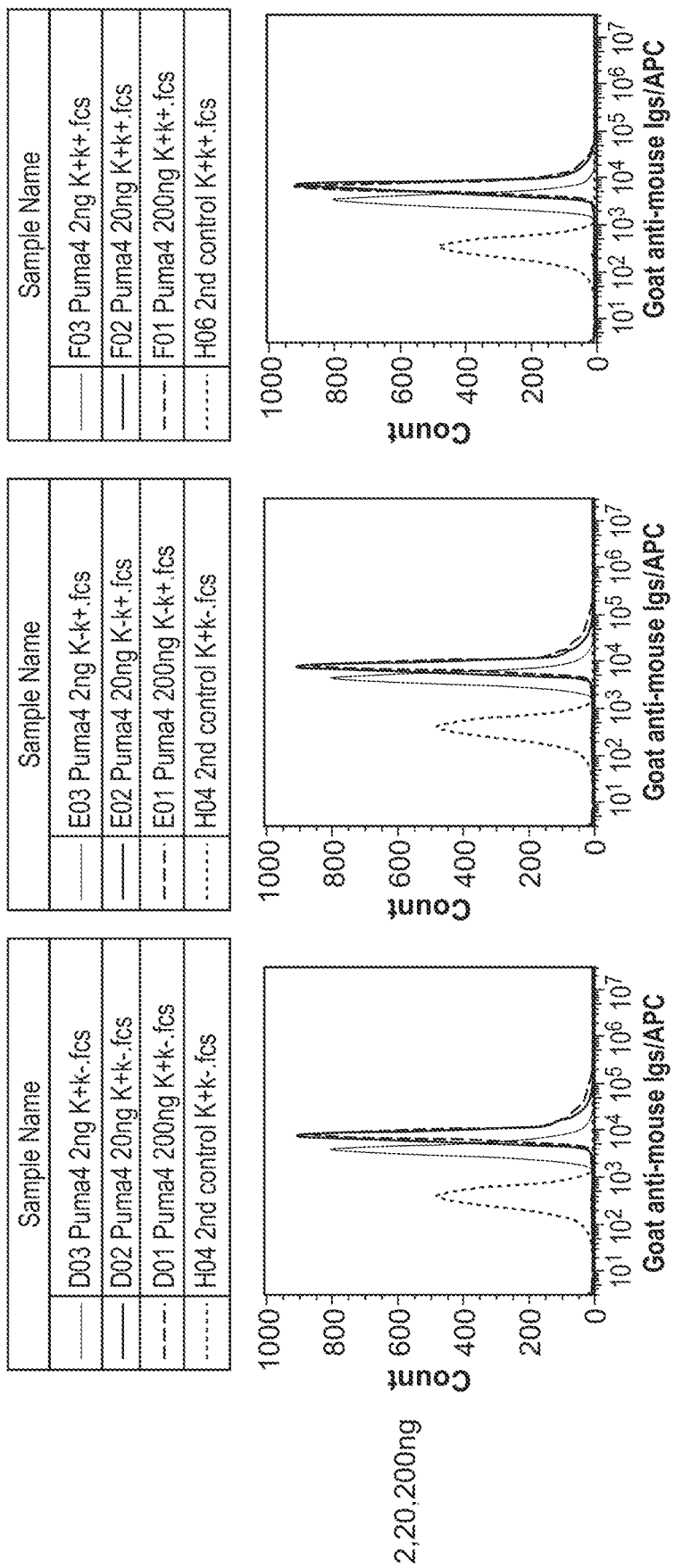
FIG. 10 (Cont. 1)

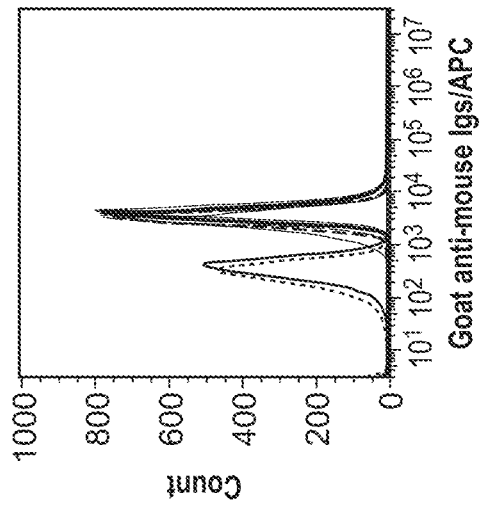
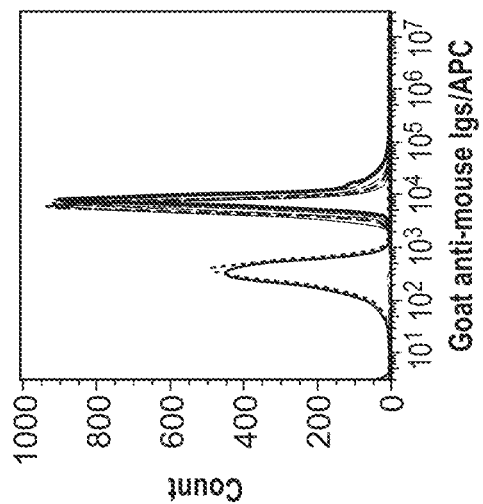
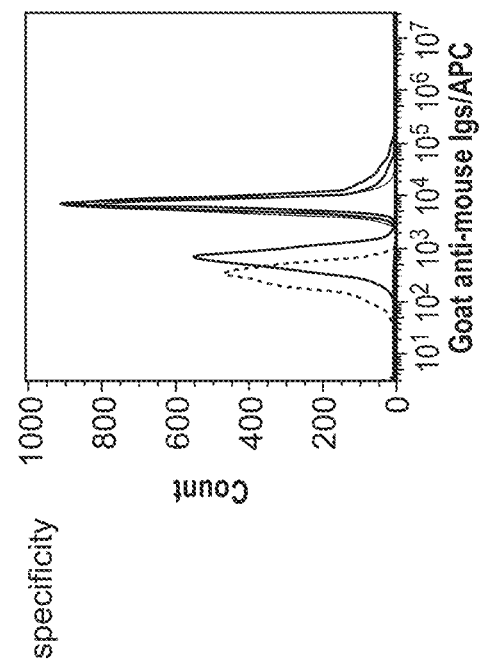
FIG. 10 (Cont. 2)

Human PUMA1 IgG constructs:

>PUMA1-hG1
MSSPQTLNTLTPTMGWSWIFLFLLSGTGGVLSEVQLQQSGPELVKPGASVKMSCKASGYTFTDYY
MKWVKQSHGKSLEWIGDLNPNNGDTFYNQKFKGKATLTVDKSSSTAYIQLNSLTSEDSAVYYCARE
AGSSFGSSCNYWGQGTTLTVSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQGNVFSC
SVMHEALHNHYTQKSLSLSPGK (SEQ ID NO: 23)

>PUMA1-hG2
MSSPQTLNTLTPTMGWSWIFLFLLSGTGGVLSEVQLQQSGPELVKPGASVKMSCKASGYTFTDYY
MKWVKQSHGKSLEWIGDLNPNNGDTFYNQKFKGKATLTVDKSSSTAYIQLNSLTSEDSAVYYCARE
AGSSFGSSCNYWGQGTTLTVSASTKGPSVFPLAPCSRSTSESTAALGCLVKDYFPEPVTVSWNSG
ALTSGVHTFPAVLQSSGLYSLSSVVTVPSSNFGTQTYTCNVDHKPSNTKVDKTVERKCCVECPPCP
APPVAGPSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSREEMTKNQ
VSLTCLVKGFYPSDIAVEWESNGQPENNYKTTPPMLDSDGSFFLYSKLTVDKSRWQQGNVFSCSV
MHEALHNHYTQKSLSLSPGK (SEQ ID NO: 24)

>PUMA1-hG3
MSSPQTLNTLTPTMGWSWIFLFLLSGTGGVLSEVQLQQSGPELVKPGASVKMSCKASGYTFTDYY
MKWVKQSHGKSLEWIGDLNPNNGDTFYNQKFKGKATLTVDKSSSTAYIQLNSLTSEDSAVYYCARE
AGSSFGSSCNYWGQGTTLTVSASTKGPSVFPLAPCSRSTSGGTAALGCLVKDYFPEPVTVSWNSG
ALTSGVHTFPAVLQSSGLYSLSSVVTVPSSSLGTQTYTCNVNHKPSNTKVDKRVELKTPLGDTTHT
CPRCPEPKSCDTPPPCPRCPEPKSCDTPPPCPRCPEPKSCDTPPPCPRCPAPELLGGPSVFLFPP
KPKDTLMISRTPEVTCVVVDVSHEDPEVQFKWYVDGVEVHNAKTKPREEQYNSTFRVVSVLTVLHQ
DWLNGKEYKCKVSNKALPAPIEKTISKTKGQPREPQVYTLPPSREEMTKNQVSLTCLVKGFYPSDIA
VEWESSGQPENNYNTTPPMLDSDGSFFLYSKLTVDKSRWQQGNIFSCSVMHEALHNRFTQKSLSL
SPGK (SEQ ID NO: 25)

>PUMA1-hG4
MSSPQTLNTLTPTMGWSWIFLFLLSGTGGVLSEVQLQQSGPELVKPGASVKMSCKASGYTFTDYY
MKWVKQSHGKSLEWIGDLNPNNGDTFYNQKFKGKATLTVDKSSSTAYIQLNSLTSEDSAVYYCARE
AGSSFGSSCNYWGQGTTLTVSASTKGPSVFPLAPCSRSTSESTAALGCLVKDYFPEPVTVSWNSG
ALTSGVHTFPAVLQSSGLYSLSSVVTVPSSSLGTKTYTCNVDHKPSNTKVDKRVESKYGPPCPSCP
APEFLGGPSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRLTVDKSRWQEGNVFSCSV
MHEALHNHYTQKSLSLSPGK (SEQ ID NO: 26)

FIG. 11A

CLUSTAL 2.1 multiple sequence alignment

```
PUMA1-hG1    MSSPQTLNTLTPTMGWSWIFLFLLSGTGGVLSEVQLQQSGPELVKPGASVKMSCKASGYT  60
PUMA1-hG2    MSSPQTLNTLTPTMGWSWIFLFLLSGTGGVLSEVQLQQSGPELVKPGASVKMSCKASGYT  60
PUMA1-hG3    MSSPQTLNTLTPTMGWSWIFLFLLSGTGGVLSEVQLQQSGPELVKPGASVKMSCKASGYT  60
PUMA1-hG4    MSSPQTLNTLTPTMGWSWIFLFLLSGTGGVLSEVQLQQSGPELVKPGASVKMSCKASGYT  60
             ************************************************************

PUMA1-hG1    FTDYYMKWVKQSHGKSLEWIGDLNPNNGDTFYNQKFKGKATLTVDKSSSTAYIQLNSLTS 120
PUMA1-hG2    FTDYYMKWVKQSHGKSLEWIGDLNPNNGDTFYNQKFKGKATLTVDKSSSTAYIQLNSLTS 120
PUMA1-hG3    FTDYYMKWVKQSHGKSLEWIGDLNPNNGDTFYNQKFKGKATLTVDKSSSTAYIQLNSLTS 120
PUMA1-hG4    FTDYYMKWVKQSHGKSLEWIGDLNPNNGDTFYNQKFKGKATLTVDKSSSTAYIQLNSLTS 120
             ************************************************************

PUMA1-hG1    EDSAVYYCAREAGSSFGSSCNYWGQGTTLTVSASTKGPSVFPLAPSSKSTSGGTAALGCL 180
PUMA1-hG2    EDSAVYYCAREAGSSFGSSCNYWGQGTTLTVSASTKGPSVFPLAPCSRSTSESTAALGCL 180
PUMA1-hG3    EDSAVYYCAREAGSSFGSSCNYWGQGTTLTVSASTKGPSVFPLAPCSRSTSGGTAALGCL 180
PUMA1-hG4    EDSAVYYCAREAGSSFGSSCNYWGQGTTLTVSASTKGPSVFPLAPCSRSTSESTAALGCL 180
             *********************************************  * ***  ******

PUMA1-hG1    VKDYFPEPVTVSWNSGALTSGVHTFPAVLQSSGLYSLSSVVTVPSSSLGTQTYICNVNHK 240
PUMA1-hG2    VKDYFPEPVTVSWNSGALTSGVHTFPAVLQSSGLYSLSSVVTVPSSNFGTQTYTCNVDHK 240
PUMA1-hG3    VKDYFPEPVTVSWNSGALTSGVHTFPAVLQSSGLYSLSSVVTVPSSSLGTQTYTCNVNHK 240
PUMA1-hG4    VKDYFPEPVTVSWNSGALTSGVHTFPAVLQSSGLYSLSSVVTVPSSSLGTKTYTCNVDHK 240
             **********************************************  ** ** *** **

PUMA1-hG1    PSNTKVDKKVEPK----SCDKTHT------------------------------------ 260
PUMA1-hG2    PSNTKVDKTVE------RKCCVE------------------------------------- 257
PUMA1-hG3    PSNTKVDKRVELKTPLGDTTHTCPRCFEPKSCDTPPPCPRCPEPKSCDTPFPCPRCPEPK 300
PUMA1-hG4    PSNTKVDKRVE------SKYGPP------------------------------------- 257
             ********  **

PUMA1-hG1    --------CPPCPAPELLGGPSVFLFPPKPKDTLMISRTPEVTCVVVDVSHEDPEVKFNWY 313
PUMA1-hG2    --------CPPCPAPPV-AGPSVFLFPPKPKDTLMISRTPEVTCVVVDVSHEDPEVQFNWY 309
PUMA1-hG3    SCDTPPPCPRCPAPELLGGPSVFLFPPKPKDTLMISRTPEVTCVVVDVSHEDPEVQFKWY 360
PUMA1-hG4    --------CPSCPAPEFLGGPSVFLFPPKPKDTLMISRTPEVTCVVVDVSQEDPEVQFNWY 310
                    ** ****  ***********************************  ***** *  **

PUMA1-hG1    VDGVEVHNAKTKPREEQYNSTYRVVSVLTVLHQDWLNGKEYKCKVSNKALPAPIEKTISK 373
PUMA1-hG2    VDGVEVHNAKTKPREEQFNSTFRVVSVLTVVHQDWLNGKEYKCKVSNKGLPAPIEKTISK 369
PUMA1-hG3    VDGVEVHNAKTKPREEQYNSTFRVVSVLTVLHQDWLNGKEYKCKVSNKALPAPIEKTISK 420
PUMA1-hG4    VDGVEVHNAKTKPREEQFNSTYRVVSVLTVLHQDWLNGKEYKCKVSNKGLPSSIEKTISK 370
             ***************** ****  *** *******  ***********************  **   *******

PUMA1-hG1    AKGQPREPQVYTLPPSREEMTKNQVSLTCLVKGFYPSDIAVEWESNGQPENNYKTTPPVL 433
PUMA1-hG2    TKGQPREPQVYTLPPSREEMTKNQVSLTCLVKGFYPSDIAVEWESNGQPENNYKTTPPML 429
PUMA1-hG3    TKGQPREPQVYTLPPSREEMTKNQVSLTCLVKGFYPSDIAVEWESSGQPENNYNTTPPML 480
PUMA1-hG4    AKGQPREPQVYTLPPSQEEMTKNQVSLTCLVKGFYPSDIAVEWESNGQPENNYKTTPPVL 430
              **************  ***************************  *******  **** *

PUMA1-hG1    DSDGSFFLYSKLTVDKSRWQQGNVFSCSVMHEALHNHYTQKSLSLSPGK 482 (SEQ ID NO: 23)
PUMA1-hG2    DSDGSFFLYSKLTVDKSRWQQGNVFSCSVMHEALHNHYTQKSLSLSPGK 478 (SEQ ID NO: 24)
PUMA1-hG3    DSDGSFFLYSKLTVDKSRWQQGNIFSCSVMHEALHNRFTQKSLSLSPGK 529 (SEQ ID NO: 25)
PUMA1-hG4    DSDGSFFLYSRLTVDKSRWQEGNVFSCSVMHEALHNHYTQKSLSLSPGK 479 (SEQ ID NO: 26)
             ********** ********** ** ************ ***********
```

FIG. 11B

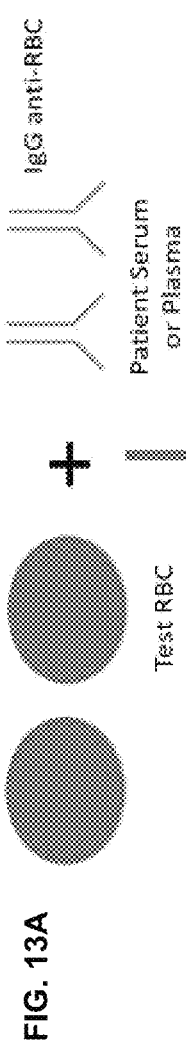
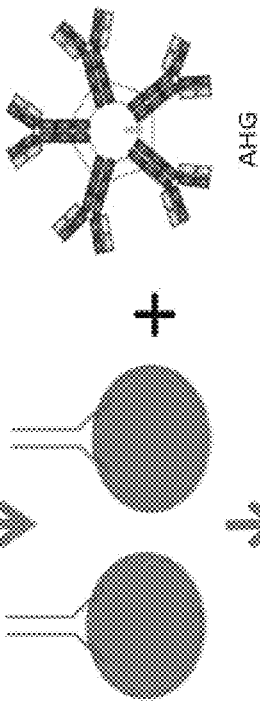
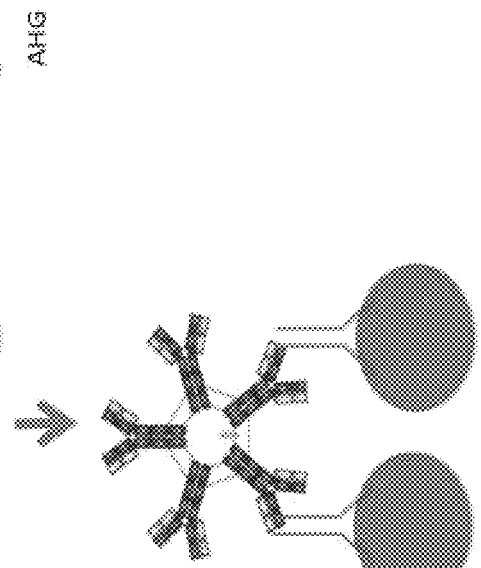
FIG. 13A
FIG. 13B
FIG. 13C

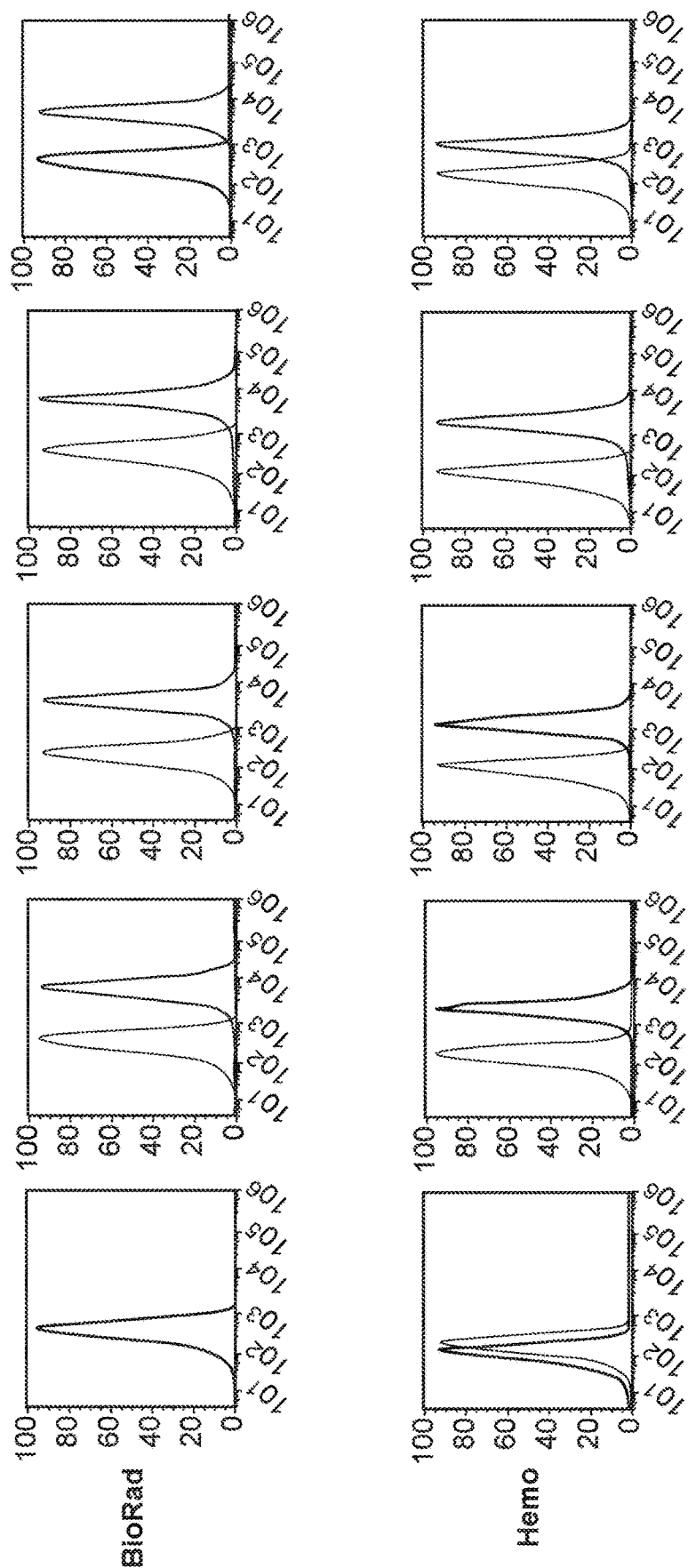
FIG. 15 (Cont. 1)

Echo Solid phase testing

| | | CH1 residues | | | | | | | | | | | | Hinge | | | |
|---|---|---|---|---|---|---|---|---|---|---|---|---|---|---|---|---|---|
| | | 131 | 133 | 137 | 138 | 176 | 189 | 192 | 193 | 196 | 199 | 203 | 214 | H1 | H2 | H3 | H4 |
| IgG1 | IGHG1*01 | S | K | G | G | S | P | S | L | Q | I | N | K | (SEQ ID NO: 27) | | | |
| | IGHG1*03 | S | K | G | G | S | P | S | L | Q | I | N | <u>R</u> | (SEQ ID NO: 30) | | | |
| | IGHG1*04 | S | K | G | G | S | P | S | L | Q | I | N | K | (SEQ ID NO: 33) | | | |
| | IGHG1*07 | S | K | G | G | S | P | S | L | Q | I | N | K | (SEQ ID NO: 36) | IgG1 Hinge | | | |
| | IGHG1*08 | S | K | G | G | S | P | S | L | Q | I | N | <u>R</u> | (SEQ ID NO: 39) | | | |
| | IGHG1*01v2 | S | K | G | G | S | P | S | L | Q | I | N | K | (SEQ ID NO: 42) | | | |
| | IGHG1*04v2 | S | K | G | G | S | P | S | L | Q | I | N | K | (SEQ ID NO: 45) | | | |
| IgG2 | IGHG2*01 | C | R | E | S | S | P | N | F | Q | T | D | T | (SEQ ID NO: 48) | | | |
| | IGHG2*02 | C | R | E | S | S | <u>T</u> | N | F | Q | T | D | T | (SEQ ID NO: 51) | IgG2 Hinge | | | |
| | IGHG2*04 | C | R | E | S | S | P | <u>S</u> | <u>L</u> | Q | T | D | T | (SEQ ID NO: 54) | | | |
| | IGHG2*06 | C | R | E | S | S | P | N | F | Q | T | D | T | (SEQ ID NO: 57) | | | |
| IgG3 | IGHG3*01 | C | R | G | G | S | P | S | L | Q | T | N | R | (SEQ ID NO: 60) | + | + | + | + |
| | IGHG3*03 | C | R | G | G | S | P | S | L | Q | T | N | R | (SEQ ID NO: 63) | + | | + | + |
| | IGHG3*04 | C | R | G | G | S | P | S | L | Q | T | N | R | (SEQ ID NO: 66) | + | | | + |
| | IGHG3*06 | C | R | G | G | S | P | S | L | Q | T | N | R | (SEQ ID NO: 69) | + | + | + | + |
| | IGHG3*08 | C | R | G | G | S | P | S | L | Q | T | N | R | (SEQ ID NO: 72) | + | + | + | + |
| | IGHG3*09 | C | R | G | G | S | P | S | L | Q | T | N | R | (SEQ ID NO: 75) | + | + | + | + |
| | IGHG3*11 | C | R | G | G | S | P | S | L | Q | T | N | R | (SEQ ID NO: 78) | + | + | + | + |
| | IGHG3*12 | C | R | G | G | S | P | S | L | Q | T | N | R | (SEQ ID NO: 81) | + | | + | + |
| | IGHG3*13 | C | R | G | G | S | P | S | L | Q | T | N | R | (SEQ ID NO: 84) | + | + | + | + |
| | IGHG3*14 | C | R | G | G | S | P | S | L | Q | T | N | R | (SEQ ID NO: 87) | + | + | + | + |
| | IGHG3*15 | C | R | G | G | S | P | S | L | Q | T | N | R | (SEQ ID NO: 90) | + | + | + | + |
| | IGHG3*16 | C | R | G | G | S | P | S | L | Q | T | N | R | (SEQ ID NO: 93) | + | + | + | + |
| | IGHG3*17 | C | R | G | G | S | P | <u>N</u> | <u>F</u> | Q | T | N | R | (SEQ ID NO: 96) | + | | + | + |
| | IGHG3*18 | C | R | G | G | <u>Y</u> | P | S | L | Q | T | N | R | (SEQ ID NO: 99) | + | | + | + |
| | IGHG3*19 | C | R | G | G | S | P | S | L | Q | T | N | R | (SEQ ID NO: 102) | + | | + | + |
| IgG4 | IGHG4*01 | C | R | E | S | S | P | S | L | K | T | D | R | (SEQ ID NO: 105) | | | |
| | IGHG4*02 | C | R | E | S | S | P | S | L | K | T | D | R | (SEQ ID NO: 108) | IgG4 Hinge | | | |
| | IGHG4*03 | C | R | E | S | S | P | S | L | K | T | D | R | (SEQ ID NO: 111) | | | |

| | | 233 | 234 | 235 | 236 | 268 | 274 | 276 | 282 | 291 | 292 | 296 | 300 | 309 | 327 | 330 | 331 | 339 | |
|---|---|---|---|---|---|---|---|---|---|---|---|---|---|---|---|---|---|---|---|
| | CH2 residues | | | | | | | | | | | | | | | | | | |
| IgG1 | IGHG1*01 | E | L | L | G | H | K | N | V | P | R | Y | Y | L | A | A | P | A | (SEQ ID NO: 28) |
| | IGHG1*03 | E | L | L | G | H | K | N | V | P | R | Y | Y | L | A | A | P | A | (SEQ ID NO: 31) |
| | IGHG1*04 | E | L | L | G | H | K | N | V | P | R | Y | Y | L | A | A | P | A | (SEQ ID NO: 34) |
| | IGHG1*07 | E | L | L | G | H | K | N | V | P | R | Y | Y | L | A | A | P | A | (SEQ ID NO: 37) |
| | IGHG1*08 | E | L | L | G | H | K | N | V | P | R | Y | Y | L | A | A | P | A | (SEQ ID NO: 40) |
| | IGHG1*01v2 | E | L | L | G | H | K | N | V | P | R | Y | Y | L | A | A | P | A | (SEQ ID NO: 43) |
| | IGHG1*04v2 | E | L | L | G | H | K | N | V | P | R | Y | Y | L | A | A | P | A | (SEQ ID NO: 46) |
| IgG2 | IGHG2*01 | P | V | A | - | H | Q | N | V | P | R | F | F | V | G | A | P | T | (SEQ ID NO: 49) |
| | IGHG2*02 | P | A | A | - | H | Q | N | M | P | R | F | F | V | G | A | P | T | (SEQ ID NO: 52) |
| | IGHG2*04 | P | V | A | - | H | Q | N | V | P | R | F | F | V | G | A | P | T | (SEQ ID NO: 55) |
| | IGHG2*06 | P | V | A | - | H | Q | N | V | P | R | F | F | V | G | A | P | T | (SEQ ID NO: 58) |
| IgG3 | IGHG3*01 | E | L | L | G | H | Q | K | V | P | R | Y | F | L | A | A | P | T | (SEQ ID NO: 61) |
| | IGHG3*03 | E | L | L | G | H | Q | K | V | P | R | Y | F | L | A | A | P | T | (SEQ ID NO: 64) |
| | IGHG3*04 | E | L | L | G | H | Q | K | V | P | R | Y | F | L | A | A | P | T | (SEQ ID NO: 67) |
| | IGHG3*06 | E | L | L | G | H | Q | K | V | P | R | Y | F | L | A | A | P | T | (SEQ ID NO: 70) |
| | IGHG3*08 | E | L | L | G | H | Q | K | V | P | R | Y | F | V | A | A | P | T | (SEQ ID NO: 73) |
| | IGHG3*09 | E | L | L | G | H | Q | K | V | P | R | Y | F | L | A | A | P | T | (SEQ ID NO: 76) |
| | IGHG3*11 | E | L | L | G | H | Q | K | V | P | R | E | F | L | A | A | P | T | (SEQ ID NO: 79) |
| | IGHG3*12 | E | L | L | G | H | Q | K | V | P | R | E | F | L | A | A | P | T | (SEQ ID NO: 82) |
| | IGHG3*13 | E | L | L | G | H | Q | K | V | P | R | Y | F | L | A | A | P | T | (SEQ ID NO: 85) |
| | IGHG3*14 | E | L | L | G | H | Q | K | V | P | R | Y | F | L | A | A | P | T | (SEQ ID NO: 88) |
| | IGHG3*15 | E | L | L | G | H | Q | K | V | L | R | Y | F | L | A | A | P | T | (SEQ ID NO: 91) |
| | IGHG3*16 | E | L | L | G | H | Q | K | V | L | R | Y | F | L | A | A | P | T | (SEQ ID NO: 94) |
| | IGHG3*17 | E | L | L | G | H | Q | K | V | P | R | Y | F | L | A | A | P | T | (SEQ ID NO: 97) |
| | IGHG3*18 | E | L | L | G | H | Q | K | V | P | W | Y | F | L | A | A | P | A | (SEQ ID NO: 100) |
| | IGHG3*19 | E | L | L | G | H | Q | K | V | P | W | Y | F | L | A | A | P | T | (SEQ ID NO: 103) |
| IgG4 | IGHG4*01 | E | F | L | G | Q | Q | N | V | P | R | F | Y | L | G | S | S | A | (SEQ ID NO: 106) |
| | IGHG4*02 | E | F | L | G | Q | Q | N | V | P | R | F | Y | V | G | S | S | A | (SEQ ID NO: 109) |
| | IGHG4*03 | E | F | L | G | Q | Q | N | V | P | R | F | Y | L | G | S | S | A | (SEQ ID NO: 112) |

| | | 355 | 356 | 358 | 378 | 379 | 384 | 392 | 397 | 409 | 419 | 422 | 431 | 435 | 436 | |
|---|---|---|---|---|---|---|---|---|---|---|---|---|---|---|---|---|
| | CH3 residues | | | | | | | | | | | | | | | |
| IgG1 | IGHG1*01 | R | D | L | A | V | N | K | V | K | Q | V | A | H | Y | (SEQ ID NO: 29) |
| | IGHG1*03 | R | E | M | A | V | N | K | V | K | Q | V | A | H | Y | (SEQ ID NO: 32) |
| | IGHG1*04 | R | D | L | A | V | N | K | V | K | Q | L | A | H | Y | (SEQ ID NO: 35) |
| | IGHG1*07 | R | D | L | A | V | N | K | V | K | Q | V | G | H | Y | (SEQ ID NO: 38) |
| | IGHG1*08 | R | D | L | A | V | N | K | V | K | Q | V | A | H | Y | (SEQ ID NO: 41) |
| | IGHG1*01v2 | R | D | L | A | V | N | K | V | K | Q | V | A | R | Y | (SEQ ID NO: 44) |
| | IGHG1*04v2 | R | D | L | A | V | N | K | V | K | Q | L | A | R | Y | (SEQ ID NO: 47) |
| IgG2 | IGHG2*01 | R | E | M | A | V | N | K | M | K | Q | V | A | H | Y | (SEQ ID NO: 50) |
| | IGHG2*02 | R | E | M | A | V | N | K | M | K | Q | V | A | H | Y | (SEQ ID NO: 53) |
| | IGHG2*04 | R | E | M | S | V | N | K | M | K | Q | V | A | H | Y | (SEQ ID NO: 56) |
| | IGHG2*06 | R | E | M | A | V | N | K | M | K | Q | V | A | H | Y | (SEQ ID NO: 59) |
| IgG3 | IGHG3*01 | R | E | M | A | V | S | N | M | K | Q | I | A | R | F | (SEQ ID NO: 62) |
| | IGHG3*03 | R | E | M | A | V | S | N | Y | R | E | — | A | R | F | (SEQ ID NO: 65) |
| | IGHG3*04 | R | E | M | A | V | S | N | M | K | Q | — | A | R | F | (SEQ ID NO: 68) |
| | IGHG3*06 | R | E | M | A | V | S | K | M | K | Q | — | A | R | F | (SEQ ID NO: 71) |
| | IGHG3*08 | R | E | M | A | V | S | N | M | K | Q | — | A | R | F | (SEQ ID NO: 74) |
| | IGHG3*09 | R | E | M | A | V | S | N | M | K | Q | — | A | R | F | (SEQ ID NO: 77) |
| | IGHG3*11 | R | E | M | A | V | N | N | M | K | E | — | A | R | F | (SEQ ID NO: 80) |
| | IGHG3*12 | R | E | M | A | V | S | N | M | K | Q | — | A | R | F | (SEQ ID NO: 83) |
| | IGHG3*13 | R | E | M | A | V | S | K | M | K | Q | — | A | R | F | (SEQ ID NO: 86) |
| | IGHG3*14 | R | E | M | A | V | N | N | M | K | E | — | A | R | F | (SEQ ID NO: 89) |
| | IGHG3*15 | R | E | M | A | V | S | N | M | K | Q | — | A | R | F | (SEQ ID NO: 92) |
| | IGHG3*16 | R | E | M | A | M | S | K | Y | K | Q | — | A | H | Y | (SEQ ID NO: 95) |
| | IGHG3*17 | R | E | M | A | M | N | K | Y | K | Q | — | A | H | Y | (SEQ ID NO: 98) |
| | IGHG3*18 | R | E | M | A | M | S | K | Y | K | Q | — | A | H | Y | (SEQ ID NO: 101) |
| | IGHG3*19 | R | E | M | A | V | S | N | M | K | Q | — | A | R | Y | (SEQ ID NO: 104) |
| IgG4 | IGHG4*01 | Q | E | M | A | V | N | K | V | R | E | V | A | H | Y | (SEQ ID NO: 107) |
| | IGHG4*02 | Q | E | M | A | V | N | K | V | R | E | V | A | H | Y | (SEQ ID NO: 110) |
| | IGHG4*03 | Q | E | M | A | V | N | K | V | K | E | V | A | H | Y | (SEQ ID NO: 113) |

FIG. 29 cont'd

COMPOSITION AND METHODS FOR ASSESSING SENSITIVITY AND SPECIFICITY OF ANTIBODY DETECTION REAGENTS

CROSS-REFERENCE TO RELATED APPLICATIONS

This application is a U.S. National Phase application based on International Application No. PCT/US2016/053311, filed Sep. 23, 2016, which claims the benefit of priority to U.S. Provisional Patent Application No. 62/232,310, filed Sep. 24, 2015 and 62/368,069 filed Jul. 28, 2016, each of which is incorporated herein by reference in its entirety as if fully set forth herein.

STATEMENT REGARDING SEQUENCE LISTING

The instant application contains a Sequence Listing which has been submitted electronically in ASCII format and is hereby incorporated by reference in its entirety. Said ASCII copy, created on Dec. 13, 2018, is named B212-0008US_ST25.txt and is 85 KB in size.

FIELD

The invention relates to compositions and methods useful for determining the sensitivity and specificity of antibody detection reagents.

INTRODUCTION

Humans naturally carry ABO antigens and express anti-A and/or anti-B if they do not express A or B, respectively. In addition to ABO, there are in excess of 340 RBC alloantigens in humans, each of which vary person to person. While anti-A and anti-B develop in essentially all people as "naturally occurring" alloantibodies, antibodies to the other alloantigens typically have to be induced by transfusion and/or pregnancy. However, only some patients make such antibodies. Once an anti-RBC alloantibody is made, then a patient often cannot be transfused with RBCs expressing the recognized alloantigen. It is for this reason that patients, prior to transfusion, are screened for the presence of RBC alloantibodies.

SUMMARY

In one aspect, disclosed herein is a method to determine the specificity and sensitivity of an anti-human globulin including the steps of: a) binding the anti-human globulin antibody to be tested to a panel of human antibodies of different subtype, and b) detecting the binding of the anti-human globulin to a subtype, thus determining the specificity and sensitivity of the anti-human globulin.

In some embodiments, the human antibody is an IgG. In some embodiments, the subtype includes IgG1, IgG2, IgG3, and IgG4. In some embodiments, the panel of human antibodies of different subtype includes the antigen binding sites of PUMA1. In some embodiments, the panel of human antibodies is at least one of PUMA 1 IgG1, IgG2, IgG3, and IgG4. In some embodiments, the human antibody is IgA, IgM, IgE, or IgD.

In other embodiments, the human antibody binds a member of the Kell blood group antigen system, for example, KEL1, KEL2, KEL3, KEL4, KEL5, KEL6, or KEL7. In particular embodiments, the Kell blood group antigen is K, $Kp^b$, or $Js^b$.

In further embodiments, the human antibody includes a heavy chain including at least one CDR selected from the group of CDR sequences shown in FIG. 1.

In yet further embodiments, the human antibody includes a light chain including at least one CDR selected from the group of CDR sequences shown in FIG. 2.

In other embodiments, the human antibody includes a heavy chain including one, two, or three CDR(s) selected from the group of CDR sequences shown in FIG. 1.

In other embodiments, the human antibody includes a light chain including one, two, or three CDR(s) selected from the group of CDR sequences shown in FIG. 2.

In other embodiments, the human antibody includes a heavy chain including at least a portion of the sequence shown in FIG. 1.

In other embodiments, the human antibody includes a light chain including at least a portion of the sequence shown in FIG. 2.

In some embodiments, the antibody or fragment thereof binds to an antigen with an affinity constant ($K_D$) of less than $1 \times 10^{-8}$ M.

In some embodiments, the antibody or fragment thereof binds to an antigen with an affinity constant ($K_D$) of less than $1 \times 10^{-9}$ M.

In some embodiments, disclosed herein is an expression vector including a nucleic acid encoding the human antibody disclosed above.

In some embodiments, the expression vector is in a host cell, which can include a bacterial cell or a eukaryotic cell, such as a mammalian cell.

In some embodiments, disclosed herein is a human antibody which includes a heavy chain including at least one CDR selected from the group of CDR sequences shown in FIGS. 1, 3, and 5.

In some embodiments, disclosed herein is an antibody which includes a light chain including at least one CDR selected from the group of CDR sequences shown in FIGS. 2, 4, and 6.

In some embodiments, disclosed herein is a human antibody which includes a heavy chain including one, two, or three CDR(s) selected from the group of CDR sequences shown in FIGS. 1, 3, and 5.

In some embodiments, disclosed herein is a human antibody which includes a light chain including one, two, or three CDR(s) selected from the group of CDR sequences shown in FIGS. 2, 4, and 6.

In some embodiments, disclosed herein is a human antibody, which includes a heavy chain including the sequence shown in FIG. 1, FIG. 3, or FIG. 5.

In some embodiments, disclosed herein is a human antibody includes a light chain including the sequence shown in FIG. 2, FIG. 4, or FIG. 6.

In some embodiments, disclosed herein is a human antibody, which includes a heavy chain including the sequence of FIG. 1 and a light chain sequence of FIG. 2.

In some embodiments, disclosed herein is a human antibody, which includes a heavy chain including the sequence of FIG. 3 and a light chain sequence of FIG. 4.

In some embodiments, disclosed herein is a human antibody, which includes a heavy chain including the sequence of FIG. 5 and a light chain sequence of FIG. 6.

In some embodiments, disclosed herein is an expression vector including any one of the nucleic acids shown in FIGS. 1-6.

In some embodiments, the method is performed using a FACS assay, a gel testing assay, a tube testing assay, or a solid phase testing assay.

BRIEF DESCRIPTION OF THE DRAWINGS

FIG. 1 shows the heavy chain sequence (SEQ ID NOs: 3, 4, and 5) of monoclonal antibodies Puma 1 and 2 directed to KEL1 (K). The shading indicates where the highly variable region begins. The CDR regions (CDR1: DYYMK, SEQ ID NO: 114; CDR2: DLNPNNGDTFYNQKFKG, SEQ ID NO: 115; CDR3: CAREAGSSFGSSCNYWG, SEQ ID NO: 116) of the heavy chain are underlined.

FIG. 2 shows the the light chain sequence (SEQ ID NOs: 7, 8, and 9) of monoclonal antibodies Puma 1 and 2 directed to KEL1 (K). The shading indicates where the highly variable region begins. The CDR regions (CDR1: KASQTVSKDVA, SEQ ID NO: 117; CDR2: YASNRYT, SEQ ID NO: 118; CDR3: QQDYSS, SEQ ID NO: 119) of the light chain are underlined.

FIG. 3 shows the heavy chain sequence (SEQ ID NOs: 10, 11, and 12) of monoclonal antibody Puma 3 directed to a common Kell epitope. The shading indicates where the highly variable region begins. The CDR regions (CDR1: SYGVY, SEQ ID NO: 120; CDR2: IIWGDG-STNYQSVLRS, SEQ ID NO: 121; CDR3: RGDYDVA, SEQ ID NO: 122) of the heavy chain are underlined.

FIG. 4 shows the light chain sequence (SEQ ID NOs: 14, 15, and 16) of monoclonal antibody Puma 3 directed to a common Kell epitope. The shading indicates where the highly variable region begins. The CDR regions (CDR1: KASQTVSEVGTSLMH, SEQ ID NO: 123; CDR2: RTSN-LEA, SEQ ID NO: 124; CDR3: QQS) of the light chain are underlined.

FIG. 5 shows the heavy chain sequence (SEQ ID NOs: 17, 18, and 19) of monoclonal antibody Puma 4 directed to KEL4 ($Kp^b$). The shading indicates where the highly variable region begins. The CDR regions (CDR1: NYWMN, SEQ ID NO: 125; CDR2: EIRLNSNNYATHYAESVKG, SEQ ID NO: 126; CDR3: NWDFAW, SEQ ID NO: 127) of the heavy chain are underlined.

FIG. 6 shows the light chain sequence (SEQ ID NOs: 20, 21, and 22) of monoclonal antibody Puma 4 directed to KEL4 ($Kp^b$). The shading indicates where the highly variable region begins. The CDR regions (CDR1: KASQDVSTVVA, SEQ ID NO: 128; CDR2: WASTRHT, SEQ ID NO: 129; CDR3: QQHYT, SEQ ID NO: 130) of the light chain are underlined.

FIG. 11 shows (A) the sequences of humanization of PUMA1 to human IgG1 (SEQ ID NO: 23), IgG2 (SEQ ID NO: 24), IgG3 (SEQ ID NO: 25), and IgG4 (SEQ ID NO: 26) and (B) the alignment of these sequences (SEQ ID NOs: 23-26).

FIG. 13 shows a general overview of how anti-human globulin (AHG) is used diagnostically in patients being screened for alloantibodies prior to transfusion.

Figure 17:
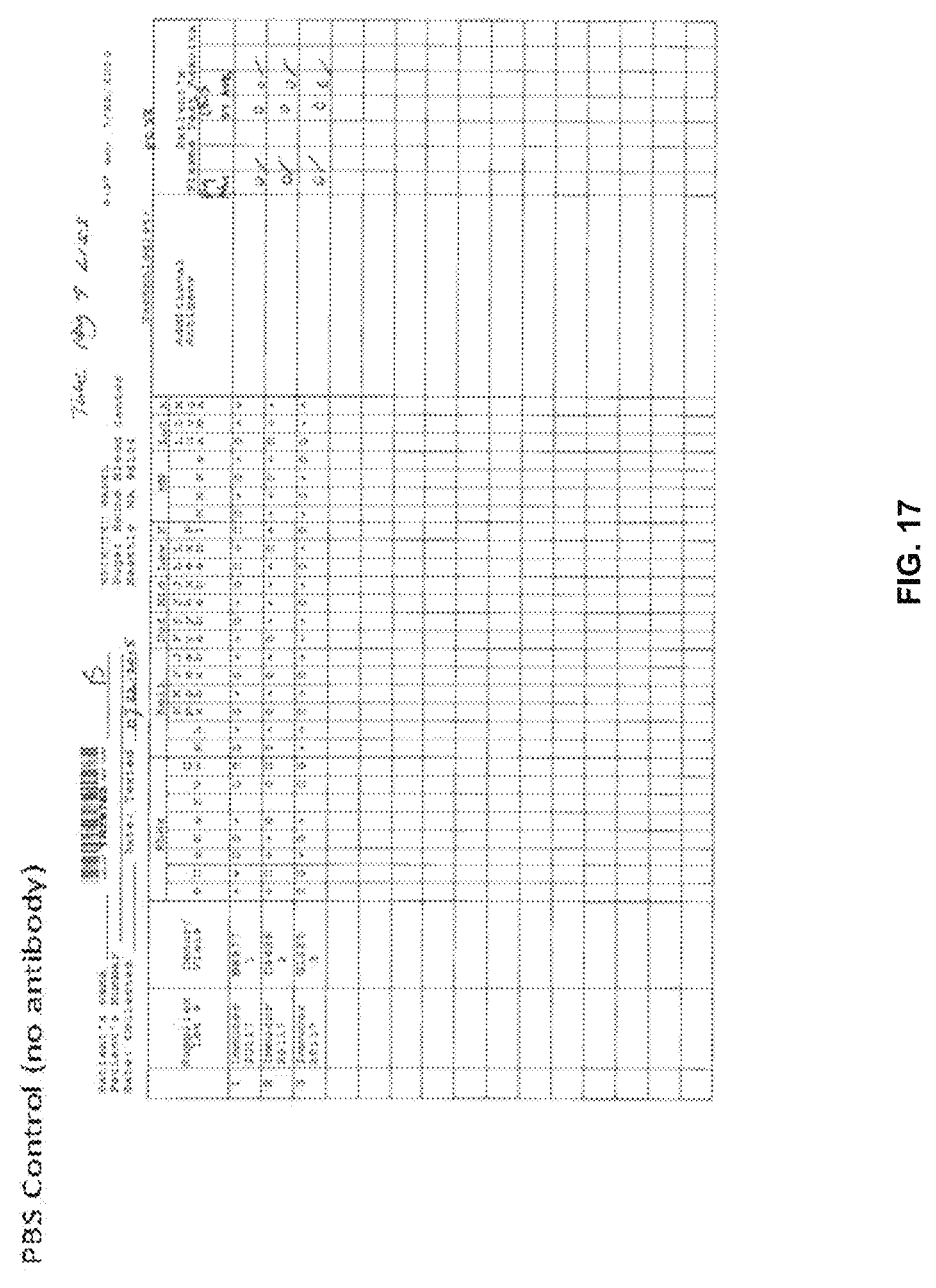

FIGS. 17-22 show the use of PUMA1 IgG1, IgG2, IgG3, and IgG4 to evaluate various anti-human globulin (AHG) preparations using a tube testing assay.

Figure 23:
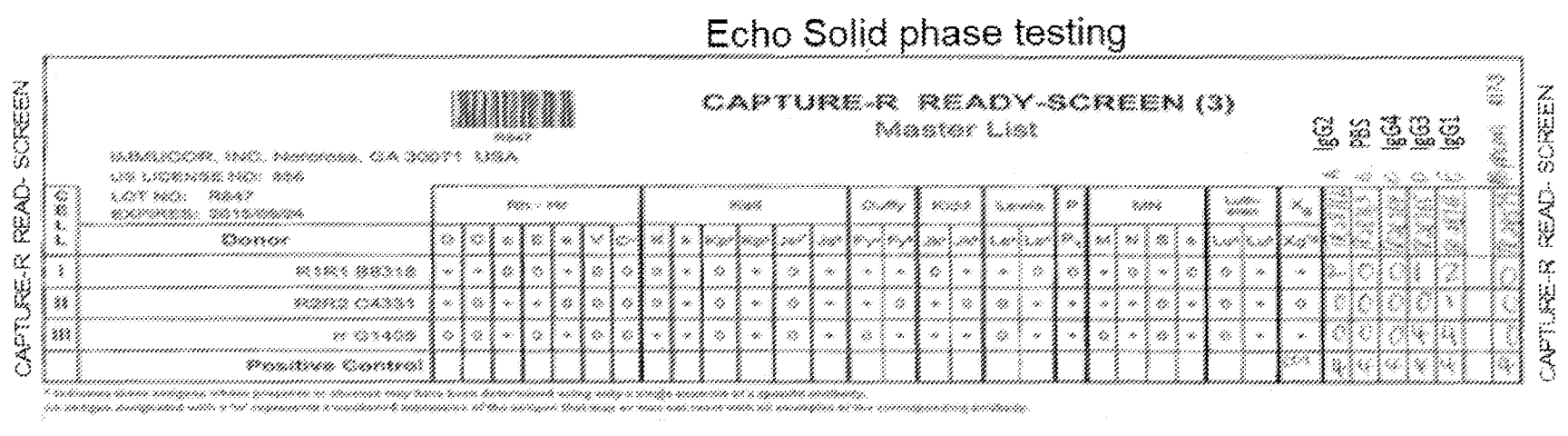

FIGS. 23-25 show the use of PUMA1 IgG1, IgG2, IgG3, and IgG4 to evaluate various anti-human globulin (AHG) preparations using a solid phase testing assay.

As shown in FIG. 26A, mouse RBCs were stained with PUMA1 antibody followed by secondary antibody (wild-type RBCs dotted line, K transgenic RBCs solid line). K transgenic RBCs were also stained with secondary antibody alone (dashed line). As shown in FIG. 26B, human RBCs with a K+k+ phenotype were stained with PUMA 1 followed by secondary antibody (solid line) or with secondary antibody alone (dashed line). RBCs with a K-k+ phenotype were stained with PUMA1 followed by secondary antibody (dotted line). FIG. 26C provides a diagram showing the general cloning and expression strategy.

FIG. 29 provides amino acid basis for variation amongst IgG isoallotypes. For each IgG subtype, the *01 designation is the canonical sequence. (SEQ ID NOs: 27-113).

DETAILED DESCRIPTION

Figure 7:
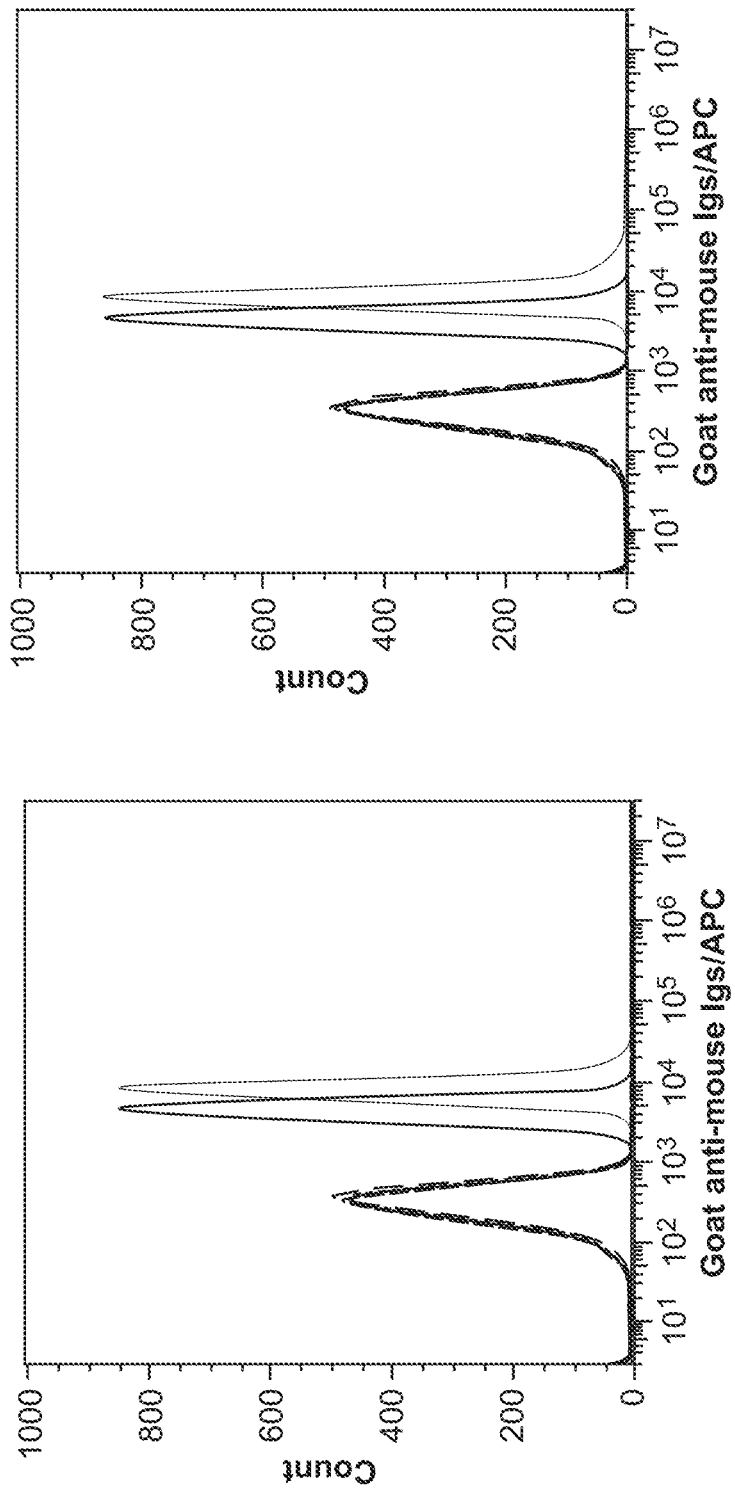
FIG. 7 shows the specificity of monoclonal antibody Puma 1.
Figure 8:
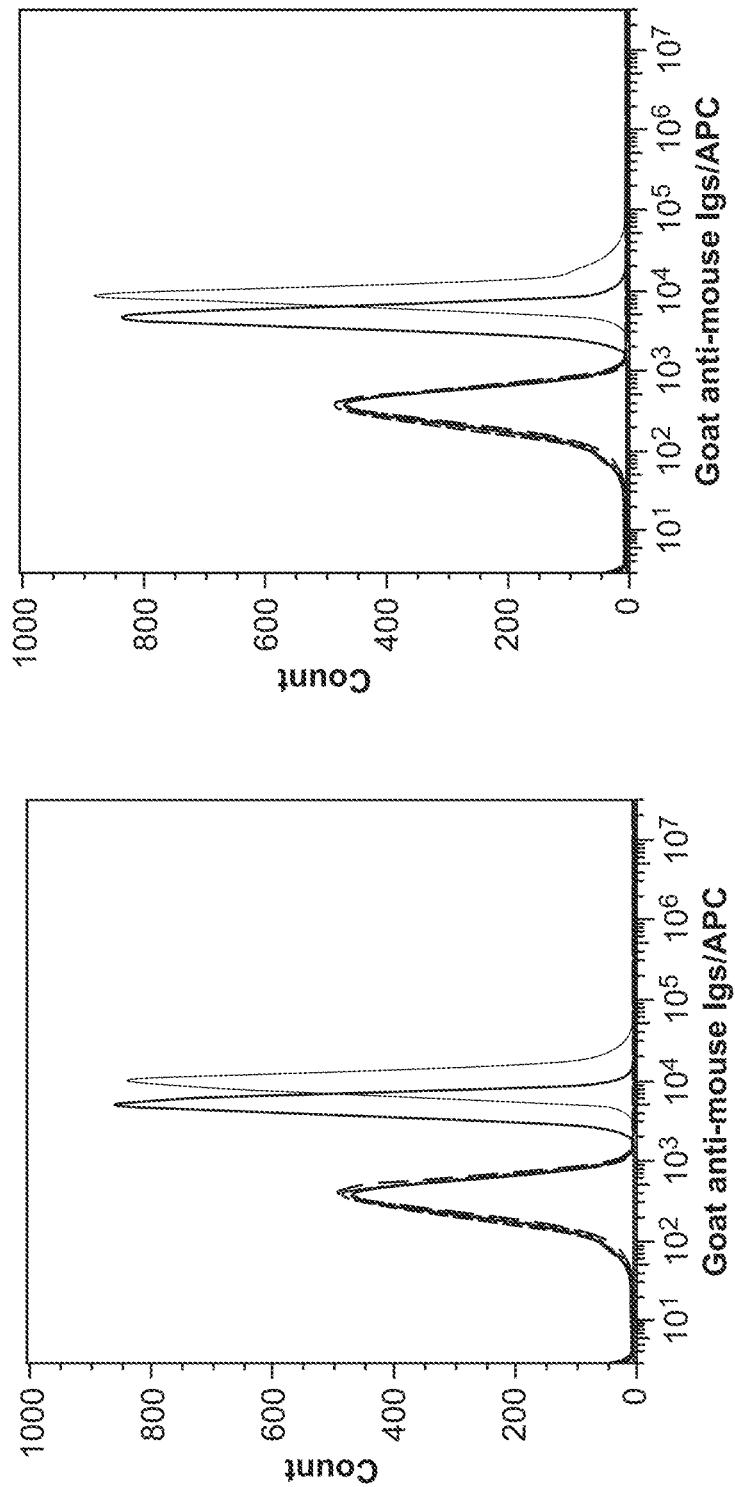
FIG. 8 shows the specificity of monoclonal antibody Puma 2.
Figure 9:
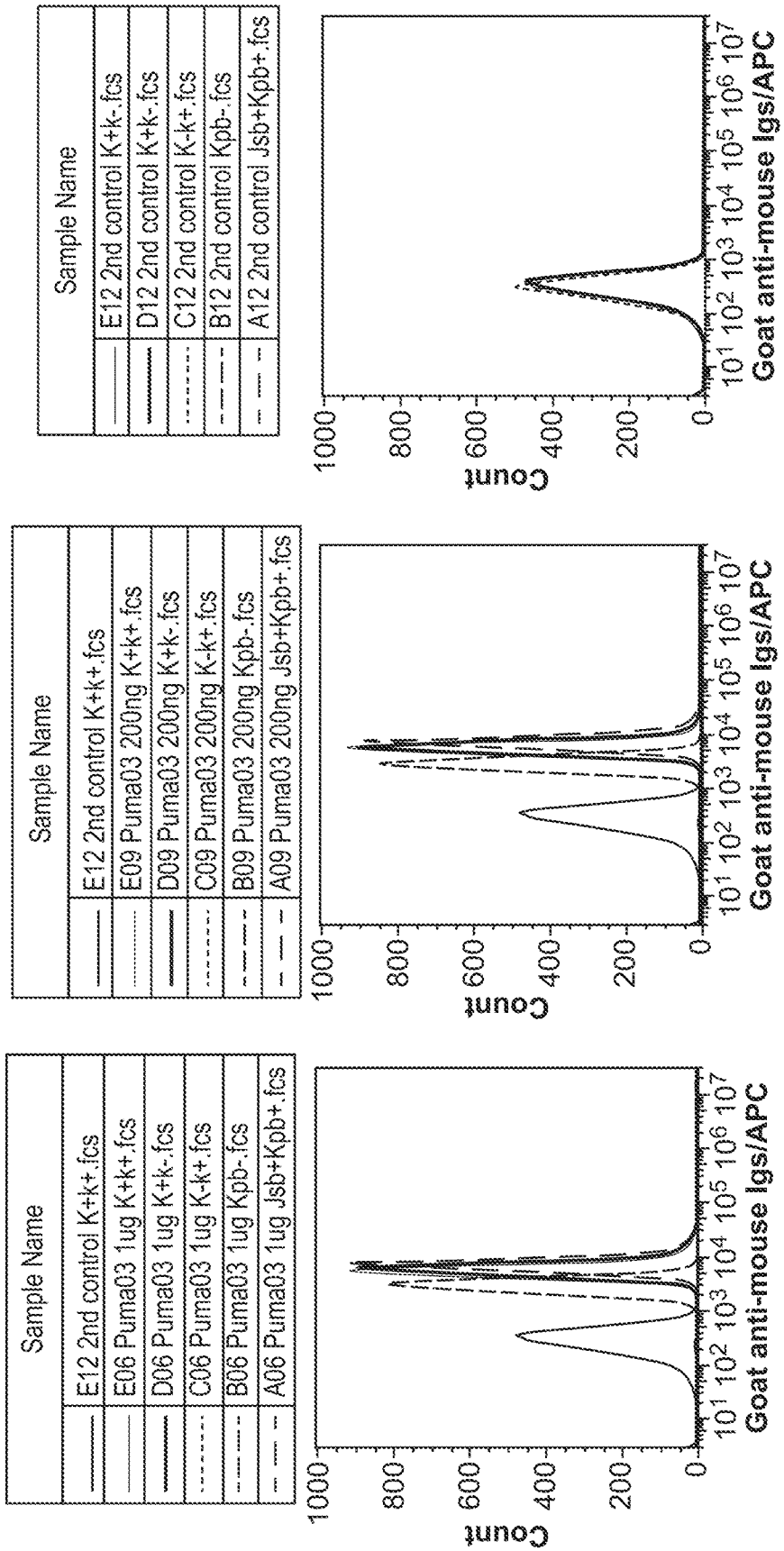
FIG. 9 shows the specificity of monoclonal antibody Puma 3.
Figure 10:
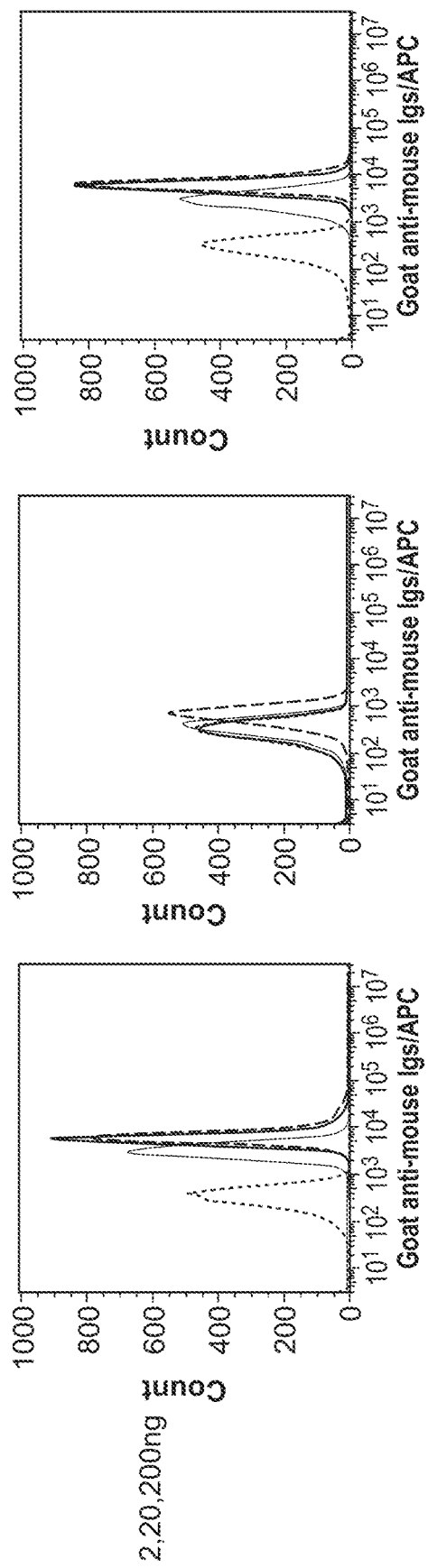
FIG. 10 shows the specificity of monoclonal antibody Puma 4.

Compositions and methods for determining the sensitivity and specificity of antibody detection reagents are provided herein.

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Certain ranges can be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. The term "about" as used herein when referring to a measurable value such as an amount, a temporal duration, and the like, is meant to encompass variations of ±20% or ±10%, such as ±5%, such as ±1%, and such as ±0.1% from the specified value, as such variations are appropriate to perform the disclosed methods.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided can be different from the actual publication dates which can need to be independently confirmed.

It is noted that, as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Additionally, certain embodiments of the disclosed devices and/or associated methods can be represented by drawings which can be included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

The current disclosure provides for isolating a monoclonal anti-RBC alloantibody against a common human RBC antigen (Kell), and cloning out the antigen binding domains of the antibody (both heavy and light chain). The isolated antibody is called PUMA1. The antigen binding domains of the heavy chain were then cloned upstream and in frame with the coding sequence for IgG1, IgG2, IgG3 and IgG4 human heavy chains. Expression vectors for these novel recombinant sequences were co-transfected (along with the light chain) into CHO cells, followed by purification of the recombinant antibodies (see FIG. 13). In this way, 4 different antibodies (of the different IgG subtypes) were purified to homogeneity and in the absence of IgGs of the other subtypes. Moreover, each PUMA1 IgG subtype binds to the same target epitope, allowing a standardization of affinities across each PUMA1 IgG subtype. Finally, since PUMA1 recognizes a common RBC alloantigen, this allows PUMA 1 IgG1-IgG4 to serve as standards in each of the existing RBC antibody detected platforms, so as to assess the ability of any given batch or preparation of AHG (polyclonal or monoclonal) to bind each human IgG subtypes and in different platforms.

Further refinement of this approach is the introduction of additional sequence variations in the IgG constant regions. Humans have multiple known variations in IgG constant regions (called allotypes if they constitute a new epitope). Additional variations have been described that are not known to generate epitopes, but nevertheless can change IgG structure. It is unclear the extent to which any given AHG will recognize any of these given sequence variants. By introducing these variants into the PUMA1 heavy chain vectors, a full panel of all known IgG subtypes (IgG1-IgG4), and all known variants, provides novel reagents that can serve as quality control and characterization diagnostics for AHG in any existing platform that screens patients for anti-RBC alloantibodies. As the particulars of any given testing platform can vary, AHG performances can vary.

Finally, this approach can be taken to make monoclonal PUMA1 of the IgM, IgA, IgE or IgD isotype, for standards to assess assays that use variants of AHG to detect these other isotypes.

Additional application of the techniques described above and, for example, with respect to isoallotypes below, extends to making novel antibodies (by the same general approach) so as to make reagents for testing of diagnostics ability to detect antibodies to platelets, white blood cells, other tissues (auto, allo and xeno), viruses, bacteria, fungi, parasites, vaccines, and purified antigens. As such, the subject methods include identifying and/or manufacturing such regents.

The subject aspects also include methods of manufacturing or otherwise producing any of the subject systems, kits, assays or components, e.g., reagents, thereof as well as methods of manufacturing or otherwise producing assays or components thereof which are operated according to any of the methods or method steps provided herein.

In the embodiments set forth herein, any one or more of the characteristics of the subject disclosure, e.g., methods, referring to IgG1, IgG2, IgG3, or IgG4 can also be applied in the same manner with respect to any of the 29 IgG isoallotypes alone or in combination. Furthermore, any one or more of the characteristics of the subject disclosure, e.g., methods, referring to IgG1, IgG2, IgG3, or IgG4 can also be applied in the same manner with respect to any subject, e.g., mammal, e.g., human, immunoglobulin component. As such, the subject disclosure includes assays for assessing characteristics of such components, such as their presence or absence from a panel, as set forth herein.

Human immunoglobulin components which can be applied according to the subject aspects include, for example, IgM, IgA1, IgA2, IgE or IgD, or any variants thereof. Human immunoglobulin components which can be applied according to the subject aspects also include, for example, anti-human leukocyte antigen (HLA) antibodies or one or more isotypes thereof, such as HLA-specific immunoglobulin G antibodies. Immunoglobulin components which can also be applied include hyperimmune immunoglobulins from human immunodeficiency virus (HIV)-infected persons (HIVIG). Animal immunoglobulin components can also be utilized according to the subject embodiments.

In some embodiments, a subject, such as a subject from which one or more samples or portions thereof, e.g., proteins are derived, is a "mammal" or a "mammalian" subject, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is a human. The term "humans" can include human subjects of both genders and at any stage of development (e.g., fetal, neonates, infant, juvenile, adolescent, and adult), where in certain embodiments the human subject is a juvenile, adolescent or adult. While the subject matter described herein can be applied in association with a human subject or one or more samples or aspects therefrom, it is to be understood that the subject matter can also be applied in association with other subjects, that is, on "non-human subjects."

Isoallotypes

As designated above, IgG exists in 4 different subtypes, IgG1, IgG2, IgG3, and IgG4. There is genetic variation within IgG subtypes. Such genetic variants within IgG subtypes are referred to as isoallotypes. There are at least 29 different isoallotypes, with 7, 4, 15, and 3 isoallotypes existing for IgG1, IgG2, IgG3, and IgG4, each respectively. The isoallotypes are referred to herein for each immunoglobulin by number and, in some cases, an additional designation such as "v2." A listing of the isoallotypes and their sequences is provided, for example, in FIG. 29. In various embodiments, the reactivity of anti-IgG with different isoallotypes is evaluated.

According to the subject embodiments, any one or more of the characteristics of the subject disclosure, e.g., methods, referring to IgG1, IgG2, IgG3, or IgG4 can also be applied in the same manner with respect to any of the 29 isoallotypes alone or in combination.

In various embodiments of the subject disclosure, a monoclonal anti-K antibody (PUMA1) was isolated, sequenced, and a panel of PUMA1 variants was expressed including the 29 known IgG isoallotypes. The resulting panel of antibodies was pre-incubated with K+ RBCs and was then subjected to testing with currently approved anti-IgG, by flow cytometry, solid phase systems, gel card, and tube testing.

In some aspects of the disclosure, an FDA approved monoclonal anti-IgG (Gammaclone) failed to recognize 2 out of 15 IgG3 isoallotypes (IgG3-03 and IgG3-13) and 3 out of 3 IgG4 isoallotypes (IgG4-01, 02, 03). Also, in some aspects of the subject disclosure, an FDA approved rabbit polyclonal anti-IgG recognized each of the known human IgG isoallotypes.

In some aspects of the subject embodiments, methods are provided that include, for example, determining the specificity and/or sensitivity of an anti-human globulin. The methods can include, for example, binding an anti-human globulin antibody to a panel of human antibodies of different subtype. Aspects of the methods also can include detecting the binding of the anti-human globulin to a subtype, such as IgG1, IgG2, IgG3, IgG4, or any one or more isoallotype of any of such immunoglobulins, and thus determining the specificity and sensitivity of an anti-human globulin.

The methods also include detecting and/or determining the absence of binding or coupling of the anti-human globulin to one or more subtype, such as IgG1, IgG2, IgG3, IgG4, or any one or more isoallotype of any of such immunoglobulins, such as any one or combination of the isoallotypes provided in FIG. 29. Such a method can be applied to identify "holes" in an assay where such an assay would not produce a useful result.

Figure 27:
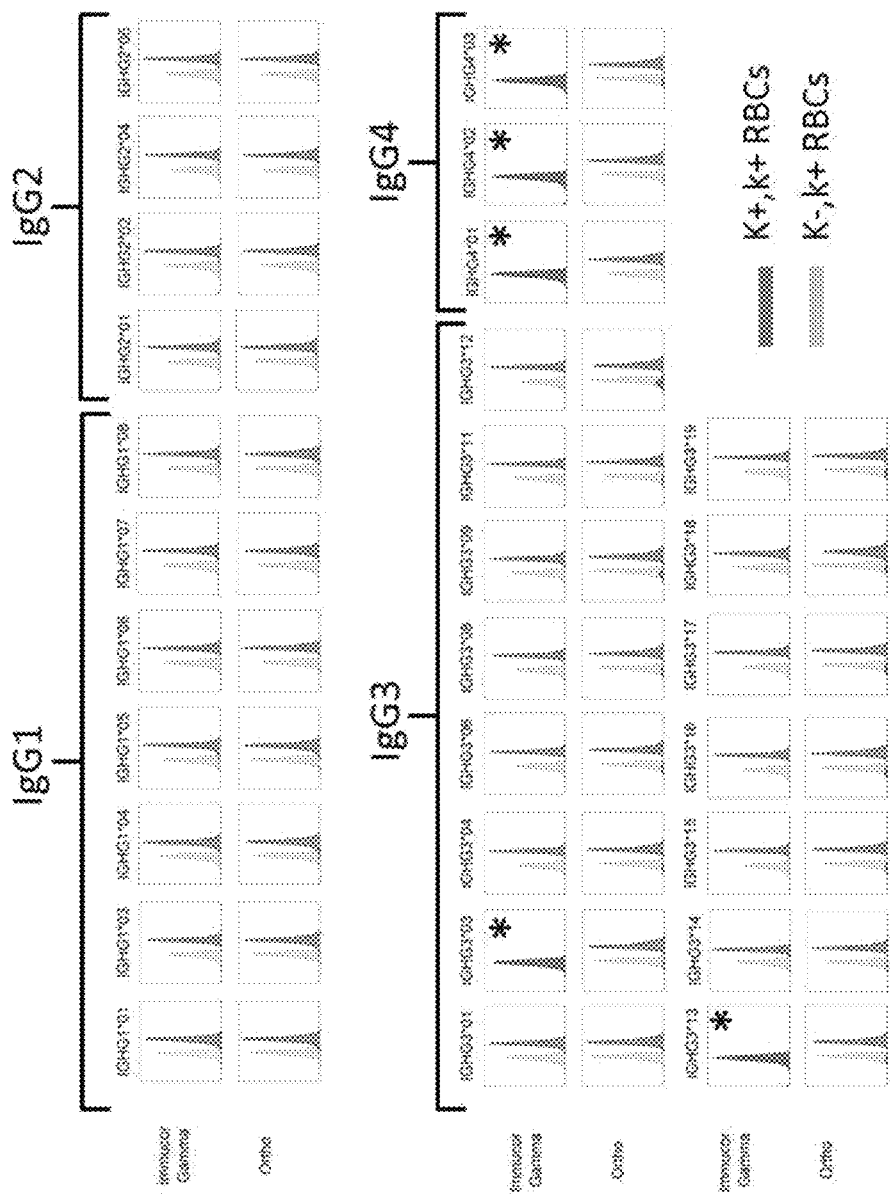
FIG. 27 provides data obtained when K+k+ RBCs were incubated with each of the indicated PUMA1 IgG isoallotype, followed by the test anti-IgG and relevant detection reagent (see methods) [dark(er) gray histograms]. K-k+ RBCs were also incubated with each IgG isoallotype as a background control [light(er) gray histograms]. Isoallotypes that were not recognized are indicated by (*).

Various embodiments of the subject disclosure include detecting one or more, such as all, of the 29 isoallotypes of human IgG provided in FIG. 29 using polyclonal antibodies, e.g., anti-IgG. In various embodiments, the methods include detecting shortcomings in one or more assays, such as assays applying monoclonal anti-IgG as described herein. As such, the methods also include detecting the absence of one or more of the 29 isoallotypes of human IgG provided in FIG. 29 from a panel using monoclonal antibodies, e.g., anti-IgG. In such aspects, monoclonal anti-IgG does not bind to all of the 29 isoallotypes, e.g., only binds to less than the 29 isoallotypes, such as 24 out of 29 isoallotypes. In variations of the methods, the monoclonal anti-IgG assay can fail to recognize IgG3-03, IgG3-13, IgG4-01, IgG4-02, and IgG4-03 (see FIG. 27) and the methods include detecting each failed recognition.

In FIG. 29, amino acid variations among IgG subclasses and their respective isoallotypes are shown along the top, broken up by the region in which the mutation occurs (CH1, hinge, CH2 or CH3; labeled in dark grey) as well as by those variations that occur only between subclasses themselves (amino acid residue not highlighted) or variations that define the isoallotypes (amino acid position highlighted with darkened shade of grey). Specific changes within an IgG subclass are shown as underlined. While all of the IgG1, IgG2, and IgG4 isoallotypes have their own hinge regions, these do not change in their respective variants. However, the IgG3 hinge is variable among isoallotypes; with the presence or absence of specific hinge sequences shown in the table provided in FIG. 29. The ability of each isoallotype to be recognized by each of the tested anti-IgG reagents is indicated with a + or on the right side of the table. (EU numbering scheme used for amino acid position.) For each IgG subtype, the *01 designation is the canonical sequence. Furthermore, as provided in FIG. 29, IGHG1*01v2 is equivalent to IGHG1*05 and IGHG1*04v2 is equivalent to IGHG1*06.

Polypeptides

The term "polypeptide" or "peptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "isolated protein," "isolated polypeptide," or "isolated peptide" is a protein, polypeptide or peptide that by virtue of its origin or source of derivation (1) is not associated with naturally associated components that accompany it in its native state, (2) is free of other proteins from the same species, (3) is expressed by a cell from a different species, or (4) does not occur in nature. Thus, a peptide that is chemically synthesized or synthesized in a cellular system different from the cell from which it naturally originates will be "isolated" from its naturally associated components. A protein can also be rendered substantially free of naturally associated components by isolation, using protein purification techniques well known in the art.

The terms "polypeptide", "protein", "peptide," "antigen," or "antibody" within the meaning of the present invention, includes variants, analogs, orthologs, homologs and derivatives, and fragments thereof that exhibit a biological activity, generally in the context of being able to induce an immune response in a subject, or bind an antigen in the case of an antibody.

The polypeptides of the invention include an amino acid sequence derived from Kell system antigens or fragments thereof, corresponding to the amino acid sequence of a naturally occurring protein or corresponding to variant protein, i.e., the amino acid sequence of the naturally occurring protein in which a small number of amino acids have been substituted, added, or deleted but which retains essentially the same immunological properties. In addition, such derived portion can be further modified by amino acids, especially at the N- and C-terminal ends to allow the polypeptide or fragment to be conformationally constrained and/or to allow coupling to an immunogenic carrier after appropriate chemistry has been carried out. The polypeptides of the present invention encompass functionally active variant polypeptides derived from the amino acid sequence of Kell system antigens in which amino acids have been deleted, inserted, or substituted without essentially detracting from the immunological properties thereof, i.e. such functionally active variant polypeptides retain a substantial peptide biological activity.

In one embodiment, such functionally active variant polypeptides exhibit at least 60%, 65%, 70%, 75%, 80%, 81%, 82%, 83%, 84%, 85%, 86%, 87%, 88%, 89% 90%, 91%, 92%, 93%, 94%, 95%, 96%, 97%, 98%, or 99% identity to an amino acid sequence of the blood group antigens disclosed herein. Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). An alternative algorithm when comparing a sequence of the invention to a database containing a large number of sequences from different organisms is the computer program BLAST, especially blastp or tblastn, using default parameters. See, e.g., Altschul et al., J. Mol. Biol. 215:403-410 (1990); Altschul et al., Nucleic Acids Res. 25:3389-402 (1997).

Functionally active variants include naturally occurring functionally active variants such as allelic variants and species variants and non-naturally occurring functionally active variants that can be produced by, for example, mutagenesis techniques or by direct synthesis.

A functionally active variant can exhibit, for example, at least 60%, 65%, 70%, 75%, 80%, 81%, 82%, 83%, 84%, 85%, 86%, 87%, 88%, 89% 90%, 91%, 92%, 93%, 94%, 95%, 96%, 97%, 98%, or 99% identity to an amino acid sequence of a Kell system or other antigen disclosed herein, and yet retain a biological activity. Where this comparison requires alignment, the sequences are aligned for maximum homology. The site of variation can occur anywhere in the sequence, as long as the biological activity is substantially similar to the Kell system or other antigens disclosed herein, e.g., ability to induce a tolerance response. Guidance concerning how to make phenotypically silent amino acid substitutions is provided in Bowie et al., Science, 247: 1306-1310 (1990), which teaches that there are two main strategies for studying the tolerance of an amino acid sequence to change. The first strategy exploits the tolerance of amino acid substitutions by natural selection during the process of evolution. By comparing amino acid sequences in different species, the amino acid positions which have been conserved between species can be identified. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific immunogenic activity of the modified polypeptide.

The second strategy uses genetic engineering to introduce amino acid changes at specific positions of a cloned gene to identify regions critical for protein function. For example, site-directed mutagenesis or alanine-scanning mutagenesis can be used (Cunningham et al., Science, 244: 1081-1085 (1989)). The resulting variant polypeptides can then be tested for specific biological activity.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein is well known to those skilled in the art. (See, e. g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)).

Mutations can also be introduced using commercially available kits such as "QuikChange Site-Directed Mutagenesis Kit" (Stratagene) or directly by peptide synthesis. The generation of a functionally active variant to an peptide by replacing an amino acid which does not significantly influence the function of said peptide can be accomplished by one skilled in the art.

A type of amino acid substitution that can be made in the polypeptides of the invention is a conservative amino acid substitution. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity can be adjusted upwards to correct for the conservative nature of the substitution. Means for making this adjustment are well-known to those of skill in the art. See e.g. Pearson, Methods Mol. Biol. 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Various conservative amino acids substitution groups include: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., Science 256:1443-45 (1992). A "moderately conservative" replacement is any change having a nonnegative value in the PAM250 log-likelihood matrix.

A functionally active variant can also be isolated using a hybridization technique. Briefly, DNA having a high homology to the whole or part of a nucleic acid sequence encoding the peptide, polypeptide or protein of interest, e.g. Kell system antigens, is used to prepare a functionally active peptide. Therefore, a polypeptide of the invention also includes entities which are functionally equivalent and which are encoded by a nucleic acid molecule which hybridizes with a nucleic acid encoding any one of the Kell system antigens or a complement thereof. One of skill in the art can easily determine nucleic acid sequences that encode peptides of the invention using readily available codon tables. As such, these nucleic acid sequences are not presented herein.

Nucleic acid molecules encoding a functionally active variant can also be isolated by a gene amplification method such as PCR using a portion of a nucleic acid molecule DNA encoding a peptide, polypeptide, protein, antigen, or antibody of interest, e.g. Kell system antigens, as the probe.

For the purpose of the present invention, it should be considered that several polypeptides or antigens of the invention can be used in combination. All types of possible combinations can be envisioned. The same sequence can be used in several copies on the same polypeptide molecule, or wherein peptides of different amino acid sequences are used on the same polypeptide molecule; the different peptides or copies can be directly fused to each other or spaced by appropriate linkers. As used herein the term "multimerized (poly)peptide" refers to both types of combination wherein polypeptides of either different or the same amino acid sequence are present on a single polypeptide molecule. From 2 to about 20 identical and/or different peptides can be thus present on a single multimerized polypeptide molecule.

In one embodiment of the invention, a peptide, polypeptide, protein, or antigen of the invention is derived from a natural source and isolated from a bacterial source. A peptide, polypeptide, protein, or antigen of the invention can thus be isolated from sources using standard protein purification techniques.

Alternatively, peptides, polypeptides and proteins of the invention can be synthesized chemically or produced using recombinant DNA techniques. For example, a peptide, polypeptide, or protein of the invention can be synthesized by solid phase procedures well known in the art. Suitable syntheses can be performed by utilising "T-boc" or "F-moc" procedures. Cyclic peptides can be synthesized by the solid phase procedure employing the well-known "F-moc" procedure and polyamide resin in the fully automated apparatus. Alternatively, those skilled in the art will know the necessary laboratory procedures to perform the process manually. Techniques and procedures for solid phase synthesis are described in ' Solid Phase Peptide Synthesis: A Practical Approach' by E. Atherton and R. C. Sheppard, published by IRL at Oxford University Press (1989) and 'Methods in Molecular Biology, Vol. 35: Peptide Synthesis Protocols (ed. M. W. Pennington and B. M. Dunn), chapter 7, pp 91-171 by D. Andreau et al.

Alternatively, a polynucleotide encoding a peptide, polypeptide or protein of the invention can be introduced into an expression vector that can be expressed in a suitable expression system using techniques well known in the art, followed by isolation or purification of the expressed peptide, polypeptide, or protein of interest. A variety of bacterial, yeast, plant, mammalian, and insect expression systems are available in the art and any such expression system can be used. Optionally, a polynucleotide encoding a peptide, polypeptide or protein of the invention can be translated in a cell-free translation system.

Nucleic acid sequences corresponding to Kell system antigens can also be used to design oligonucleotide probes and used to screen genomic or cDNA libraries for genes encoding other variants or from other species. The basic strategies for preparing oligonucleotide probes and DNA libraries, as well as their screening by nucleic acid hybridization, are well known to those of ordinary skill in the art. See, e.g., DNA Cloning: Vol. I, supra; Nucleic Acid Hybridization, supra; Oligonucleotide Synthesis, supra; Sambrook et al., supra. Once a clone from the screened library has been identified by positive hybridization, it can be confirmed by restriction enzyme analysis and DNA sequencing that the particular library insert contains a Kell system antigen gene, or a homolog thereof. The genes can then be further isolated using standard techniques and, if desired, PCR approaches or restriction enzymes employed to delete portions of the full-length sequence.

Alternatively, DNA sequences encoding the proteins of interest can be prepared synthetically rather than cloned. The DNA sequences can be designed with the appropriate codons for the particular amino acid sequence. In general, one will select codons for the intended host if the sequence will be used for expression. The complete sequence is assembled from overlapping oligonucleotides prepared by standard methods and assembled into a complete coding sequence. See, e.g., Edge (1981) *Nature* 292: 756; Nambair et al. (1984) *Science* 223: 1299; Jay et al. (1984) *J. Biol. Chem.* 259: 6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pUC1 (*Streptomyces*), pUC6 (*Streptomyces*), YIp5 (*Saccharomyces*), YCp19 (*Saccharomyces*) and bovine papilloma virus (mammalian cells). See, Sambrook et al., supra; DNA Cloning, supra; B. Perbal, supra. The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence can or cannot contain a signal peptide or leader sequence. Leader sequences can be removed by the host in post-translational processing. See, e.g., U.S. Pat. Nos. 4,431,739; 4,425,437; 4,338,397. Examples of vectors include pET32a(+) and pcDNA3002Neo.

Other regulatory sequences can also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements can also be present in the vector, for example, enhancer sequences.

The control sequences and other regulatory sequences can be ligated to the coding sequence prior to insertion into a vector, such as the cloning vectors described above. Alternatively, the coding sequence can be cloned directly into an expression vector which already contains the control sequences and an appropriate restriction site.

In some cases it can be necessary to modify the coding sequence so that it can be attached to the control sequences with the appropriate orientation; i.e., to maintain the proper reading frame. It can also be desirable to produce mutants or analogs of the protein. Mutants or analogs can be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; DNA Cloning, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, HEK293F cells, NSO-1 cells, as well as others. Similarly, bacterial hosts such as *E. coli*, *Bacillus subtilis*, and *Streptococcus* spp., will find use with the present expression constructs. Yeast hosts useful in the present invention include, but are not limited to, *Saccharomyces cerevisiae*, *Candida albicans*, *Candida maltosa*, *Hansenula polymorpha*, *Kluyveromyces fragilis*, *Kluyveromyces lactis*, *Pichia guillerimondii*, *Pichia pastoris*, *Schizosaccharomyces pombe* and *Yarrowia lipolytica*. Insect cells for use with baculovirus expression vectors include, but are not limited to, *Aedes aegypti*, *Autographa californica*, *Bombyx mori*, *Drosophila melanogaster*, *Spodoptera frugiperda*, and *Trichoplusia ni*.

Depending on the expression system and host selected, the proteins of the present invention are produced by culturing host cells transformed by an expression vector described above under conditions whereby the protein of interest is expressed. The protein is then isolated from the host cells and purified. The selection of the appropriate growth conditions and recovery methods are within the skill of the art.

Kell system antigen protein sequences can also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3-254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis. Chemical synthesis of peptides can be performed if a small fragment of the antigen in question is capable of raising an immunological response in the subject of interest.

Polypeptides of the invention can also include those that arise as a result of the existence of multiple genes, alternative transcription events, alternative RNA splicing events, and alternative translational and postranslational events. A polypeptide can be expressed in systems, e.g. cultured cells, which result in substantially the same postranslational modifications present as when the peptide is expressed in a native cell, or in systems that result in the alteration or omission of postranslational modifications, e.g. glycosylation or cleavage, present when expressed in a native cell.

A peptide, polypeptide, protein, or antigen of the invention can be produced as a fusion protein that contains other distinct amino acid sequences that are not part of the Kell system antigen sequences disclosed herein, such as amino acid linkers or signal sequences or immunogenic carriers, as well as ligands useful in protein purification, such as glutathione-S-transferase, histidine tag, and staphylococcal protein A. More than one polypeptide of the invention can be present in a fusion protein. The heterologous polypeptide can be fused, for example, to the N-terminus or C-terminus of the peptide, polypeptide or protein of the invention. A peptide, polypeptide, protein, or antigen of the invention can also be produced as fusion proteins including homologous amino acid sequences.

Blood Group Antigen Proteins

Any of a variety of cell surface proteins found on red blood cells can be used in the practice of the present invention. In one embodiment, the proteins are blood group antigens, such as the Kell system antigens. Information on such antigens and, in particular, soluble forms are available in the art, for example, in Ridgwell et al., Transfusion Medicine, 17: 384-394 (2007).

Kell (CD238) is a clinically important human blood group antigen system including 28 antigens (Daniels et al., 2007, International Society of Blood Transfusion Committee on Terminology for Red Cell Surface Antigens: Cape Town report. Vox Sanguinis, 92, 250-253). The Kell antigens are carried by a single pass type II (cytoplasmic N-terminus) red blood cell membrane glycoprotein. The Kell glycoprotein is expressed in red cells and haematopoietic tissue (bone marrow and foetal liver) and to a lesser extent in other tissues, including brain, lymphoid organs, heart and skeletal muscle (Russo et al., 2000, Blood, 96, 340-346). The K/k (KEL1/KEL2) blood group antigen polymorphism is determined by a single nucleotide polymorphism (SNP) resulting in the presence of methionine (M) or threonine (T), respectively, at amino acid 193 of the extracellular C-terminal domain (Lee, 1997, Vox Sanguinis, 73, 1-11). The other mostclinically significant antithetical antigens $Kp^a/Kp^b$ (KEL3/KEL4) and $Js^a/Js^b$ (KEL6/KEL7) are also the result of SNPs resulting in single amino acid changes in the extracellular domain (Lee, 1997, Vox Sanguinis, 73, 1-11).

Kell system antibodies are known to cause haemolytic transfusion reactions and haemolytic disease of the fetus and newborn (HDFN). Kell-related HDFN may be because of suppression of fetal erythropoiesis in addition to immune destruction of red blood cells as in most other cases of HDFN (Vaughan et al., 1998, New England Journal of Medicine, 338, 798-803; Daniels et al., 2003, Transfusion, 43, 115-116). Anti-K (KEL1) is the most commonly encountered immune red cell antibody outside the ABO and Rh systems, and other antigens of the Kell blood group system, e.g. k (KEL2), $Kp^a$ (KEL3), $Kp^b$ (KEL4), $Js^a$ (KEL6) and $Js^b$ (KEL7) are also capable of stimulating the production of haemolytic antibodies and causing HDFN (Daniels, 2002, Human Blood Groups (2nd edn). Blackwell, Oxford).

The Duffy (Fy, CD234) blood group antigens are carried by a type III membrane glycoprotein, which is predicted to span the membrane seven times with a glycosylated extracellular N-terminus and a cytoplasmic C-terminus. It is expressed in red blood cells, vascular endothelial cells and a wide range of other tissues including kidney, lung, liver, spleen, brain (Iwamoto et al., 1996, Blood, 87, 378-385) and colon (Chaudhuri et al., 1997, Blood, 89, 701-712). The $Fy^a/Fy^b$ (FY1/FY2) blood group polymorphism is determined by an SNP resulting in the presence of glycine (G) or aspartic acid (D), respectively, at amino acid 42 in the N-terminal extracellular domain (Iwamoto et al., 1995, Blood, 85, 622-626; Mallinson et al., 1995, British Journal of Haematology, 90, 823-82; Tournamille et al., 1995, Human Genetics, 95, 407-410). Duffy blood group system antibodies can cause haemolytic transfusion reactions (Boyland et al., 1982, Transfusion, 22, 402; Sosler et al., 1989, Transfusion, 29, 505-507) and HDFN (Vescio et al., 1987, Transfusion, 27, 366; Goodrick et al., 1997, Transfusion Medicine, 7, 301-304).

The Lutheran (Lu, B-CAM, CD239) blood group antigens are carried by two single-pass type I (cytoplasmic C-terminus) membrane glycoproteins, which differ in the length of their cytoplasmic domains [the B-CAM glycoprotein has a shorter C-terminal cytoplasmic tail than Lu (Campbell et al., 1994, Cancer Research, 54, 5761-5765)]. The Lu glycoprotein has five extracellular immunoglobulin-like domains and is a member of the immunoglobulin gene superfamily (IgSF) (Parsons et al., 1995, Proceedings of the National Academy of Science of the United States of America, 92, 5496-5500) and is expressed in red blood cells and a wide range of other tissues (Reid & Lomas-Francis, 2004, The Blood Group Antigens Factsbook (2nd edn). Academic Press, London). The $Lu^a/Lu^b$ (LU1/LU2) blood group antigen polymorphism is determined by a SNP resulting in the presence of histidine (H) or arginine (R), respectively, at amino acid 77 of the first predicted N-terminal IgSF domain (El Nemer et al., 1997). Lutheran blood group system antibodies have been reported to be involved in mild delayed haemolytic transfusion reactions (Daniels, 2002, Human Blood Groups (2nd edn). Blackwell, Oxford) but are rarely involved in HDFN (Inderbitzen et al., 1982, Transfusion, 22, 542).

Antibodies

As used herein, the term "antibody" refers to any immunoglobulin or intact molecule as well as to fragments thereof that bind to a specific epitope. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term, including IgA, IgD, IgE, IgG, and IgM.

As used herein, the term "antibody fragment" refers specifically to an incomplete or isolated portion of the full sequence of the antibody which retains the antigen binding function of the parent antibody. Examples of antibody fragments include Fab, Fab', F(ab')2, and Fv fragments; diabodies; linear antibodies; single-chain antibody molecules; and multispecific antibodies formed from antibody fragments.

An intact "antibody" includes at least two heavy (H) chains and two light (L) chains inter-connected by disulfide bonds. Each heavy chain is composed of a heavy chain variable region (abbreviated herein as HCVR or $V_H$) and a heavy chain constant region. The heavy chain constant region is composed of three domains, $CH_1$, $CH_2$ and $CH_3$. Each light chain is composed of a light chain variable region (abbreviated herein as LCVR or $V_L$) and a light chain constant region. The light chain constant region is composed of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a VH domain; and (vi) an isolated complementarity determining region (CDR).

As used herein, the term "single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments and can be prepared by recombinant techniques or enzymatic or chemical cleavage of intact antibodies.

As used herein, the term "human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT App. Pub. Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

Also, recombinant immunoglobulins can be produced. See, Cabilly, U.S. Pat. No. 4,816,567, incorporated herein by reference in its entirety and for all purposes; and Queen et al., Proc Natl Acad Sci USA, 86:10029-10033 (1989).

As used herein, the term "monoclonal antibody" refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one aspect, the human monoclonal antibodies are produced by a hybridoma which includes a B cell obtained from a transgenic non-human animal, e.g., a transgenic mouse, having a genome including a human heavy chain transgene and a light chain transgene fused to an immortalized cell.

As used herein, the term "antigen" refers to a substance that prompts the generation of antibodies and can cause an immune response. It can be used interchangeably in the present disclosure with the term "immunogen". In the strict sense, immunogens are those substances that elicit a response from the immune system, whereas antigens are defined as substances that bind to specific antibodies. An antigen or fragment thereof can be a molecule (i.e., an epitope) that makes contact with a particular antibody. When a protein or a fragment of a protein is used to immunize a host animal, numerous regions of the protein can induce the production of antibodies (i.e., elicit the immune response), which bind specifically to the antigen (given regions or three-dimensional structures on the protein).

An "epitope" refers to the portion of the antigen bound by an antibody. Antigens can include multiple epitopes. Where the antigen is a protein, linear epitopes can range from about 5 to 20 amino acids in length. Antibodies can also recognize conformational determinants formed by non-contiguous residues on an antigen, and an epitope can therefore require a larger fragment of the antigen to be present for binding, e.g. a protein domain, or substantially all of a protein sequence. It will therefore be appreciated that a protein, which can be several hundred amino acids in length, can include a number of distinct epitopes.

As used herein, the term "humanized antibody," refers to at least one antibody molecule in which the amino acid sequence in the non-antigen binding regions and/or the antigen-binding regions has been altered so that the antibody more closely resembles a human antibody, and still retains its original binding ability.

In addition, techniques developed for the production of "chimeric antibodies" (Morrison, et al., Proc Natl Acad Sci, 81:6851-6855 (1984), incorporated herein by reference in their entirety) by splicing the genes from a mouse antibody molecule of appropriate antigen specificity together with genes from a human antibody molecule of appropriate biological activity can be used. For example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region.

In addition, techniques have been developed for the production of humanized antibodies (see, e.g., U.S. Pat. Nos. 5,585,089 and 5,225,539, which are incorporated herein by reference in their entirety). An immunoglobulin light or heavy chain variable region consists of a "framework" region interrupted by three hypervariable regions, referred to as complementarity determining regions (CDRs). Briefly, humanized antibodies are antibody molecules from non-human species having one or more CDRs from the non-human species and a framework region from a human immunoglobulin molecule.

Alternatively, techniques described for the production of single chain antibodies can be adapted to produce single chain antibodies against an immunogenic conjugate of the present disclosure. Single chain antibodies are formed by linking the heavy and light chain fragments of the Fv region via an amino acid bridge, resulting in a single chain polypeptide. Fab and F(ab')2 portions of antibody molecules can be prepared by the proteolytic reaction of papain and pepsin, respectively, on substantially intact antibody molecules by methods that are well-known. See e.g., U.S. Pat. No. 4,342,566. Fab' antibody molecule portions are also well-known and are produced from F(ab')2 portions followed by reduction of the disulfide bonds linking the two heavy chain portions as with mercaptoethanol, and followed by alkylation of the resulting protein mercaptan with a reagent such as iodoacetamide.

Antibody Assays

A number of screening assays are known in the art for assaying antibodies of interest to confirm their specificity and affinity and to determine whether those antibodies cross-react with other proteins.

The terms "specific binding" or "specifically binding" refer to the interaction between the antigen and their corresponding antibodies. The interaction is dependent upon the presence of a particular structure of the protein recognized by the binding molecule (i.e., the antigen or epitope). In order for binding to be specific, it should involve antibody binding of the epitope(s) of interest and not background antigens.

Once antibodies are produced, they are assayed to confirm that they are specific for the antigen of interest and to determine whether they exhibit any cross reactivity with other antigens. One method of conducting such assays is a sera screen assay as described in U.S. App. Pub. No. 2004/0126829, the contents of which are hereby expressly incorporated herein by reference. However, other methods of assaying for quality control are within the skill of a person of ordinary skill in the art and therefore are also within the scope of the present disclosure.

Antibodies, or antigen-binding fragments, variants or derivatives thereof of the present disclosure can also be described or specified in terms of their binding affinity to an antigen. The affinity of an antibody for an antigen can be determined experimentally using any suitable method. (See, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) can be made with standardized solutions of antibody and antigen, and a standardized buffer.

The affinity binding constant ($K_{aff}$) can be determined using the following formula:

$$K_{aff} = \frac{(n-1)}{2(n[mAb']_t = [mAb]_t)}$$

in which:

$$n = \frac{[mAg]_t}{[mAg']_t}$$

[mAb] is the concentration of free antigen sites, and [mAg] is the concentration of free monoclonal binding sites as determined at two different antigen concentrations (i.e., $[mAg]_t$ and $[mAg]_t$) (Beatty et al., J Imm Meth, 100:173-179 (1987)).

The term "high affinity" for an antibody refers to an equilibrium association constant ($K_{aff}$) of at least about $1 \times 10^7$ liters/mole, or at least about $1 \times 10^8$ liters/mole, or at least about $1 \times 10^9$ liters/mole, or at least about $1 \times 10^{10}$ liters/mole, or at least about $1 \times 10^{11}$ liters/mole, or at least about $1 \times 10^{12}$ liters/mole, or at least about $1 \times 10^{13}$ liters/mole, or at least about $1 \times 10^{14}$ liters/mole or greater. "High affinity" binding can vary for antibody isotypes. $K_D$, the equilibrium dissociation constant, is a term that is also used to describe antibody affinity and is the inverse of $K_{aff}$.

$K_D$, the equilibrium dissociation constant, is a term that is also used to describe antibody affinity and is the inverse of $K_{aff}$. If $K_D$ is used, the term "high affinity" for an antibody refers to an equilibrium dissociation constant ($K_D$) of less than about $1 \times 10^{-7}$ mole/liters, or less than about $1 \times 10^{-8}$ mole/liters, or less than about $1 \times 10^{-9}$ mole/liters, or less than about $1 \times 10^{-10}$ mole/liters, or less than about $1 \times 10^{-11}$ mole/liters, or less than about $1 \times 10^{-12}$ mole/liters, or less than about $1 \times 10^{-13}$ mole/liters, or less than about $1 \times 10^{-14}$ mole/liters or lower.

The immunoglobulin molecules of the present invention can be of any type (e.g., IgG, IgE, IgM, IgD, IgA and IgY), class (e.g., IgG1, IgG2, IgG3, IgG4, IgA1 and IgA2), or subclass of immunoglobulin molecule. In some embodiments, the antibodies are antigen-binding antibody fragments (e.g., human) and include, but are not limited to, Fab, Fab' and F(ab')$_2$, Fd, single-chain Fvs (scFv), single-chain antibodies, disulfide-linked Fvs (sdFv) and fragments including either a $V_L$ or $V_H$ domain. Antigen-binding antibody fragments, including single-chain antibodies, can include the variable region(s) alone or in combination with the entirety or a portion of the following: hinge region, CH1, CH2, and CH3 domains. Also included in the present disclosure are antigen-binding fragments including any combination of variable region(s) with a hinge region, CH1, CH2, and CH3 domains.

Kits

The invention provides kits including antibodies produced in accordance with the present disclosure which can be used, for instance, for the applications described above. The article of manufacture includes a container with a label. Suitable containers include, for example, bottles, vials, and test tubes. The containers can be formed from a variety of materials such as glass or plastic. The container holds a composition which includes an active agent that is effective for applications, such as those described above. The active agent in the composition can include antibodies. The label on the container indicates that the composition is used for a particular application, and can also indicate directions for use, such as those described above.

Utility

Various methodologies exist for screening patients for anti-RBC alloantibodies; however, each method has a common theme. Samples from the patient (serum or plasma) is incubated with a panel of RBCs that express the common RBC alloantigens (screening cells) and if the patient has alloantibodies, then they bind to the screening cells (see FIG. 13). However, most non-ABO alloantibodies are IgG, and are not directly agglutinating. Thus, to facilitate detection, an additional antibody (anti-human globulin [AHG]) is added, to crosslink the patients IgG (see FIG. 13). Non-agglutination based assays (e.g. gel card, solid phase, flow cytometry, etc.) likewise use AHG based binding and/or detection systems.

Human IgGs come in 4 distinct forms, each of which has a separate heavy chain (IgG1, IgG2, IgG3, and IgG4). In most patients, anti-RBC alloantibodies are a mixture of each of these forms; however, in some patients only some IgG subtypes are present, and in rare patients, only a single type of IgG is detectable. Thus, the ability of AHG to recognize each of the IgG subtypes is required in order to achieve the ability to uniformly detect anti-RBC alloantibodies. However, no pure anti-RBC alloantibodies of different IgG subtypes are available to assess the ability of AHG to bind each of the subtypes. Since most AHG is polyclonal antisera (often from rabbits), it will vary from batch to batch, both due to differences in response of individual animals and also due to the changing nature of immune responses in a given animal. Moreover, use of the same AHG will vary in different diagnostic platforms and using different methods. Thus, at the current time, the presence of an antibody that is not recognized by AHG is a source of false negative patient screens prior to transfusion.

Furthermore, the subject embodiments demonstrate "blind spots" in isoalloantibody detection by a monoclonal anti-IgG. Should a patient have anti-RBC antibodies predominantly of an IgG3 subtype of the IgG3-03 and/or IgG3-13 variety, it is possible that a clinically significant alloantibody would be missed. IgG-03 and IgG-13 are estimated at a frequency of 1-3% of Caucasian and 20-30% of certain African populations. The non-reactivity of, for example, IgG4 isoallotypes has not been previously reported.

The subject matter of the present disclosure addresses these and other problems.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Generation of Monoclonal Antibodies Against Kell Antigens

Mice expressing the human Kell glycoprotein (K variant) on RBCs were generated. Transgenic RBCs were then transfused into wild-type mice, thus allowing cell surface expression without the introduction of additional antigens. The recipient mice were pretreated with poly (I:C), which acts a an adjuvant to increase antibody responses to antigens on transfused RBCs, as first described by Dr. Zimring (*Transfusion* 46(9): 1526-36, 2006). Splenocytes from immunized mice were fused with myeloma partners and monoclonal antibodies were isolated. Three clones were isolated that produce monoclonal IgG antibodies, which recognize the K form of the Kell glycoprotein but not the k form. These antibodies are useful typing reagents for human RBCs by a variety of methods, including, but not limited to, fluid phase agglutination, solid phase detection, tube gel detection, flow cytometry detection, enzyme linked immunoadsorbant assay, radioimmunoassay, and Western blot.

Shown in FIGS. 1-6 are the sequences of the antibodies obtained. Upon sequencing, it was determined that the antibodies designated PUMA 1 and PUMA 2 were the same. The shading indicates where the highly variable regions begin. The CDR regions of each heavy or light chain are underlined.

The specificities of the antibodies are shown in FIGS. 7-10. The specificities of the antibodies were determined to be: PUMA1/2 (KEL1 or K), PUMA 3 (a common Kell epitope, PUMA 4 (KEL4 or $Kp^b$). Flow cytometry was utilized to test antibody specificity by indirect immunofluorescence, using the monocolonal antibodies as the primary reagent and a goat-anti-mouse antibody (conjugated to allophycocyanin) as a secondary antibody. Different target cells expressing different Kell variants were used to determine specificity. Targets included RBCs that phenotyped as homozygous for the 3 main antithetical antigens in the Kell system, K/K, k/k, $Kp^b/Kp^b$, $Kp^a/Kp^a$. $Js^b/Js^b$, $Js^a/Js^a$. Differential binding to such tarets tests specificity. In the case of PUMA 1/2, binding was only observed when K was present but not on k/k RBCs. In the case of PUMA 3, binding was observed on all RBCs regardless of phenotype for K/k, $Kp^a/Kp^b$, or $Js^a/Js^b$, thus indicating a common epitope outside these systems. However, PUMA 3 bound to only KELL glycoprotein transgenic murine RBCs and not wild-type murine RBCs; thus, the epitope recognized by PUMA 3 is on the KELL molecule, but not K/k, $Kp^a/Kp^b$, or $Js^a/Js^b$. For PUMA 4, binding was only observed when $Kp^b$ was present but not on $Kp^a/Kp^a$ RBCs.

Example 2: Antibody Modification

Figure 12:
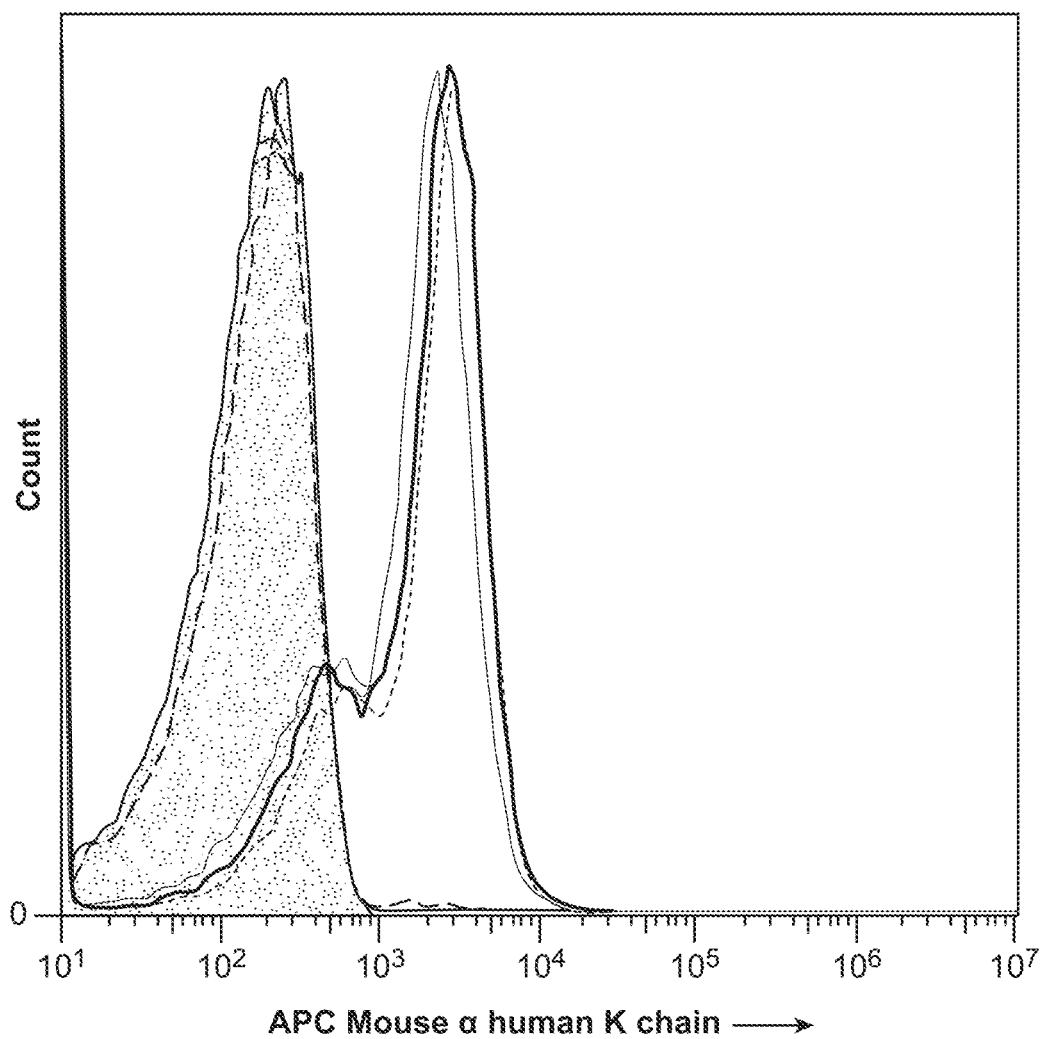
FIG. 12 shows recombinant generation of a humanized form of PUMA1 and its ability to bind to antigen positive RBCs, demonstrating a maintenance of binding after humanization of the IgG constant region.
Figure 14:
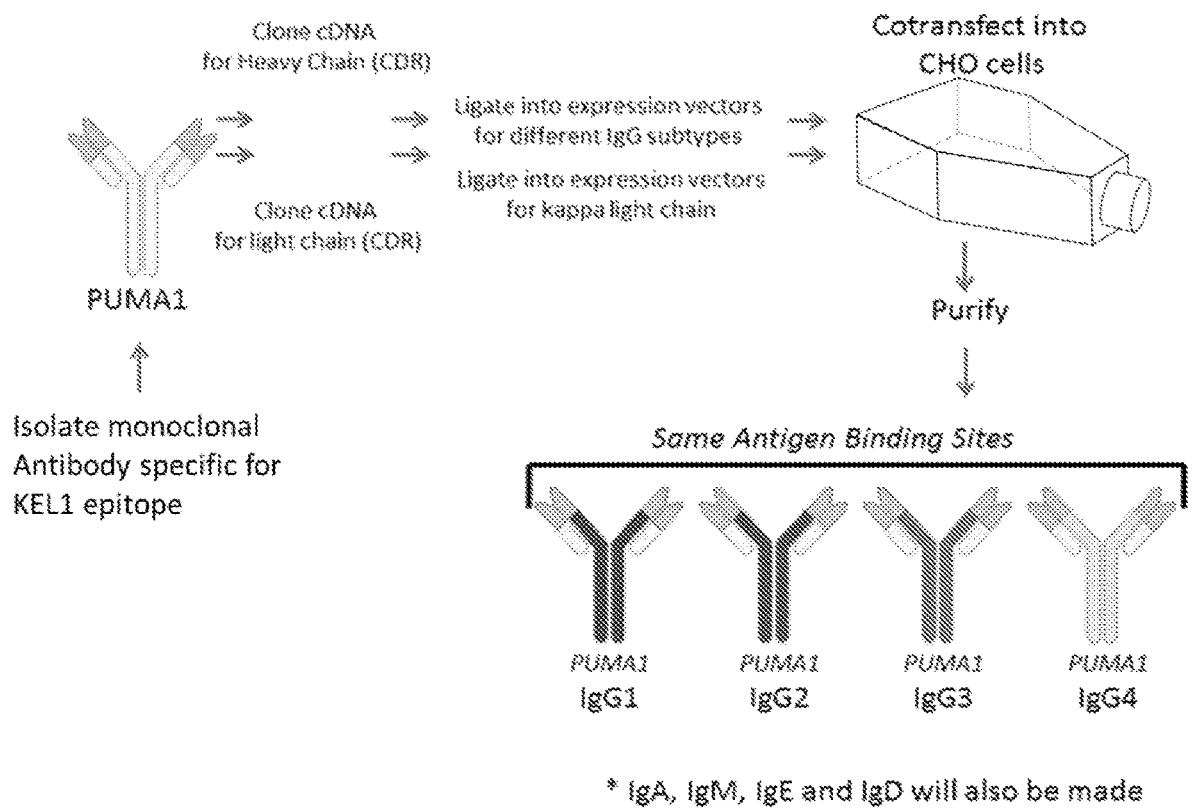
FIG. 14 shows an overview of process to isolate and engineer RBC binding antibodies (anti-Kell) that maintain the same antigen binding sites, but differ in their IgG subtype and allotype.

To allow engineering and manipulation of PUMA1, rapid amplification of cDNA ends (RACE) was performed on both the heavy and light chains of PUMA1, and the sequence for the PUMA1 antibody was elucidated (see FIGS. 1 and 2). Based upon the predicted sequence, mass spectrometry was performed on purified monoclonal PUMA1 and predicted peptides were confirmed for both the heavy and light chain, demonstrating that the correct cDNA was amplified. The identified sequence of PUMA1 heavy chain was cloned in frame with cDNA coding sequence for the mouse IgG3 subtypes, in a eukaryotic expression vector. Similarly, the sequence of the PUMA1 light chain was cloned into a Eukaryotic expression vector. IgG3 was chosen, since it is typically known to have a diminished capacity to induce clearance of bound targets than IgG2a. The plasmid encoding PUMA1 IgG3 heavy chain was transfected into CHO cells, along with the expression vector for light chain, and PUMA1 IgG3 was then purified from culture supernatant using protein A affinity chromatography. Recombinant PUMA1 IgG2a was engineered and expressed in the same way, to allow PUMA1 IgG2a expressed in the same system as the PUMA1 IgG3. Similar to the above murine sequences, PUMA1 has now been humanized by recombinant fusion of the CDRs with human IgG1, IgG2, IgG3 and IgG4 (FIG. 11). An example of the expression of humanized antibodies, while maintaining ability to bind RBCs is shown in FIG. 12.

Example 3: Evaluation of PUMA1 IgG1, IgG2, IgG3, and IgG4 Binding to Anti-Human Globulin (AHG)

Figure 15:
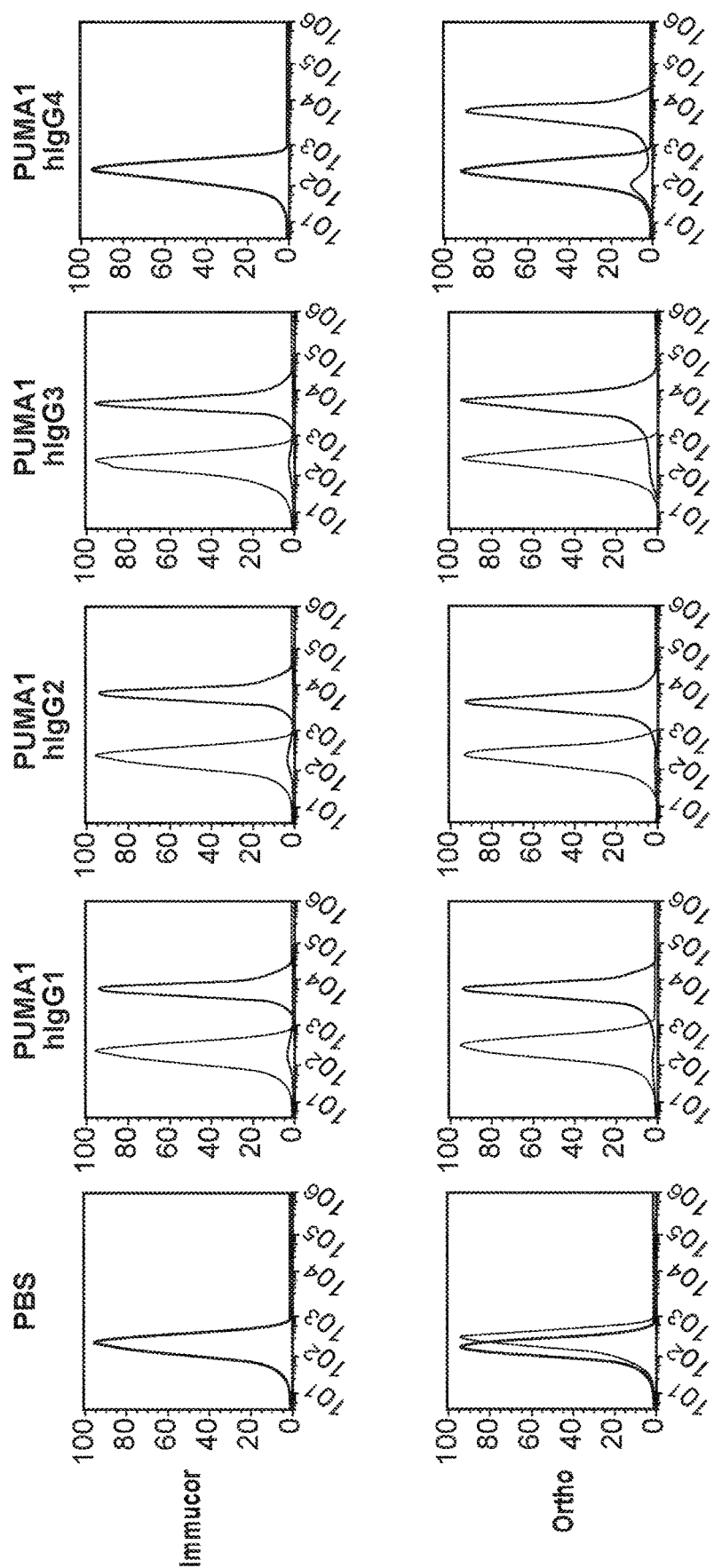
FIG. 15 shows the use of PUMA1 IgG1, IgG2, IgG3, and IgG4 to evaluate various anti-human globulin (AHG) preparations using a FACS assay.
Figure 16:
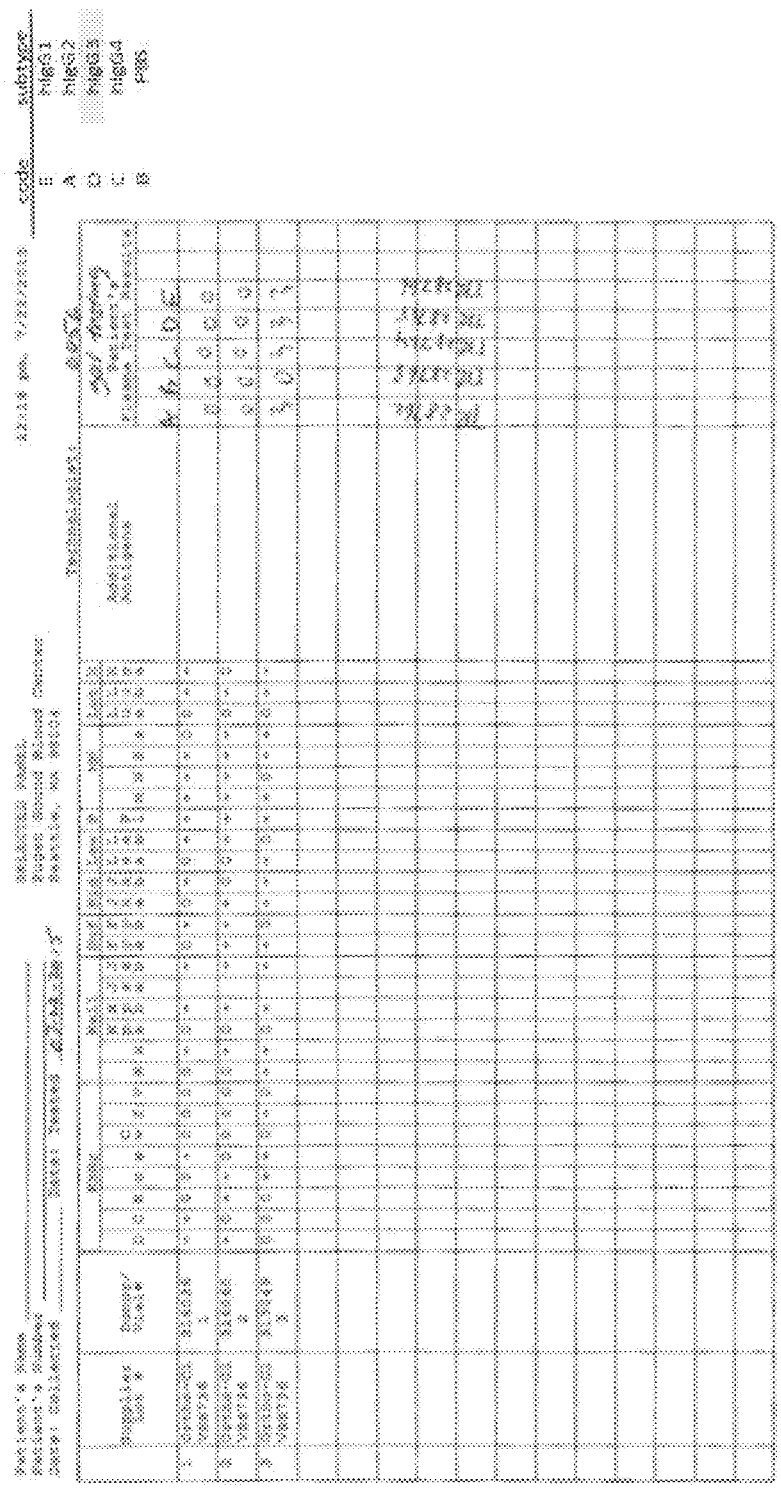
FIG. 16 shows the use of PUMA1 IgG1, IgG2, IgG3, and IgG4 to evaluate various anti-human globulin (AHG) preparations using a gel testing assay.
Figure 18:
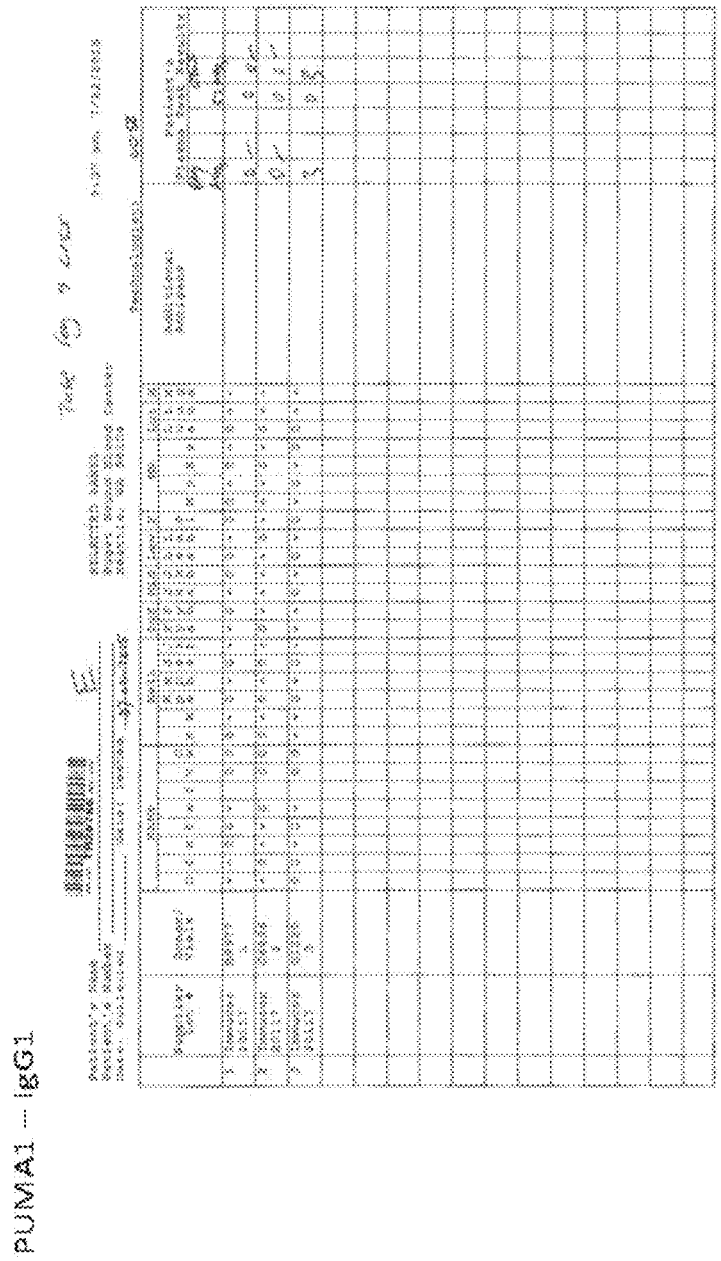
Figure 19:
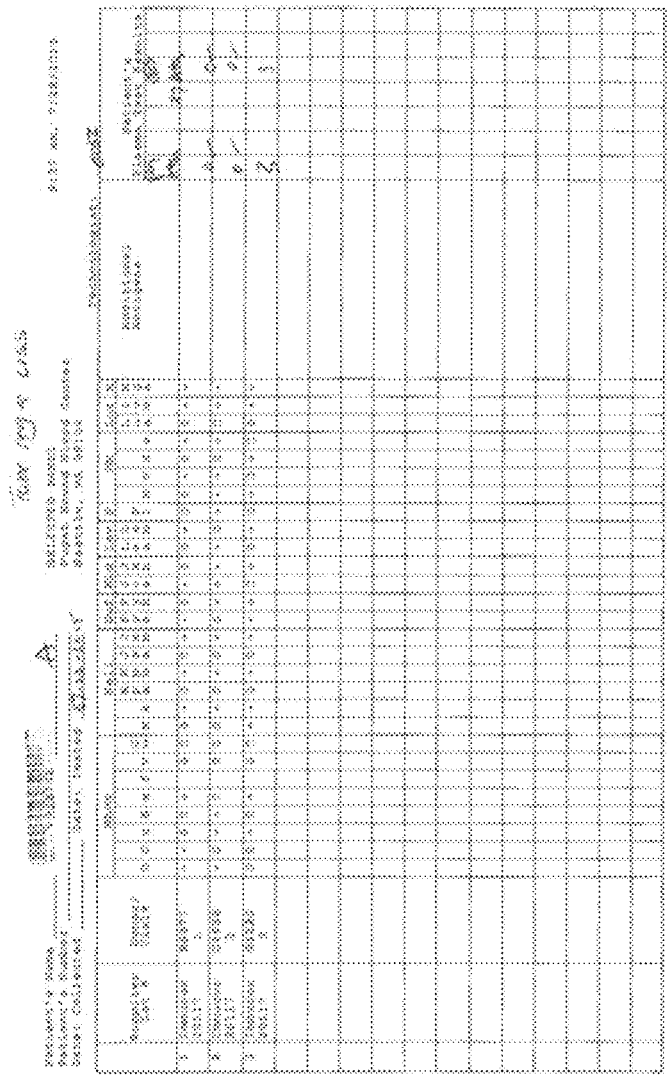
Figure 20:
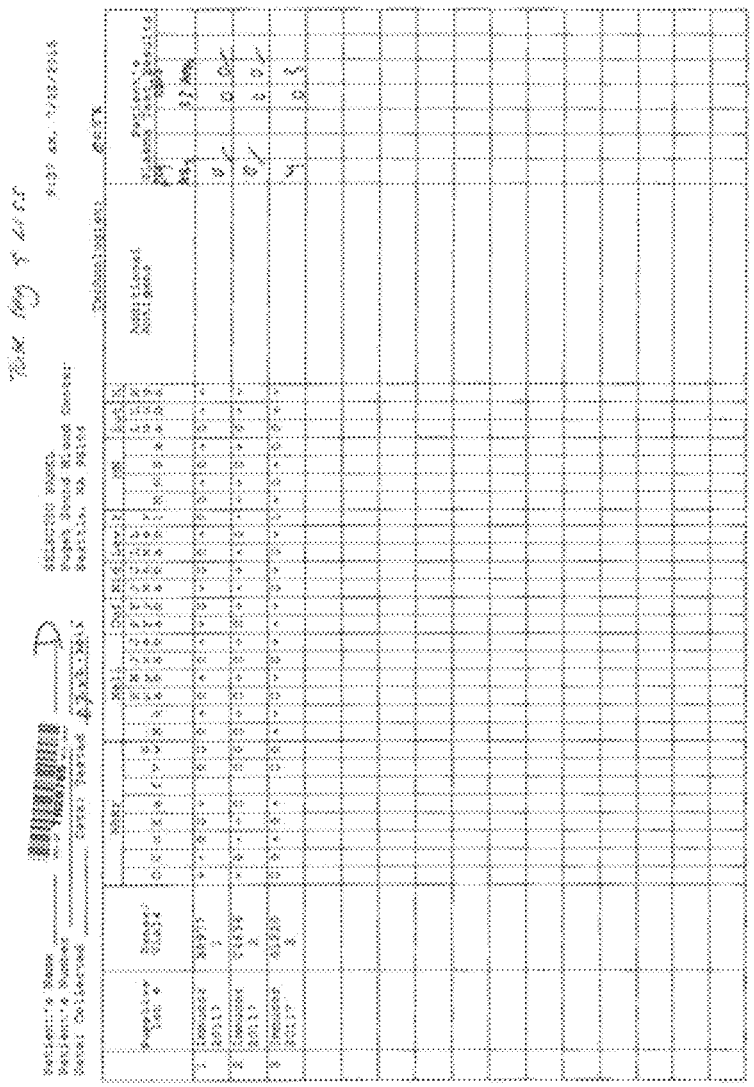
Figure 21:
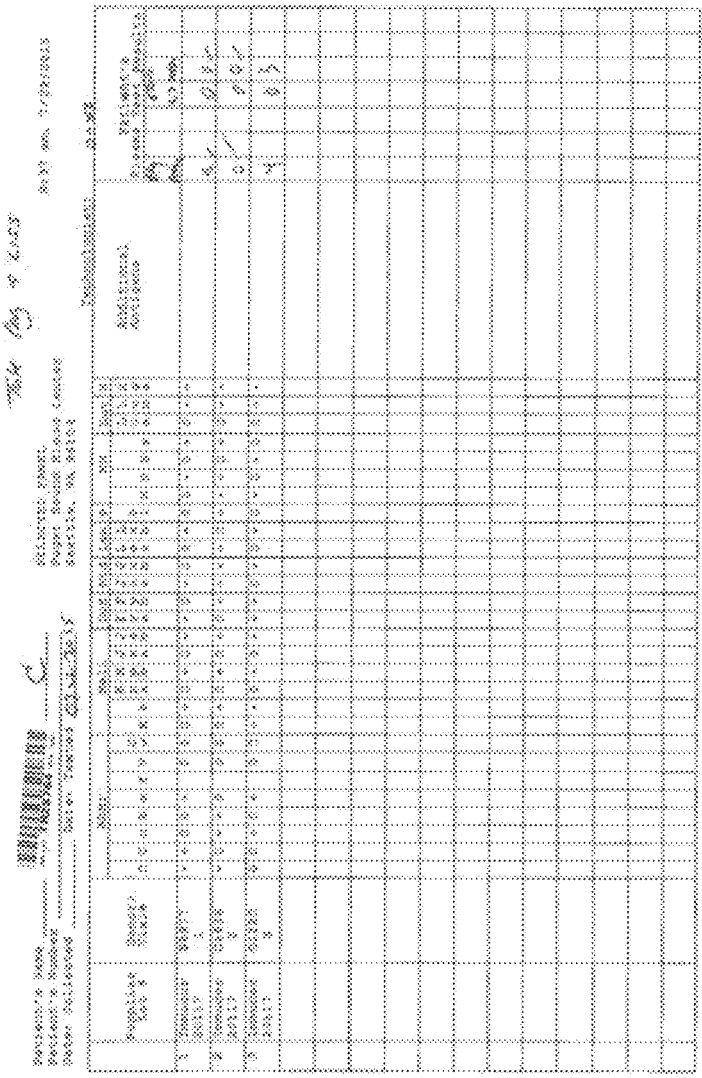
Figure 22:
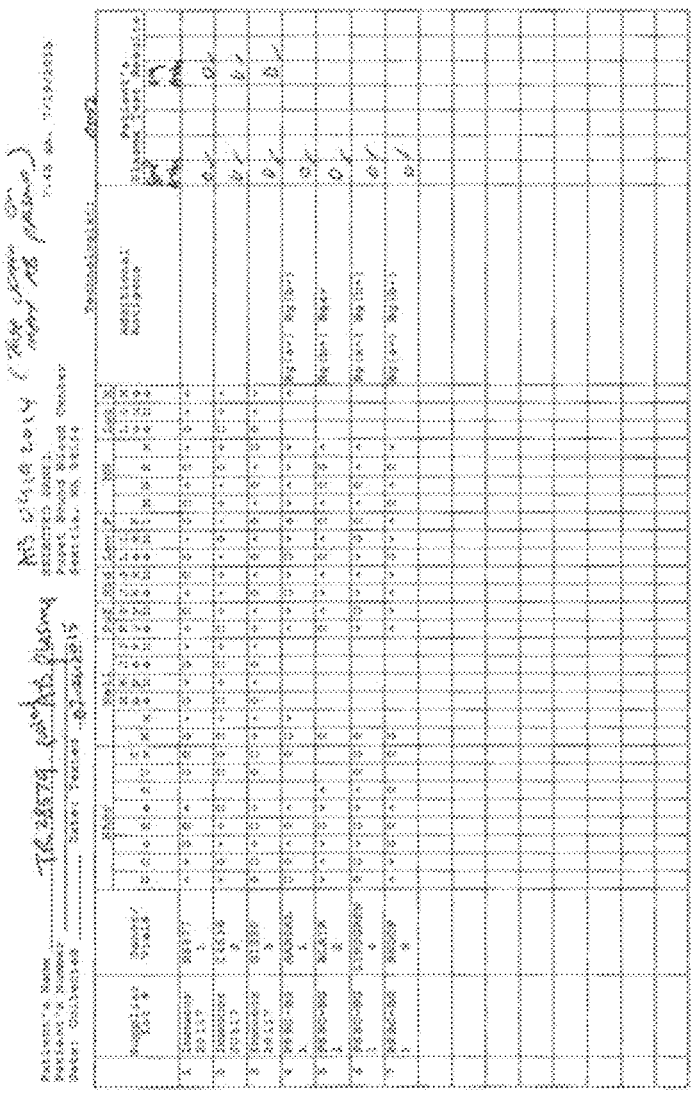
Figure 24:
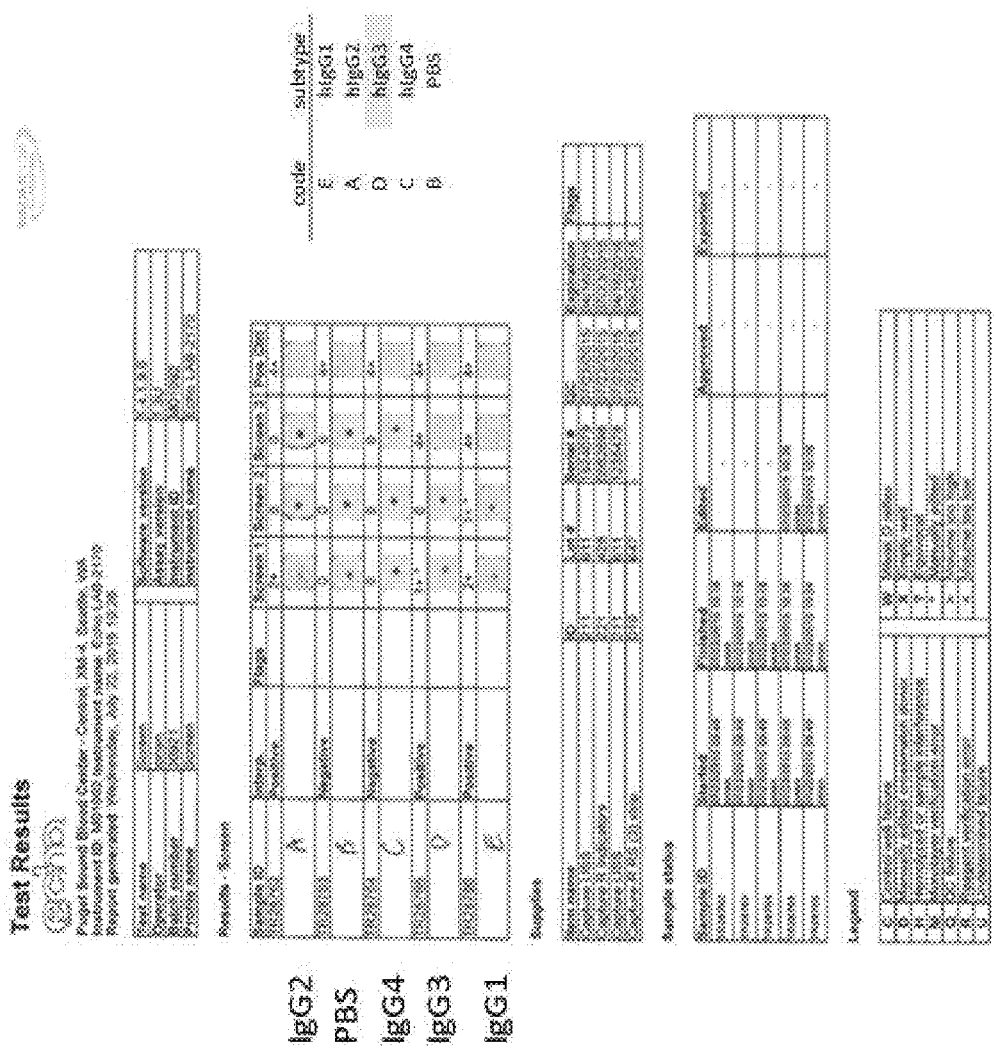
Figure 25:
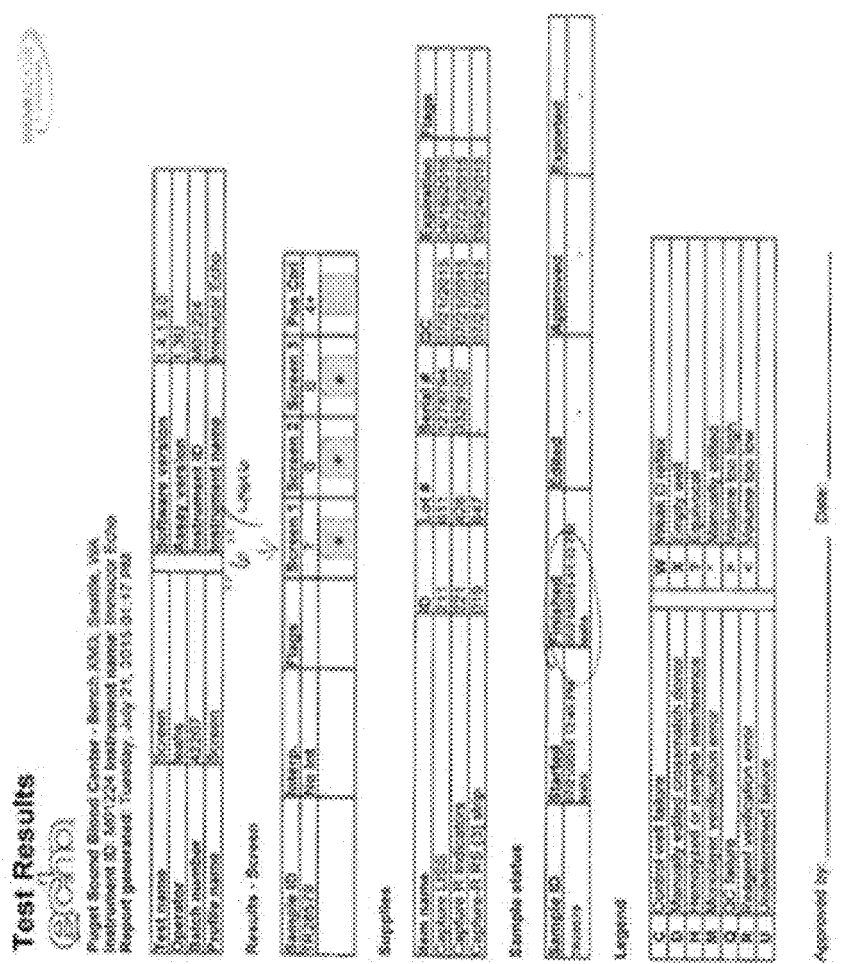

According to the subject aspects, pure PUMA1 IgG1, IgG2, IgG3, and IgG4 were generated and were used to evaluate various AHG preparations, as demonstrated by use in various platforms. FIG. 15 shows the use of PUMA1 IgG1, IgG2, IgG3, and IgG4 to evaluate various AHG preparations using a FACS assay. FIG. 16 shows an evaluation using a gel testing assay. FIGS. 17-22 show an evaluation using a using a tube testing assay. FIGS. 23-25 show an evaluation using a solid phase testing assay. Significantly, as shown in FIG. 15, the Immucor monoclonal AHG did not detect IgG4—as is described in limitations of the Immucor AHG; thus, this validates the disclosure's utility to detect known AHG defects.

Example 4: Evaluation of Serological Blind-Spots for Variants of Human Immunoglobulins by Anti-Immunoglobulin Reagents Alloantibodies to non-ABO red blood cell (RBC) antigens are usually not direct agglutinins, and typically require the addition of anti-IgG to facilitate their detection. The two current methods of manufacturing reagent grade anti-IgG consist of either generating polyclonal anti-IgG from serum of animals (typically rabbits) immunized with polyclonal human IgG or the use of monoclonal antibody based reagents, typically derived from murine sources. While polyclonal anti-IgG contains multiple specificities, and can be a very sensitive reagent, it suffers the potential for variation from animal to animal and from batch to batch. In contrast, monoclonal antibodies are a stable and consistent reagent; however, they can display a more narrow range of reactivity, as typically a single epitope is recognized on the target immunoglobulin.

There are four subclasses of IgG (IgG1, IgG2, IgG3, and IgG4). There is also genetic variation within IgG subtypes wherein the genetic variants are called isoallotypes. There are at least 29 different isoallotypes, with 7, 4, 15, and 3 isoallotypes provided for IgG1-4, respectively. While anti-IgG reagents are required to meet specifications and standards for licensure, the reactivity of anti-IgG with different isoallotypes has not before been characterized. As such, the reactivity of anti-IgG with different isoallotypes is evaluated according to the subject embodiments.

In various aspects, the methods include identifying positive and/or negative reactivity of anti-IgG with one or more isoallotypes, such as any one or combination of the isoallotypes provided in FIG. 29 and/or characterizing the one or more isoallotypes according to the identification. In various aspects, the methods also include identifying the amount of positive and/or negative reactivity of anti-IgG with one or more isoallotypes and/or characterizing the one or more isoallotypes according to the identification.

The generation of test reagents to assess specificity of anti-IgG has historically been challenging and difficult to standardize. In some aspects, solid media is coated with purified IgG of different types to determine anti-IgG reactivity (e.g. ELISAs). While meaningful, such approaches are outside of the context in which IAT and DAT tests are run (e.g. testing IgG bound to the surface of RBCs), and thus may not reflect anti-IgG performance for clinical testing. To create the ability to characterize anti-IgG sensitivities and specificities in the context in which anti-IgG is used in immunohematology, a new monoclonal antibody was generated against the K antigen and isolated the cDNA sequence for the heavy and light chain variable regions. The heavy chain variable region was then ligated into expression vectors using a strategy that fused it in frame with the constant region of human IgG. Separate expression vectors for each of the 29 known IgG isoallotypes were created, allowing expression and purification of isoallotypic variants. This approach isolates isoallotypic variation as an independent variable, as the antigen binding domain is the same for each anti-K variant.

The panel of 29 isoallotypes was applied according to the subject aspects to characterize the performance of different, anti-IgG reagents. Herein it is provided that one or more monoclonal anti-IgG fails to recognize two particular isoallotypes of IgG3 (IgG3-03 and IgG3-13). In addition, it was confirmed that the known property of such a monoclonal anti-IgG does not react with canonical IgG4, and also observed that this non-reactivity extends to the 3 known isoallotypes of IgG4. IgG4 is not known to typically result in acute hemolytic transfusion reactions, and thus non-reactivity with IgG4 is not typically considered as a weakness of monoclonal anti-IgG. However, IgG3 is often considered the most hemolytic IgG subclass. The identified IgG3 isoallotypes have a significant frequency in certain populations, including humans native to Africa.

1. Materials and Methods

A. Mice:

K transgenic mice (published as KEL1 mice) were generated and characterized as previously described and were bred in the BloodworksNW vivarium[4]. CBy.RBF-Rb(8.12)5Bnr/J mice were purchased from Jackson Labs, Bar Harbor Me. (Cat #001802). All mice were maintained on standard rodent chow and water in a temperature- and light-controlled environment. All experiments were performed according to approved Institutional Animal Care and Use Committee (IACUC) procedures.

B. Immunizations and Isolation of Monoclonal Antibody:

RBCs were obtained by peripheral blood from K mice and were transfused into CByJ.RBF-Rb(8.12)5Bnr/J recipients by lateral tail vein injection. CByJ.RBF-Rb(8.12)5Bnr/J recipients were treated with poly (I:C) prior to transfusion as an adjuvant, as previously described.[5] Alloimmunization to the K antigen was monitored by analyzing sera from transfused mice, using K+ RBCs as targets, and performing indirect immunofluorescence by flow cytometry (see below). Immunized mice were boosted 3 days prior to sacrifice, and then splenocytes were harvested and fused (using polyethylene glycol) to myeloma partner FOX-NY (ATCC CRL-1732) followed by culturing in selective media by routine methods. Clones were isolated by limiting dilution culture techniques, and supernatants were screened for anti-K using indirect immunofluorescence and flow cytometry.

C. Identification and Synthesis of Heavy Chain and Light Chain Variable Regions:

RNA was isolated from the PUMA1 antibody-secreting hybridoma and was converted to 5' RACE-ready cDNA using the SMARTer RACE 5'/3' Kit (Clontech, Mountain View, Calif.). Amplification of the heavy chain variable region was performed using primer CH1 (5'-GGCCAGTG-GATAGACAGATGG-3') (SEQ ID NO: 1), while amplification of the light chain variable region was performed using primer Lk (5'-ACACTCATTCCTGTTGAAGCTCTT-3') (SEQ ID NO: 2) (primer sequences published previously[6]). PCR products of the expected size (roughly 380 bp for the heavy chain and 650 bp for the light chain) were ligated into pGEM T-easy (Promega, Madison, Wis.), and multiple isolates sequenced. The predicted light chain variable region was synthesized de-novo (GeneWiz, South Plainfield N.J.) and cloned into pFUSE2-CLIg-hk (Invivogen, San Diego, Calif.). The predicted heavy chain variable region was synthesized de-novo and cloned into each of the following vector backbones; pFUSE-CHIg-hG1, pFUSE-CHIg-hG2, pFUSE-CHIg-hG3 and pFUSE-CHIg-hG4 (Invivogen). Using the IgG1-4 backbones as substrates, derivative plasmids encoding each of the known 29 isoallotypes of IgG were synthesized by a commercial vendor (Genewiz, South Plainfield, N.J., USA).

D. Recombinant Antibody Production:

Recombinant antibodies were produced via transient co-transfection of the plasmids encoding the PUMA1 light chain and appropriate PUMA1 heavy chain into suspension CHO cells as part of the FreeStyle MAX CHO Expression System (ThermoFisher). Briefly, 24 hr prior to transfection, suspension CHO cells were seeded at a density of 0.5×10[6] cells/ml. Transfections were performed using a heavy chain to light chain plasmid ratio of 2:3, and cultures were grown at 37° C. for 7 days. To harvest, cultures were centrifuged at 4000 RPM for 30 min at 4° C., followed by filtration of the supernatant through a 0.45 um filter apparatus to remove any remaining cell debris. In some cases, antibodies were purified from supernatants using rProteinA/G columns (GE Healthcare, Pittsburgh, Pa.), dialyzed, aliquoted and stored at −20° C. Samples from each purification were assessed by SDS-PAGE for both purity and concentration by comparison to a standard curve of purified PUMA1 of known concentration.

E. Flow Cytometry:

Flow cytometry consisted of incubating test RBCs with PUMA1 variants, followed by the anti-IgG being evaluated, followed by a detection reagent. Test RBCs included RBCs from K mice, wild-type mice, and reagent RBCs from humans with the phenotype of (K+k+) or (K−k+). Test RBCs were resuspended in 50 microliters of supernatants of PUMA1 isoallotypes; in some cases a 1/10 dilution in phosphate buffered saline (PBS) was used. For purified IgG1-IgG4 PUMA1, the antibodies were diluted in PBS at the indicated concentrations. The tested anti-IgG reagents were used undiluted. Detection reagents consisted of donkey anti-rabbit conjugated to phycoerythrin at a 1/200 dilution (Affymetrix cat #12-4739-81, Santa Clara, Calif.), goat anti-mouse IgM conjugated to allophycocyanin at a 1/100 dilution (BD Biosciences, cat #550826, San Jose, Calif.), and goat anti-mouse Igs conjugated to allophycocyanin at a 1/100 dilution (SouthernBiotech cat #1020-11s, Birmingham, Ala.). All anti-IgG subclass antibodies were conjugated to phycoerythrin, were purchased from SouthernBiotech (catalog numbers 9056-09, 9070-09, 9210-09, 9200-09), and were used at a dilution of 1.200. All incubations were performed for 30 min at room temperature, followed by three washes with PBS. All flow cytometry was performed on an Accuri 4 color cytometer (BD biosciences, San Jose Calif.) and all data was analyzed with Flo-Jo version 10.

F. Solid Phase Testing:

Daily instrument maintenance and quality control were performed as described in the Galileo Echo (Immucor, Norcross, Ga.) Operator Manual prior to testing. The PUMA1 subtypes were tested using combinations of in-date lots of Capture-R Ready Screen 3 strips (CRRS3), Capture LISS and Capture-R Indicator Cells (CRIND) on 2 Galileo Echo instruments (Immucor). The instrument reads and interprets the test results of the individual test wells, which in the case of CRRS3 meant that one of the three test wells contained a K+k+ red cell monolayer and 2 K-k+ red cell monolayers. The antibody samples were evaluated on 2 instruments using 2 lots of CRRS3 strips and 2 lots of CR-IND. Two lots of Capture-P indicator cells were also used.

G. Tube Antiglobulin Test (AGT):

PUMA1 was tested with Panoscreen I, II & III reagent RBCs (Immucor) by a standard saline tube AGT as described in the direction insert. Briefly, equal volumes of antibody and 2-4% reagent RBCs were incubated for 45 minutes at 37° C. After incubation the tubes were washed 3 times with an excess of PBS. Anti-IgG reagent was added and the tubes centrifuged and then examined for the presence of agglutination. Gammaclone Murine Monoclonal Anti-IgG (Immucor) was used as Anti-IgG reagents.

H. Gel Testing:

Gel testing was carried out using antibody-screening reagent RBCs (0.8% Surgiscreen RBCs I, II, and III) MTS Anti-IgG Cards, as per manufacturer's instructions (ID-Micro Typing System Gel Test; Ortho Clinical Diagnostics, Inc., Raritan, N.J.).

2. Results

Figure 26A:
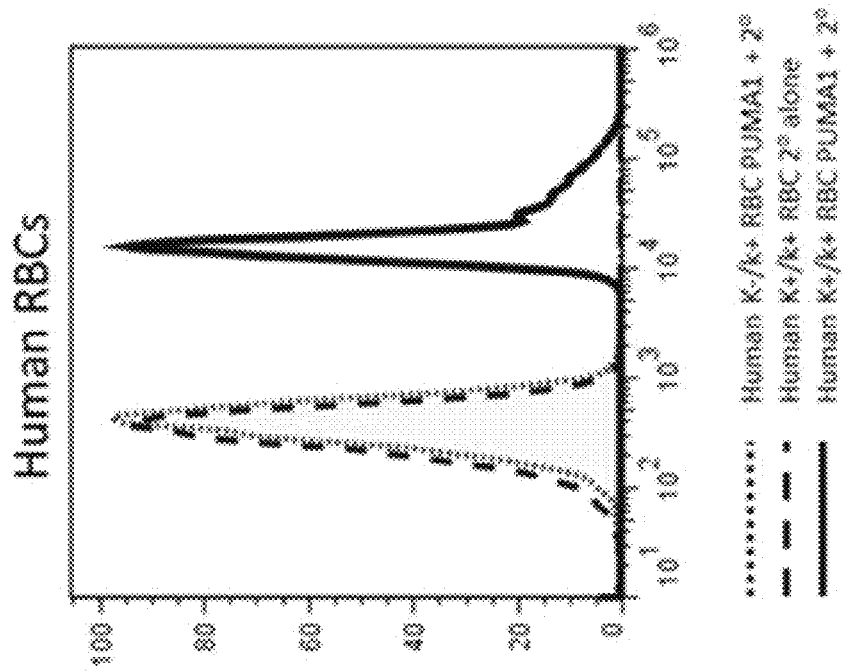
FIGS. 26A-26C illustrate specificity of PUMA1 for the K antigen and strategy to generate PUMA1 variants.
Figure 26B:
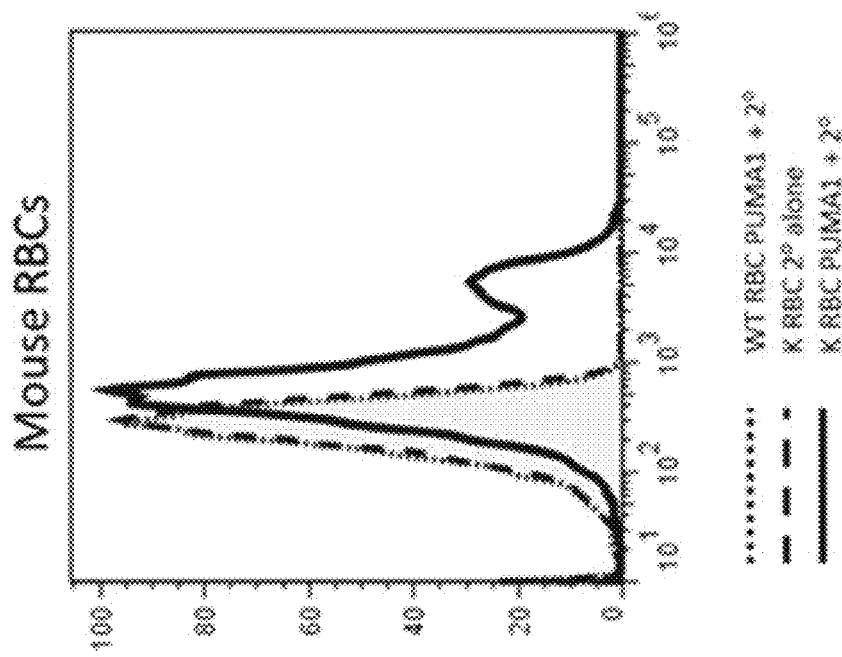

A. Generation of a Novel Monoclonal Anti-K Antibody:

RBCs were utilized from previously reported K transgenic mice as an immunogen. Mice with high-titer antisera specific for K transgenic RBCs were identified, spleens were harvested, and fusions were performed with an immortal myeloma line. Through traditional cell cloning methods, a new monoclonal line (PUMA1) was isolated, that secreted an antibody with specificity for the K antigen. PUMA1 was reactive with RBCs from the K transgenic donor mouse used for immunization; no signal was observed on wild-type RBCs compared to secondary antibody alone (FIG. 26A). Similarly, PUMA1 was reactive with human RBCs of the K+k+ phenotype but not with K-k+ RBCs (FIG. 26B). Characterization of PUMA1 indicates that it was of the murine IgG2a subclass and expressed a kappa light chain (data not shown).

B. Detection of IgG Subtypes and Isoallotypes by Different Anti-IgG Reagents

Figure 26C:
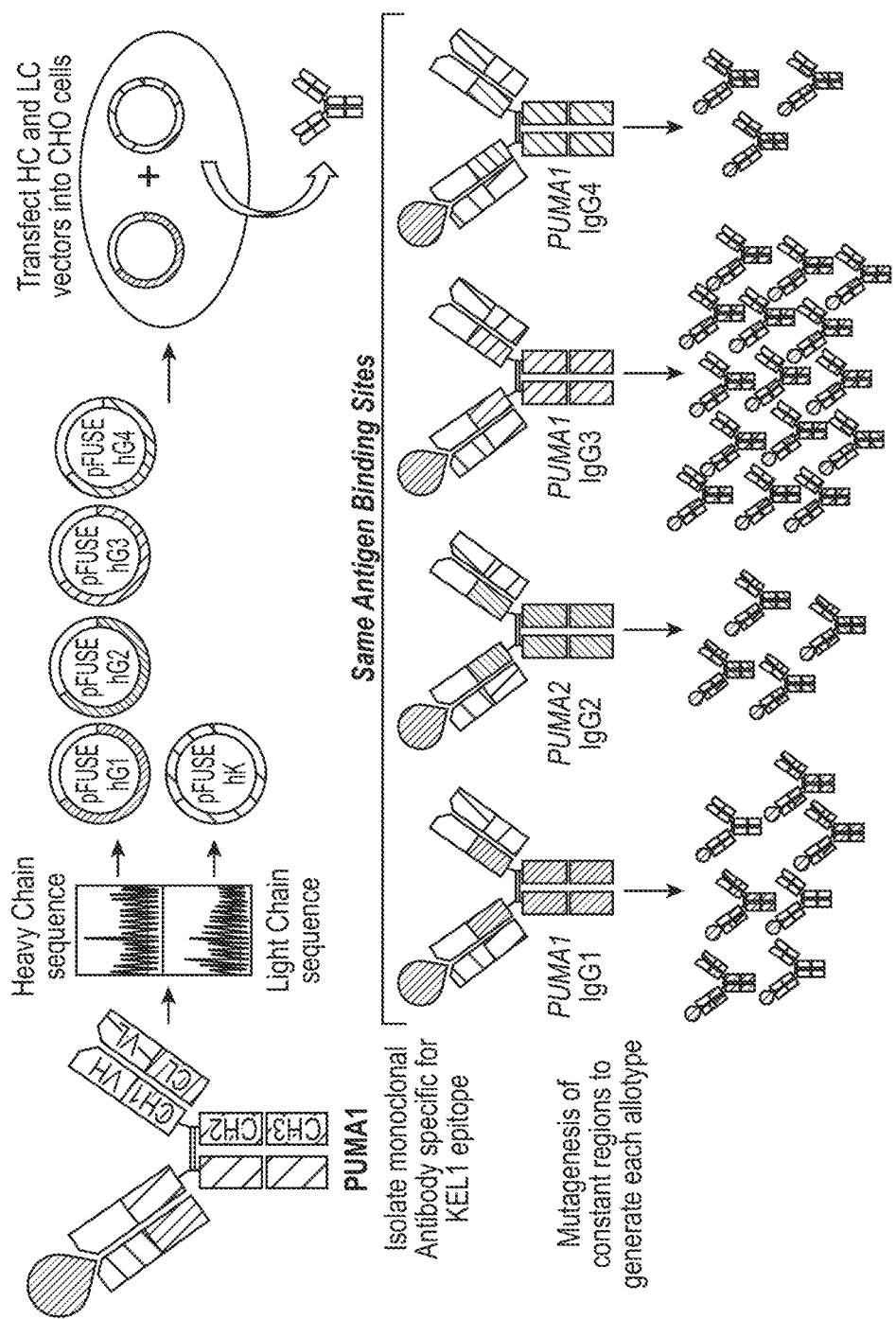

In order to allow engineering of the PUMA1 antibody, the cDNA for the heavy and light chains were isolated from the PUMA1 hybridoma, and the coding region for the antibody complementary determining region (CDR) was determined. The heavy chain CDR was cloned, including a Kozak sequence, ATG, and leader sequence, in frame, into expression vectors for human IgG1, IgG2, IgG3, and IgG4 (FIG. 26C). Each expression vector was used as a starting material to generate additional expression vectors for the known isoallotypic variants of IgG1-4[1]. Likewise, the light chain CDR was cloned in frame, into an expression vector for human kappa light chain. The plasmid encoding the light chain was then co-transfected with expression vectors for each of the canonical IgG subclasses and isoallotypes, and cell culture supernatants which expressed PUMA1 IgG variants were collected. Each PUMA1 variant was incubated with K+k+ RBCs, followed by incubation with either monoclonal or polyclonal anti-IgG, followed by the appropriate detection reagents (see methods). Binding of PUMA1 variants was assessed by flow cytometry. Background staining was determined using K-k+ RBCs that don't express the K antigen.

All 29 isoallotypes of human IgG were detected by polyclonal anti-IgG. In contrast, the tested monoclonal anti-IgG bound to 24 out of 29 isoallotypes, failing to recognize IgG3-03, IgG3-13, IgG4-01, IgG4-02, and IgG4-03 (see FIG. 27). The lack of detection of these isoallotypic variants was not due to their lack of expression or inability to recognize the K antigen, as equivalent signal was detected on K+k+ but not K-k+ RBCs for all 29 isoallotypes by polyclonal anti-IgG.

C. Characterization of Anti-IgG Regents for Sensitivity to Human IgG Subclasses.

To allow standards of known quantity, so as to allow precise determination of the sensitivity of anti-IgG, the canonical forms of IgG1-IgG4 were expressed and purified by affinity chromatography (All canonical forms have an isoallotype designation of *01). Protein electrophoresis was performed on each purified IgG subclass of PUMA1, both to assess expression and purity (FIG. 26A). The same single band was observed at 25 kD for each preparation, consistent with the same kappa light chain of PUMA1. In addition, bands corresponding to each of the heavy chains were also observed, at the predicted molecular weights consistent with the known size of each of the IgG subclasses. As predicted, only the IgG3 heavy chain displayed a higher molecular weight in accordance with its longer hinge region. To test if the purified PUMA1 IgG1-IgG4 maintained antigen binding properties and as a further confirmation as to the correct expression, of IgG subtypes, K+k+ human RBCs were stained with each of the PUMA1 preparations, followed by secondary antibodies specific for the human IgG subclasses. Each of the PUMA1 IgG subclasses bound to (K+k+) but not (K-k+) RBCs, was reactive with the secondary antibody specific for the appropriate IgG subclass, and was nonreactive with secondary antibodies of other specificities (FIG. 26B). Together, these findings demonstrate the successful purification to homogeneity of the expressed panel of antibodies. Accordingly, determination of protein concentration in these preparations reflects the quantity of anti-K IgG, allowing quantitative standard reagents.

Figure 28B:
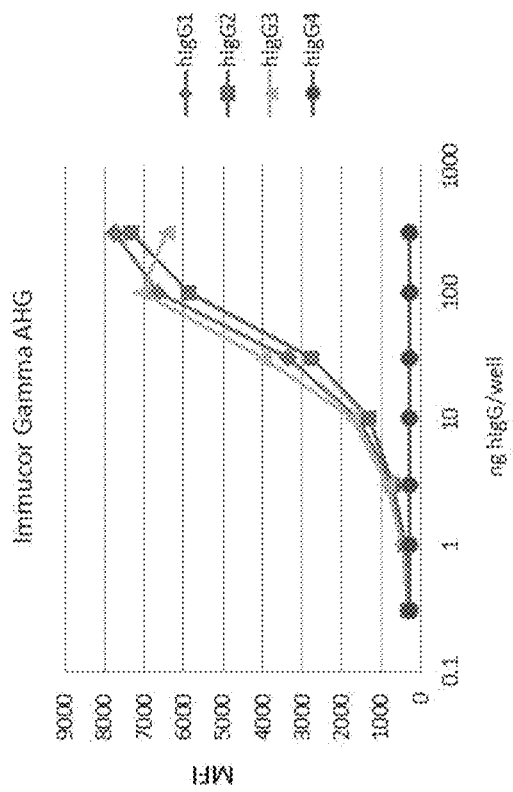
FIGS. 28A, 28B provide data obtained when human K+k+ RBCs sere incubated with a titration of each human IgG subclass of PUMA1 in the indicated amounts, followed by staining with the appropriate secondary antibodies (see methods). This was carried out for both of the indicated anti-IgG reagents, Ortho AHG in FIG. 28A, and Immucor Gamma AHG in FIG. 28B. All data are derived from mean fluorescent intensity determined by flow cytometry.
Figure 28A:
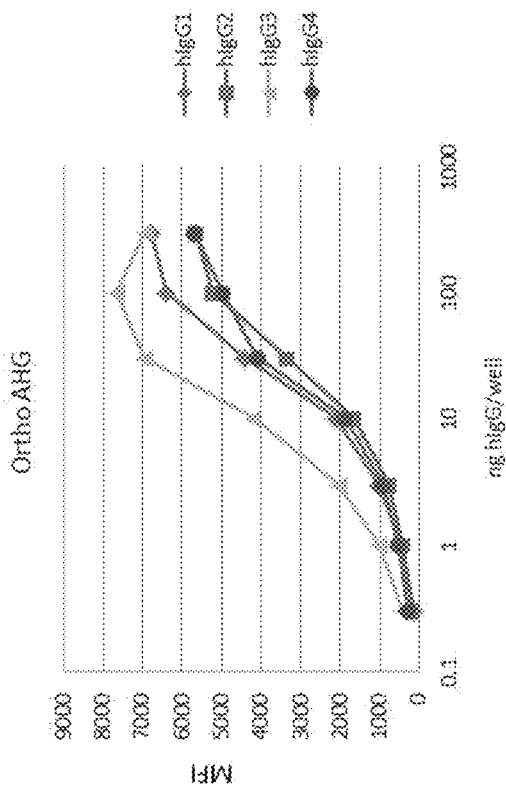

To assess the sensitivity of commercially available anti-IgG preparations for different human IgG subclasses bound to RBCs, K+k+ RBCs were first incubated with PUMA1 of the different human IgG subclasses, followed by incubation with anti-IgG. Treated RBCs were then stained with a fluorescently labeled antibody specific for the species in which the anti-IgG was generated (and non-reactive with human IgG). For each anti-IgG, the same secondary antibody was used to detect binding of the anti-IgG to each human PUMA1 IgG subclass. To assess relative sensitivity, titrations of each PUMA1 IgG subclass were carried out and samples were analyzed by flow cytometry using mean fluorescent intensity (MFI) to quantify staining (FIGS. 28A, 28B). The polyclonal rabbit anti-IgG reagent produced by Ortho Diagnostics (Ortho anti-IgG) had an increased sensitivity for IgG3 compared to other IgG subtypes (FIG. 28A). In contrast, the mouse monoclonal anti-IgG reagent produced by Immucor-Gamma (Immucor Gamma anti-IgG) had equivalent sensitivity for IgG1, IgG2, and IgG3; however, as observed in the qualitative screening above (see FIG. 27), the Immucor Gamma anti-IgG had no detectable reactivity with IgG4 (FIG. 28B).

D. Specificity of Anti-IgG Reagents in Common Platforms Used in Immunohematology Labs Flow cytometry remains a technique predominantly utilized for research purposes. Accordingly, the select forms of PUMA1 IgG1-IgG4 were evaluated in assay systems and on platforms currently in use in clinical immunohematology labs. Five blinded samples were analyzed by the BloodworksNW Immunohematology Reference Laboratory and also by the research and development labs at Immucor Inc. The samples consisted of the canonical PUMA1 IgG1-IgG4 subtypes or PBS as a negative control. The blinded samples were evaluated using both solid phase assay systems (Galileo Echo platform, Immucor), by tube testing, or using gel. Overall results are shown, which were in agreement with flow cytometry results (Table 1). In all cases, systems that utilized the Immucor monoclonal 16H8 based reagent, either by solid phase (Capture-R indicator cells) or tube testing with Gammaclone anti-IgG reagent, detected. PUMA1 IgG1, IgG2, and IgG3 (but not IgG4) Capture-P indicator cells are prepared using a polyclonal rabbit anti-IgG, and detect all 4 PUMA1 IgG subclasses. In other systems using polyclonal rabbit anti-IgG from Ortho, all four IgG subclasses of PUMA1 were detected.

Additional gel testing and wet tube testing was carried out on the IgG3 isoallotypes that were not detected by the monoclonal anti-IgG using flow cytometry. Consistent with the flow cytometry results, the canonical IgG3-01 was detected by Gamma clone reagent in wet tube testing and in gel; however, neither IgG3-03 nor IgG3-13 was detected in either platform. Also consistent with flow cytometry, the polyclonal anti-IgG detected IgG3-01 and IgG3-03 both in wet tub testing and in gel. In no case was a positive signal observed in the PBS control sample. Positive signals were also not detected whenever K-k+ RBCs were used as screening RBCs (data not shown). Thus, in all cases, standardly utilized immunohematology methods generated data that was in agreement with flow cytometry. Sensitivity titrations were not carried out in each of the clinically used immunohematology platforms.

3. Discussion

The sensitivity and specificity of the anti-IgG component of AHG reagents are essential for immunohematology labs to detect RBC alloantibodies and autoantibodies, most of which are not direct agglutinins. However, human IgG is not a monomorphic entity; rather, it consists of 4 distinct IgG subclasses (IgG1-IgG4), each of which have natural genetic variation in their constant regions, giving rise to at least 29 isoallotypes. The subject embodiments are the first assessment of anti-IgG reactivity to the different human IgG isoallotypes. The difficulty in generating test systems of this type have been acknowledged in past efforts; however, the current use of, for example, recombinant antibodies circumvents the previous barriers. By expressing a panel of antibodies with the same antigen-binding domain, but different IgG constant regions, isoallotype has been isolated as an independent variable.

Monoclonal anti-IgGs have a number of distinct advantages, including the relative ease of production and consistency of the reagent over time. Moreover, they do not require the ongoing immunization and housing of animals to maintain a polyclonal antisera, which can vary from batch-to-batch. However, the downside to monoclonal reagents can be a more myopic focus on a smaller number of epitopes (or a single epitope) on the target molecule, potentially decreasing the range of recognized entities. In aspects of the current disclosure, a commonly used monoclonal anti-IgG does not recognize 5 of the 29 known isoallotypes of human IgG.

IgG3-03 and IgG3-13 are found at their highest frequencies in a number of ethnic groups of African origin[7]. IgG3 is typically considered a clinically significant IgG subtype, which is often associated with hemolytic pathology[8]; however, patients with IgG3 and no hemolytic anemia have also been described. The hemolytic potential of different IgG isoallotypes has not previously been assessed; thus, it is unclear where IgG3-03 and/or IgG3-13 fall on the hemolytic spectrum. Juxtaposition of the amino acid sequences indicates that the presence of a glutamic acid (instead of glutamine) at position 419 is a common characteristic of the IgG3-03, IgG3-13, and each of the IgG4 isoallotypes. Thus, the Q to E changes can be responsible for an alteration in epitope recognized by the characterized monoclonal anti-IgG. As IgG4 is generally considered to not cause acute hemolytic pathology, it is possible that Q to E change in IgG3-03 and IgG3-13 disrupts IgG3 effector function. However, given the potential for hemolysis by IgG3 in general, prudence would dictate an assumption of hemolytic potential by IgG-03 and/or IgG-13, until proven otherwise.

The non-reactivity of Immucor Gamma anti-IgG with IgG4 is a previously known property of this particular monoclonal antibody (clone 16H8)[11], which is listed as a limitation of the antibody in its package insert. The observation that this non-reactivity extends to different IgG4 isoallotypes is a novel observation contained herein. Although there are no data on the hemolytic potential of different IgG4 isoallotypes, it is precisely because IgG4 is typically considered benign that the inability of the monoclonal Immucor Gamma anti-IgG (clone 16H8) to bind IgG4 has been acceptable. Indeed, it has been argued that since IgG4 are typically benign, then non-reactivity to IgG4 is of benefit, since it avoids costly and time-consuming serological workups, which can ultimately have a negative impact on patient care through delay in blood product delivery.

While IgG4 is not associated with acute hemolytic events, it is unclear that IgG4 is entirely benign. Studies by Baldwin et al. convincingly demonstrated that an anti-JMH, which was IgG4, did indeed fail to cause an acute hemolytic transfusion reaction after transfusion of a whole unit of JMH+ RBCs[12]. However, whereas short term $^{51}$Cr studies in this patient showed a greater than 70% 1 hr recovery, the long term $T_{1/2}$[51]Cr survival was only 12 days. Thus, while not acutely hemolytic, it does appear that an anti-JMH IgG4 can substantially decrease the circulatory life-span of JMH+ RBCs. This can affect not only long-term efficacy for chronically transfused patients (e.g. increase chances of iron overload due to need of more units over time), but it is also unclear if ongoing clearance of RBCs by antibody is a benign process. Such sequelae would not cause signs or symptoms that physicians or patients would experience or report, as one would need to perform RBC survival studies to detect the problem. Accordingly, it is of little value to exclude this as a potential problem by the argument that this reagent has been used for decades without reports of any problems. Finally, it is possible that an IgG4 alloantibody can predict immune response of an IgG1-IgG3 type upon subsequent transfusion, as it has been shown that repeat exposure can alter IgG subtype[13]. This would not be due to IgG4 secreting cells further switching, but rather due to a new B cell response or IgM+ memory B cells[14]. Thus, on balance, it is unclear if an inability to recognize IgG4 is a desirable or undesirable property in an anti-IgG regent.

The monoclonal anti-IgG had the same sensitivity for each IgG subtype, which can be an attribute of a monoclonal reagent that recognizes an epitope that is common to the IgG types that it recognizes. In contrast, the rabbit polyclonal reagent tested was more sensitive to IgG3. It is unclear how such differential sensitivity of anti-IgG for different IgG subtypes can affect serological testing; however, it raises the possibility of differential detection of alloantibodies in a given patient sample by different anti-IgG as a property of the relative levels of IgG subtypes, which can change over time as a patient's alloimmune response evolves.

It could be argued that there is little likelihood of an adverse patient outcome due to the lack of reactivity of some anti-IgG (as demonstrated herein). The patient populations to consider include alloimmunized transfusion patients, pregnant women with a possibility of HDN, and patients with autoimmune hemolytic anemia (AIHA). Detailed studies in AIHA patients have demonstrated that a mixture of IgG subclasses is the most common presentation, and has a stronger association with hemolysis than isolated IgG subclasses[15,16]. In such patients, the monoclonal anti-IgG would still pick up the anti-RBC antibodies, as a mixture of IgG subclasses is present. However, a significant number of patients have also been observed who have only a single detectable IgG subclass on their RBCs. In a combined study of both healthy blood donors who had a positive DAT and patients with AIHA, isolated IgG1, IgG2, or IgG3 were all observed in the context of clinically significant hemolysis; no hemolysis was observed with isolated IgG4[17].

Although infrequent in the Caucasian population (overall about 1%), IgG3-03 and IgG3-13 have up to a 30% frequency in African populations of certain distributions[7]. Thus, it is likely that there are some patients who are homozygous for either IgG3-03 or IgG3-13. In addition, some patients are likely to be compound heterozygotes for IgG3-03/IgG3-13. Alternatively, even if patients are heterozygous for IgG3-03 or IgG3-13, B cells that make alloantibodies can develop predominantly from clones that express the IgG3-03 or IgG3-13 isoallotype. In such patients, in the event that an anti-RBC antibody response is predominantly of the IgG3 subtype, then they may not be detected by platforms using the monoclonal anti-IgG characterized herein.

In summary, the subject aspects include an approach for assessing the sensitivity and specificity of anti-IgG for different subtypes and isoallotypes of human IgG. Polyclonal anti-IgG had a differential sensitivity for IgG subtypes, but recognized all 29 known human IgG isoallotypes. In contrast, one monoclonal reagent had blind spots for 5 isoallotypes, of the IgG3 or IgG4 subtype. It is unclear what the clinical significance of these blind spots is; however, given the hemolytic potential of IgG3, caution may necessitate reconsideration of this reagent.

The overall approach used herein can be utilized to further assess sensitivity and specificity of other anti-IgG reagents, for any diagnostic platform that has an anti-IgG component. As knowledge of the human genome evolves, and new isoallotypes of IgG are identified, this approach can be expanded to continue to refine the understanding of the diagnostic specifics of anti-IgG against human immunoglobulins.

TABLE 1

PUMA1 of the indicated human IgG subclasses was analyzed using test RBCs of a K+k+ phenotype and using the indicated platforms (see methods for details).

| Sample ID | Echo (M00211) Test Results | | Tube AGT | | |
|---|---|---|---|---|---|
| | Capture-R Indicator Cells | Capture-P Indicator Cells | Gammaclone AHG Reagent | Ortho AHG | Gel Testing Ortho |
| (PUMA1-IgG1) | Positive | Positive | 4+ | 4+ | 3+ |
| (PUMA1-IgG2) | Positive | Positive | 4+ | 3+ | 3+ |
| (PUMA1-IgG3) | Positive | Positive | 4+ | 4+ | 3+ |
| (PUMA1-IgG4) | Negative | Positive | 0 | 3+ | 3+ |
| (PUMA1-IgG3-03) | UN | UN | 0 | 3+ | 3+ |
| (PUMA1-IgG3-6) | UN | UN | 3+ | 3+ | 3+ |
| (PUMA1-IgG3-13) | UN | UN | 0 | 3+ | 3+ |
| (PBS) | 0 | 0 | 0 | 0 | 0 |
| Source of anti-IgG | Clone 16H8 | Polyclonal Rabbit | Clone 16H8 | Polyclonal Rabbit | Polyclonal Rabbit |

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed:

1. A method to determine the specificity and sensitivity of an anti-human globulin antibody, the method comprising:
   a) binding the anti-human globulin antibody to a panel of human antibodies, wherein the human antibodies within the panel are of different Ig subtypes and comprise:
      a heavy chain comprising:
         complementarity-determining region (CDR)1 of SEQ ID NO: 114,
         CDR2 of SEQ ID NO: 115, and
         CDR3 of SEQ ID NO: 116;
      and
      a light chain comprising:
         CDR1 of SEQ ID NO: 117,
         CDR2 of SEQ ID NO: 118, and
         CDR3 of SEQ ID NO: 119;
   and
   b) detecting the binding of the anti-human globulin antibody to human antibodies of the panel with particular Ig subtypes, thus determining the specificity and sensitivity of the anti-human globulin antibody.

2. The method of claim 1, wherein the human antibodies are IgG.

3. The method of claim 1, wherein the different Ig subtypes comprise IgG1, IgG2, IgG3, and IgG4.

4. The method of claim 1, wherein the different Ig subtypes comprise an isoallotype of IgG1, IgG2, IgG3, or IgG4.

5. The method of claim 4, wherein the isoallotype is selected from the group consisting of IgG1-01, IgG1-03, IgG1-05, IgG1-07, IgG1-08, IgG1-01v2, and IgG1-04v2.

6. The method of claim 4, wherein the isoallotype is selected from the group consisting of IgG2-01, IgG2-02, IgG2-04, and IgG2-06.

7. The method of claim 4, wherein the isoallotype is selected from the group consisting of IgG3-01, IgG3-03, IgG3-04, IgG3-06, IgG3-08, IgG3-09, IgG3-11, IgG3-12, IgG3-13, IgG3-14, IgG3-15, IgG3-16, IgG3-17, IgG3-18, and IgG3-19.

8. The method of claim 4, wherein the isoallotype is selected from the group consisting of IgG4-01, IgG4-02, and IgG4-03.

9. The method of claim 1, wherein the human antibodies are IgA, IgM, IgE, or IgD.

10. The method of claim 1, wherein the human antibodies comprise heavy chains comprising SEQ ID NOs: 3 or 5.

11. The method of claim 1, wherein the human antibodies comprise light chains comprising SEQ ID NOs: 7 or 9.

12. The method of claim 1, wherein the human antibodies bind to an antigen with an affinity constant ($K_D$) of less than $1\times10^{-8}$ M.

13. The method of claim 1, wherein the method is performed using a fluorescence-activated cell sorting (FACS) assay, a gel testing assay, a tube testing assay, or a solid phase testing assay.

* * * * *

SEQUENCE LISTING

```
<160> NUMBER OF SEQ ID NOS: 130

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggccagtgga tagacagatg g                                                   21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acactcattc ctgttgaagc tctt                                                24

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Leu Asn Pro Asn Asn Gly Asp Thr Phe Tyr Asn Gln Lys Phe
    50                  55                  60

Lys Gly Lys Ala Thr Leu Thr Val Asp Lys Ser Ser Ser Thr Ala Tyr
65                  70                  75                  80

Ile Gln Leu Asn Ser Leu Thr Ser Glu Asp Ser Ala Val Tyr Tyr Cys
                85                  90                  95

Ala Arg Glu Ala Gly Ser Ser Phe Gly Ser Ser Cys Asn Tyr Trp Gly
            100                 105                 110

Gln Gly Thr Thr Leu Thr Val Ser
        115                 120

<210> SEQ ID NO 4
<211> LENGTH: 561
<212> TYPE: DNA
<213> ORGANISM: Artificial Sequence
<220> FEATURE:
<223> OTHER INFORMATION: Description of Artificial Sequence: Synthetic
``` polynucleotide
<220> FEATURE:
<221> NAME/KEY: CDS
<222> LOCATION: (1)..(558)

<400> SEQUENCE: 4

```
atg tcc tct cca cag aca ctg aac aca ctg act cca acc atg gga tgg      48
Met Ser Ser Pro Gln Thr Leu Asn Thr Leu Thr Pro Thr Met Gly Trp
1               5                  10                  15 agc tgg atc ttt ctc ttt ctc ttg tca gga act gga ggt gtc ctc tct      96
Ser Trp Ile Phe Leu Phe Leu Leu Ser Gly Thr Gly Gly Val Leu Ser
            20                  25                  30 gag gtc caa ctg caa cag tct gga cct gag ctg gtg aag cct ggg gct     144
Glu Val Gln Leu Gln Gln Ser Gly Pro Glu Leu Val Lys Pro Gly Ala
        35                  40                  45 tca gtg aag atg tcc tgc aag gct tct gga tac acc ttc act gac tac     192
Ser Val Lys Met Ser Cys Lys Ala Ser Gly Tyr Thr Phe Thr Asp Tyr
    50                  55                  60 tac atg aag tgg gtg aag cag agc cat ggg aag agc ctt gag tgg att     240
Tyr Met Lys Trp Val Lys Gln Ser His Gly Lys Ser Leu Glu Trp Ile
65                  70                  75                  80 gga gat ctt aat cct aac aat ggt gat act ttc tac aac cag aag ttc     288
Gly Asp Leu Asn Pro Asn Asn Gly Asp Thr Phe Tyr Asn Gln Lys Phe
                85                  90                  95 aag ggc aag gcc aca ttg act gta gac aag tcc tcc agc aca gcc tac     336
Lys Gly Lys Ala Thr Leu Thr Val Asp Lys Ser Ser Ser Thr Ala Tyr
            100                 105                 110 atc cag ctc aac agc ctg aca tct gag gac tct gca gtc tat tac tgt     384
Ile Gln Leu Asn Ser Leu Thr Ser Glu Asp Ser Ala Val Tyr Tyr Cys
        115                 120                 125 gca aga gag gcg gga agt tcc ttc ggt agt agc tgt aat tat tgg ggc     432
Ala Arg Glu Ala Gly Ser Ser Phe Gly Ser Ser Cys Asn Tyr Trp Gly
    130                 135                 140 caa ggc acc act ctc aca gtc tcc tca gcc aaa aca acg gcc cca tct     480
Gln Gly Thr Thr Leu Thr Val Ser Ser Ala Lys Thr Thr Ala Pro Ser
145                 150                 155                 160 gtc tat cca ctg gcc aat cga att ccc gcg gcc gcc atg gcg gcc ggg     528
Val Tyr Pro Leu Ala Asn Arg Ile Pro Ala Ala Ala Met Ala Ala Gly
                165                 170                 175 agc atg cga cgt cgg gcc caa ttc gcc cta tag                          561
Ser Met Arg Arg Arg Ala Gln Phe Ala Leu
            180                 185
```

<210> SEQ ID NO 5
<211> LENGTH: 186
<212> TYPE: PRT
<213> ORGANISM: Artificial Sequence
<220> FEATURE:
<223> OTHER INFORMATION: Synthetic Construct

<400> SEQUENCE: 5

```
Met Ser Ser Pro Gln Thr Leu Asn Thr Leu Thr Pro Thr Met Gly Trp
1               5                  10                  15

Ser Trp Ile Phe Leu Phe Leu Leu Ser Gly Thr Gly Gly Val Leu Ser
            20                  25                  30

Glu Val Gln Leu Gln Gln Ser Gly Pro Glu Leu Val Lys Pro Gly Ala
        35                  40                  45

Ser Val Lys Met Ser Cys Lys Ala Ser Gly Tyr Thr Phe Thr Asp Tyr
    50                  55                  60

Tyr Met Lys Trp Val Lys Gln Ser His Gly Lys Ser Leu Glu Trp Ile
65                  70                  75                  80
```

```
Gly Asp Leu Asn Pro Asn Asn Gly Asp Thr Phe Tyr Asn Gln Lys Phe
                85                  90                  95

Lys Gly Lys Ala Thr Leu Thr Val Asp Lys Ser Ser Thr Ala Tyr
            100                 105                 110

Ile Gln Leu Asn Ser Leu Thr Ser Glu Asp Ser Ala Val Tyr Tyr Cys
        115                 120                 125

Ala Arg Glu Ala Gly Ser Ser Phe Gly Ser Ser Cys Asn Tyr Trp Gly
130                 135                 140

Gln Gly Thr Thr Leu Thr Val Ser Ser Ala Lys Thr Thr Ala Pro Ser
145                 150                 155                 160

Val Tyr Pro Leu Ala Asn Arg Ile Pro Ala Ala Met Ala Ala Gly
                165                 170                 175

Ser Met Arg Arg Arg Ala Gln Phe Ala Leu
            180                 185

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccatctgtct atccactggc c                                              21

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Val Val Met Thr Gln Thr Pro Lys Phe Leu Leu Val Ser Ala Gly
1               5                   10                  15

Asp Arg Val Thr Ile Thr Cys Lys Ala Ser Gln Thr Val Ser Lys Asp
            20                  25                  30

Val Ala Trp Tyr Gln Gln Gln Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105

<210> SEQ ID NO 8
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(708)
<220> FEATURE:
```

<221> NAME/KEY: modified_base
<222> LOCATION: (697)..(697)
<223> OTHER INFORMATION: a, c, t or g
<220> FEATURE:
<221> NAME/KEY: misc_feature
<222> LOCATION: (697)..(697)
<223> OTHER INFORMATION: n is a, c, g, or t

<400> SEQUENCE: 8

```
atg aag tca cag acc cag gtc ttc gta ttt cta ctg ctc tgt gtg tct        48
Met Lys Ser Gln Thr Gln Val Phe Val Phe Leu Leu Leu Cys Val Ser
1               5                   10                  15 gga gtt cat ggg agt gtt gtg atg acc cag act ccc aag ttc ctg ctt        96
Gly Val His Gly Ser Val Val Met Thr Gln Thr Pro Lys Phe Leu Leu
                20                  25                  30 gtg tca gcg gga gac agg gtt acc ata acc tgc aag gcc agt cag act       144
Val Ser Ala Gly Asp Arg Val Thr Ile Thr Cys Lys Ala Ser Gln Thr
            35                  40                  45 gtg agt aaa gat gta gct tgg tac caa cag cag cca ggg cag tct cct       192
Val Ser Lys Asp Val Ala Trp Tyr Gln Gln Gln Pro Gly Gln Ser Pro
        50                  55                  60 aaa ctg ctg ata tac tat gca tcc aat cgc tac act gga gtc cct gat       240
Lys Leu Leu Ile Tyr Tyr Ala Ser Asn Arg Tyr Thr Gly Val Pro Asp
65                  70                  75                  80 cgc ttc act ggc agt gga tat ggg acg gat ttc act ttc acc atc agc       288
Arg Phe Thr Gly Ser Gly Tyr Gly Thr Asp Phe Thr Phe Thr Ile Ser
                85                  90                  95 act gtg cag gct gaa gac ctg gca gtt tat ttc tgt cag cag gat tat       336
Thr Val Gln Ala Glu Asp Leu Ala Val Tyr Phe Cys Gln Gln Asp Tyr
                100                 105                 110 agc tct ccg tac acg ttc ggc ggg ggg acc aag ctg gaa ata aaa cgg       384
Ser Ser Pro Tyr Thr Phe Gly Gly Gly Thr Lys Leu Glu Ile Lys Arg
            115                 120                 125 gct gat gct gca cca act gta tcc atc ttc cca cca tcc agt gag cag       432
Ala Asp Ala Ala Pro Thr Val Ser Ile Phe Pro Pro Ser Ser Glu Gln
130                 135                 140 tta aca tct gga ggt gcc tca gtc gtg tgc ttc ttg aac aac ttc tac       480
Leu Thr Ser Gly Gly Ala Ser Val Val Cys Phe Leu Asn Asn Phe Tyr
145                 150                 155                 160 ccc aga gac atc aat gtc aag tgg aag att gat ggc agt gaa cga caa       528
Pro Arg Asp Ile Asn Val Lys Trp Lys Ile Asp Gly Ser Glu Arg Gln
                165                 170                 175 aat ggt gtc ctg aac agt tgg act gat cag gac agc aaa gac agc acc       576
Asn Gly Val Leu Asn Ser Trp Thr Asp Gln Asp Ser Lys Asp Ser Thr
            180                 185                 190 tac agc atg agc agc acc ctc aca ttg acc aag gac gag tat gaa cga       624
Tyr Ser Met Ser Ser Thr Leu Thr Leu Thr Lys Asp Glu Tyr Glu Arg
        195                 200                 205 cat aac agc tat acc tgt gag gcc act cac aag aca tca act tca ccc       672
His Asn Ser Tyr Thr Cys Glu Ala Thr His Lys Thr Ser Thr Ser Pro
    210                 215                 220 atc gtc aag agc ttc aac agg aat nag tgt aat cac tag                   711
Ile Val Lys Ser Phe Asn Arg Asn Xaa Cys Asn His
225                 230                 235
```

<210> SEQ ID NO 9
<211> LENGTH: 236
<212> TYPE: PRT
<213> ORGANISM: Artificial Sequence
<220> FEATURE:
<221> NAME/KEY: misc_feature
<222> LOCATION: (233)..(233)
<223> OTHER INFORMATION: The 'Xaa' at location 233 stands for Lys, Glu, or Gln.
<220> FEATURE:
<223> OTHER INFORMATION: Synthetic Construct

<400> SEQUENCE: 9

```
Met Lys Ser Gln Thr Gln Val Phe Val Phe Leu Leu Leu Cys Val Ser
1               5                   10                  15

Gly Val His Gly Ser Val Val Met Thr Gln Thr Pro Lys Phe Leu Leu
            20                  25                  30

Val Ser Ala Gly Asp Arg Val Thr Ile Thr Cys Lys Ala Ser Gln Thr
        35                  40                  45

Val Ser Lys Asp Val Ala Trp Tyr Gln Gln Pro Gly Gln Ser Pro
    50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Xaa Cys Asn His
225                 230                 235
```

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Val Gln Leu Lys Glu Ser Gly Pro Gly Leu Leu Ala Pro Ser Gln
1               5                   10                  15

Ser Leu Ser Ile Thr Cys Thr Val Ser Gly Phe Ser Leu Thr Ser Tyr
            20                  25                  30

Gly Val Tyr Trp Val Arg Gln Pro Pro Gly Lys Gly Leu Glu Trp Leu
        35                  40                  45

Gly Ile Ile Trp Gly Asp Gly Ser Thr Asn Tyr Gln Ser Val Leu Arg
    50                  55                  60

Ser Arg Leu Ser Ile Thr Lys Asp Asp Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95
```

```
Lys Arg Gly Asp Tyr Asp Val Ala Tyr Trp Gly Gln Gly Thr Leu Val
            100                 105                 110

Thr Val Ser Ala
    115

<210> SEQ ID NO 11
<211> LENGTH: 450
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(447)
<220> FEATURE:
<221> NAME/KEY: modified_base
<222> LOCATION: (436)..(437)
<223> OTHER INFORMATION: a, c, t or g
<220> FEATURE:
<221> NAME/KEY: misc_feature
<222> LOCATION: (436)..(437)
<223> OTHER INFORMATION: n is a, c, g, or t
<220> FEATURE:
<221> NAME/KEY: modified_base
<222> LOCATION: (440)..(440)
<223> OTHER INFORMATION: a, c, t or g
<220> FEATURE:
<221> NAME/KEY: misc_feature
<222> LOCATION: (440)..(440)
<223> OTHER INFORMATION: n is a, c, g, or t

<400> SEQUENCE: 11 atg gct gtc ctg gca ctg ctc ctc tgc ctg gtg aca ttc cca agg tgt       48
Met Ala Val Leu Ala Leu Leu Leu Cys Leu Val Thr Phe Pro Arg Cys
1               5                   10                  15 gtc ctg tcc cag gtg cag ctg aag gag tca gga cct ggc cta ctg gcg       96
Val Leu Ser Gln Val Gln Leu Lys Glu Ser Gly Pro Gly Leu Leu Ala
            20                  25                  30 ccc tca cag agc ctg tcc atc aca tgc act gtc tca ggt ttc tcg tta     144
Pro Ser Gln Ser Leu Ser Ile Thr Cys Thr Val Ser Gly Phe Ser Leu
        35                  40                  45 acc agc tat ggt gta tac tgg gtt cgc cag cct cca gga aag ggt ctg     192
Thr Ser Tyr Gly Val Tyr Trp Val Arg Gln Pro Pro Gly Lys Gly Leu
    50                  55                  60 gag tgg ctg gga atc ata tgg ggt gac ggg agc aca aat tat caa tca     240
Glu Trp Leu Gly Ile Ile Trp Gly Asp Gly Ser Thr Asn Tyr Gln Ser
65                  70                  75                  80 gtt ctc aga tcc aga ctg agc atc acc aag gat gac tcc aag agc caa     288
Val Leu Arg Ser Arg Leu Ser Ile Thr Lys Asp Asp Ser Lys Ser Gln
                85                  90                  95 gtt ttc tta aaa ctg aac agt cta caa act gat gac aca gcc acg tac     336
Val Phe Leu Lys Leu Asn Ser Leu Gln Thr Asp Asp Thr Ala Thr Tyr
            100                 105                 110 tac tgt gcc aaa cgg ggg gat tac gac gtt gct tac tgg ggc caa ggg     384
Tyr Cys Ala Lys Arg Gly Asp Tyr Asp Val Ala Tyr Trp Gly Gln Gly
        115                 120                 125 act ctg gtc act gtc tct gca gcc aaa acg aca ccc cca tct gtc tat     432
Thr Leu Val Thr Val Ser Ala Ala Lys Thr Thr Pro Pro Ser Val Tyr
    130                 135                 140 cct nna gnc aat cac tag                                              450
Pro Xaa Xaa Asn His
145

<210> SEQ ID NO 12
```

```
<211> LENGTH: 149
<212> TYPE: PRT
<213> ORGANISM: Artificial Sequence
<220> FEATURE:
<221> NAME/KEY: misc_feature
<222> LOCATION: (146)..(146)
<223> OTHER INFORMATION: The 'Xaa' at location 146 stands for Lys, Arg,
      Thr, Ile, Glu, Gly, Ala, Val, Gln, Pro, Leu, or Ser.
<220> FEATURE:
<221> NAME/KEY: misc_feature
<222> LOCATION: (147)..(147)
<223> OTHER INFORMATION: The 'Xaa' at location 147 stands for Asp, Gly,
      Ala, or Val.
<220> FEATURE:
<223> OTHER INFORMATION: Synthetic Construct

<400> SEQUENCE: 12

Met Ala Val Leu Ala Leu Leu Cys Leu Val Thr Phe Pro Arg Cys
1               5                   10                  15

Val Leu Ser Gln Val Gln Leu Lys Glu Ser Gly Pro Gly Leu Leu Ala
            20                  25                  30

Pro Ser Gln Ser Leu Ser Ile Thr Cys Thr Val Ser Gly Phe Ser Leu
        35                  40                  45

Thr Ser Tyr Gly Val Tyr Trp Val Arg Gln Pro Pro Gly Lys Gly Leu
    50                  55                  60

Glu Trp Leu Gly Ile Ile Trp Gly Asp Gly Ser Thr Asn Tyr Gln Ser
65                  70                  75                  80

Val Leu Arg Ser Arg Leu Ser Ile Thr Lys Asp Ser Lys Ser Gln
                85                  90                  95

Val Phe Leu Lys Leu Asn Ser Leu Gln Thr Asp Thr Ala Thr Tyr
            100                 105                 110

Tyr Cys Ala Lys Arg Gly Asp Tyr Asp Val Ala Tyr Trp Gly Gln Gly
        115                 120                 125

Thr Leu Val Thr Val Ser Ala Ala Lys Thr Thr Pro Pro Ser Val Tyr
    130                 135                 140

Pro Xaa Xaa Asn His
145

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccatctgtct at                                                        12

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Leu Thr Gln Ser Pro Ala Ser Leu Ala Val Ser Leu Gly
1               5                   10                  15

Gln Arg Ala Ile Ile Ser Cys Lys Ala Ser Gln Thr Val Ser Glu Val
            20                  25                  30

Gly Thr Ser Leu Met His Trp Tyr Gln Gln Arg Pro Gly Gln Gln Pro
```

```
                35                  40                  45
Lys Leu Leu Ile Tyr Arg Thr Ser Asn Leu Glu Ala Gly Val Pro Thr
     50                  55                  60

Arg Phe Ser Gly Ser Gly Ser Arg Thr Asp Phe Thr Leu Asn Ile His
 65                  70                  75                  80

Pro Val Glu Glu Asp Asp Ala Ala Thr Tyr Tyr Cys Gln Gln Ser Arg
                 85                  90                  95

Glu Phe Pro Trp Thr Phe Gly Gly Gly Thr Arg Leu Glu Ile Lys
            100                 105                 110
```

<210> SEQ ID NO 15
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(720)
<220> FEATURE:
<221> NAME/KEY: modified_base
<222> LOCATION: (5)..(5)
<223> OTHER INFORMATION: a, c, t or g
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (12)..(12)
<223> OTHER INFORMATION: a, c, t or g
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (15)..(15)
<223> OTHER INFORMATION: a, c, t or g
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (24)..(24)
<223> OTHER INFORMATION: a, c, t or g
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, t or g
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (665)..(665)
<223> OTHER INFORMATION: a, c, t or g
<220> FEATURE:
<221> NAME/KEY: misc_feature
<222> LOCATION: (665)..(665)
<223> OTHER INFORMATION: n is a, c, g, or t

<400> SEQUENCE: 15

```
atg gng act can tcn ctg ctg ctn tnn gtg cta ctg ctc tgg gtt cca    48
Met Xaa Thr Xaa Xaa Leu Leu Xaa Xaa Val Leu Leu Leu Trp Val Pro
 1               5                  10                  15
```

```
ggc tcc act ggt gac att gtg ctg acc caa tct cca gct tct ttg gct    96
Gly Ser Thr Gly Asp Ile Val Leu Thr Gln Ser Pro Ala Ser Leu Ala
         20                  25                  30 gtg tct cta ggg cag agg gcc atc atc tcc tgc aag gcc agc caa act   144
Val Ser Leu Gly Gln Arg Ala Ile Ile Ser Cys Lys Ala Ser Gln Thr
     35                  40                  45 gtc agt ttt gtt ggg act agt tta atg cac tgg tat caa cag aga cca   192
Val Ser Phe Val Gly Thr Ser Leu Met His Trp Tyr Gln Gln Arg Pro
 50                  55                  60 gga cag caa ccc aaa ctc ctc atc tat cgt aca tcc aac cta gaa gct   240
Gly Gln Gln Pro Lys Leu Leu Ile Tyr Arg Thr Ser Asn Leu Glu Ala
65                  70                  75                  80 ggg gtt cca acc agg ttt agt ggc agt ggg tct agg aca gac ttc acc   288
Gly Val Pro Thr Arg Phe Ser Gly Ser Gly Ser Arg Thr Asp Phe Thr
                 85                  90                  95 ctc aat atc cat cct gtg gag gaa gat gat gct gca acc tat tac tgt   336
Leu Asn Ile His Pro Val Glu Glu Asp Asp Ala Ala Thr Tyr Tyr Cys
            100                 105                 110 cag caa agt agg gaa ttt ccg tgg acg ttc ggt gga ggc acc agg ctg   384
Gln Gln Ser Arg Glu Phe Pro Trp Thr Phe Gly Gly Gly Thr Arg Leu
        115                 120                 125 gaa atc aaa cgg gct gat gct gca cca act gta tcc atc ttc cca cca   432
Glu Ile Lys Arg Ala Asp Ala Ala Pro Thr Val Ser Ile Phe Pro Pro
    130                 135                 140 tcc agt gag cag tta aca tct gga ggt gcc tca gtc gtg tgc ttc ttg   480
Ser Ser Glu Gln Leu Thr Ser Gly Gly Ala Ser Val Val Cys Phe Leu
145                 150                 155                 160 aac aac ttc tac ccc aga gac atc aat gtc aag tgg aag att gat ggc   528
Asn Asn Phe Tyr Pro Arg Asp Ile Asn Val Lys Trp Lys Ile Asp Gly
                165                 170                 175 agt gaa cga caa aat ggt gtc ctg aac agt tgg act gat cag gac agc   576
Ser Glu Arg Gln Asn Gly Val Leu Asn Ser Trp Thr Asp Gln Asp Ser
            180                 185                 190 aaa gac agc acc tac agc atg agc agc acc ctc aca ttg acc aag gac   624
Lys Asp Ser Thr Tyr Ser Met Ser Ser Thr Leu Thr Leu Thr Lys Asp
        195                 200                 205 gag tat gaa cga cat aac agc tat acc tgt gag gcc act cnc aag aca   672
Glu Tyr Glu Arg His Asn Ser Tyr Thr Cys Glu Ala Thr Xaa Lys Thr
    210                 215                 220 tca act tca ccc atc gtc aag agc ttc aac agg aat gag tgt aat cac   720
Ser Thr Ser Pro Ile Val Lys Ser Phe Asn Arg Asn Glu Cys Asn His
225                 230                 235                 240 tag                                                                723

<210> SEQ ID NO 16
<211> LENGTH: 240
<212> TYPE: PRT
<213> ORGANISM: Artificial Sequence
<220> FEATURE:
<221> NAME/KEY: misc_feature
<222> LOCATION: (2)..(2)
<223> OTHER INFORMATION: The 'Xaa' at location 2 stands for Glu, Gly,
      Ala, or Val.
<220> FEATURE:
<221> NAME/KEY: misc_feature
<222> LOCATION: (4)..(4)
<223> OTHER INFORMATION: The 'Xaa' at location 4 stands for Gln, or His.
<220> FEATURE:
<221> NAME/KEY: misc_feature
<222> LOCATION: (5)..(5)
<223> OTHER INFORMATION: The 'Xaa' at location 5 stands for Ser.
<220> FEATURE:
<221> NAME/KEY: misc_feature
```

<222> LOCATION: (8)..(8)
<223> OTHER INFORMATION: The 'Xaa' at location 8 stands for Leu.
<220> FEATURE:
<221> NAME/KEY: misc_feature
<222> LOCATION: (9)..(9)
<223> OTHER INFORMATION: The 'Xaa' at location 9 stands for Tyr, Trp, Cys, Ser, Leu, or Phe.
<220> FEATURE:
<221> NAME/KEY: misc_feature
<222> LOCATION: (222)..(222)
<223> OTHER INFORMATION: The 'Xaa' at location 222 stands for His, Arg, Pro, or Leu.
<220> FEATURE:
<223> OTHER INFORMATION: Synthetic Construct

<400> SEQUENCE: 16

Met Xaa Thr Xaa Xaa Leu Leu Xaa Xaa Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Ile Ile Ser Cys Lys Ala Ser Gln Thr
        35                  40                  45

Val Ser Phe Val Gly Thr Ser Leu Met His Trp Tyr Gln Gln Arg Pro
50                  55                  60

Gly Gln Gln Pro Lys Leu Leu Ile Tyr Arg Thr Ser Asn Leu Glu Ala
65                  70                  75                  80

Gly Val Pro Thr Arg Phe Ser Gly Ser Gly Ser Arg Thr Asp Phe Thr
                85                  90                  95

Leu Asn Ile His Pro Val Glu Glu Asp Asp Ala Ala Thr Tyr Tyr Cys
            100                 105                 110

Gln Gln Ser Arg Glu Phe Pro Trp Thr Phe Gly Gly Gly Thr Arg Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr Xaa Lys Thr
    210                 215                 220

Ser Thr Ser Pro Ile Val Lys Ser Phe Asn Arg Asn Glu Cys Asn His
225                 230                 235                 240

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

```
Trp Met Asn Trp Val Arg Gln Pro Glu Lys Gly Leu Glu Trp Val
        35                  40                  45

Ala Glu Ile Arg Leu Asn Ser Asn Asn Tyr Ala Thr His Tyr Ala Glu
 50                  55                  60

Ser Val Lys Gly Lys Phe Thr Ile Ser Arg Asp Asp Ser Lys Ser Ser
 65                  70                  75                  80

Val Tyr Leu Gln Met Asn Asp Leu Arg Ala Glu Asp Thr Gly Ile Tyr
                     85                  90                  95

Tyr Cys Thr Arg Asn Trp Asp Phe Ala Trp Phe Asp Ser Trp Gly Gln
                100                 105                 110

Gly Thr Leu Val Thr Val Ser Ala
            115                 120

<210> SEQ ID NO 18
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(588)

<400> SEQUENCE: 18 atg ggg aga cgc aca acc ctg gac tca caa gtc ttt ctc ttc agt gac      48
Met Gly Arg Arg Thr Thr Leu Asp Ser Gln Val Phe Leu Phe Ser Asp
 1               5                  10                  15 aaa cac aga aat aga aca ttc acc atg tac ttg gga ctg aac tgt gta      96
Lys His Arg Asn Arg Thr Phe Thr Met Tyr Leu Gly Leu Asn Cys Val
                20                  25                  30 ttc ata gtt ttt ctc tta aaa ggt gtc cag agt gaa gtg aag ctt gag     144
Phe Ile Val Phe Leu Leu Lys Gly Val Gln Ser Glu Val Lys Leu Glu
             35                  40                  45 gag tct gga gga ggc ttg gtg caa cct gga gga tcc atg aaa ctc tcc     192
Glu Ser Gly Gly Gly Leu Val Gln Pro Gly Gly Ser Met Lys Leu Ser
 50                  55                  60 tgt gtt gcc tct gga ttc act ttc agt aac tac tgg atg aac tgg gtc     240
Cys Val Ala Ser Gly Phe Thr Phe Ser Asn Tyr Trp Met Asn Trp Val
 65                  70                  75                  80 cgc caa cct cca gag aag ggg ctt gaa tgg gtt gct gaa att aga ttg     288
Arg Gln Pro Pro Glu Lys Gly Leu Glu Trp Val Ala Glu Ile Arg Leu
                 85                  90                  95 aac tct aat aat tat gca aca cat tat gcg gag tct gtg aaa ggg aaa     336
Asn Ser Asn Asn Tyr Ala Thr His Tyr Ala Glu Ser Val Lys Gly Lys
            100                 105                 110 ttc acc atc tca aga gat gat tcc aaa agt agt gtc tac ctg caa atg     384
Phe Thr Ile Ser Arg Asp Asp Ser Lys Ser Ser Val Tyr Leu Gln Met
        115                 120                 125 aac gac tta aga gct gaa gac act ggc att tat tac tgt acc aga aac     432
Asn Asp Leu Arg Ala Glu Asp Thr Gly Ile Tyr Tyr Cys Thr Arg Asn
    130                 135                 140 tgg gac ttt gcc tgg ttt gat tcc tgg ggc caa ggg act ctg gtc act     480
Trp Asp Phe Ala Trp Phe Asp Ser Trp Gly Gln Gly Thr Leu Val Thr
145                 150                 155                 160 gtc tct gca gcc aaa aca aca gcc cca tct gtc tat cca ctg gcc aat     528
Val Ser Ala Ala Lys Thr Thr Ala Pro Ser Val Tyr Pro Leu Ala Asn
                165                 170                 175 cga att ccc gcg gcc gcc atg gcg gcc ggg agc atg cga cgt cgg gcc     576
Arg Ile Pro Ala Ala Ala Met Ala Ala Gly Ser Met Arg Arg Arg Ala
            180                 185                 190
```

```
caa ttc gcc cta tag                                              591
Gln Phe Ala Leu
        195

<210> SEQ ID NO 19
<211> LENGTH: 196
<212> TYPE: PRT
<213> ORGANISM: Artificial Sequence
<220> FEATURE:
<223> OTHER INFORMATION: Synthetic Construct

<400> SEQUENCE: 19

Met Gly Arg Arg Thr Thr Leu Asp Ser Gln Val Phe Leu Phe Ser Asp
1               5                   10                  15

Lys His Arg Asn Arg Thr Phe Thr Met Tyr Leu Gly Leu Asn Cys Val
            20                  25                  30

Phe Ile Val Phe Leu Leu Lys Gly Val Gln Ser Glu Val Lys Leu Glu
        35                  40                  45

Glu Ser Gly Gly Gly Leu Val Gln Pro Gly Gly Ser Met Lys Leu Ser
    50                  55                  60

Cys Val Ala Ser Gly Phe Thr Phe Ser Asn Tyr Trp Met Asn Trp Val
65                  70                  75                  80

Arg Gln Pro Pro Glu Lys Gly Leu Glu Trp Val Ala Glu Ile Arg Leu
                85                  90                  95

Asn Ser Asn Asn Tyr Ala Thr His Tyr Ala Glu Ser Val Lys Gly Lys
            100                 105                 110

Phe Thr Ile Ser Arg Asp Asp Ser Lys Ser Ser Val Tyr Leu Gln Met
        115                 120                 125

Asn Asp Leu Arg Ala Glu Asp Thr Gly Ile Tyr Tyr Cys Thr Arg Asn
    130                 135                 140

Trp Asp Phe Ala Trp Phe Asp Ser Trp Gly Gln Gly Thr Leu Val Thr
145                 150                 155                 160

Val Ser Ala Ala Lys Thr Thr Ala Pro Ser Val Tyr Pro Leu Ala Asn
                165                 170                 175

Arg Ile Pro Ala Ala Ala Met Ala Ala Gly Ser Met Arg Arg Arg Ala
            180                 185                 190

Gln Phe Ala Leu
        195

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Val
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80
```

Glu Asp Leu Ala Leu Tyr Tyr Cys Gln Gln His Tyr Thr Thr Pro Phe
            85                  90                  95

Thr Phe Gly Ser Gly Thr Lys Leu Glu Ile Lys
            100                 105

<210> SEQ ID NO 21
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(744)

<400> SEQUENCE: 21

```
atg ggg gaa atg cat cgc acc agc atg ggc atc aag atg gag tca cag        48
Met Gly Glu Met His Arg Thr Ser Met Gly Ile Lys Met Glu Ser Gln
1               5                   10                  15 att cag gca ttt gta ttc gtg ttt ctc tgg ttg tct ggt gtt gac gga        96
Ile Gln Ala Phe Val Phe Val Phe Leu Trp Leu Ser Gly Val Asp Gly
                20                  25                  30 gac att gtg atg acc cag tct cac aaa ttc atg tcc aca tca gta gga       144
Asp Ile Val Met Thr Gln Ser His Lys Phe Met Ser Thr Ser Val Gly
            35                  40                  45 gac agg gtc agc atc acc tgc aag gcc agt caa gat gtg agt act gtt       192
Asp Arg Val Ser Ile Thr Cys Lys Ala Ser Gln Asp Val Ser Thr Val
        50                  55                  60 gtg gcc tgg tat caa caa aaa cca ggg caa tct cct aaa cta ctg att       240
Val Ala Trp Tyr Gln Gln Lys Pro Gly Gln Ser Pro Lys Leu Leu Ile
65                  70                  75                  80 tac tgg gca tcc acc cgg cac act gga gtc cct gat cgc ttc aca ggc       288
Tyr Trp Ala Ser Thr Arg His Thr Gly Val Pro Asp Arg Phe Thr Gly
                85                  90                  95 agt gga tct ggg aca gat tat act ctc acc atc agc agt gtg cag gct       336
Ser Gly Ser Gly Thr Asp Tyr Thr Leu Thr Ile Ser Ser Val Gln Ala
            100                 105                 110 gaa gac ctg gca ctt tat tac tgt cag caa cat tat acc act cca ttc       384
Glu Asp Leu Ala Leu Tyr Tyr Cys Gln Gln His Tyr Thr Thr Pro Phe
        115                 120                 125 acg ttc ggc tcg ggg aca aag ttg gaa ata aaa cgg gct gat gct gca       432
Thr Phe Gly Ser Gly Thr Lys Leu Glu Ile Lys Arg Ala Asp Ala Ala
    130                 135                 140 cca act gta tcc atc ttc cca cca tcc agt gag cag tta aca tct gga       480
Pro Thr Val Ser Ile Phe Pro Pro Ser Ser Glu Gln Leu Thr Ser Gly
145                 150                 155                 160 ggt gcc tca gtc gtg tgc ttc ttg aac aac ttc tac ccc aga gac atc       528
Gly Ala Ser Val Val Cys Phe Leu Asn Asn Phe Tyr Pro Arg Asp Ile
                165                 170                 175 aat gtc aag tgg aag att gat ggc agt gaa cga caa aat ggt gtc ctg       576
Asn Val Lys Trp Lys Ile Asp Gly Ser Glu Arg Gln Asn Gly Val Leu
            180                 185                 190 aac agt tgg act gat cag gac agc aaa gac agc acc tac agc atg agc       624
Asn Ser Trp Thr Asp Gln Asp Ser Lys Asp Ser Thr Tyr Ser Met Ser
        195                 200                 205 agc acc ctc aca ttg acc aag gac gag tat gaa cga cat aac agc tat       672
Ser Thr Leu Thr Leu Thr Lys Asp Glu Tyr Glu Arg His Asn Ser Tyr
    210                 215                 220 acc tgt gag gcc act cac aag aca tca act tca ccc atc gtc aag agc       720
Thr Cys Glu Ala Thr His Lys Thr Ser Thr Ser Pro Ile Val Lys Ser
```

```
                225                 230                 235                 240 ttc aac agg aat gag tgt aat cac tag                                      747
Phe Asn Arg Asn Glu Cys Asn His
                245
```

<210> SEQ ID NO 22
<211> LENGTH: 248
<212> TYPE: PRT
<213> ORGANISM: Artificial Sequence
<220> FEATURE:
<223> OTHER INFORMATION: Synthetic Construct

<400> SEQUENCE: 22

```
Met Gly Glu Met His Arg Thr Ser Met Gly Ile Lys Met Glu Ser Gln
1               5                   10                  15

Ile Gln Ala Phe Val Phe Val Phe Leu Trp Leu Ser Gly Val Asp Gly
            20                  25                  30

Asp Ile Val Met Thr Gln Ser His Lys Phe Met Ser Thr Ser Val Gly
        35                  40                  45

Asp Arg Val Ser Ile Thr Cys Lys Ala Ser Gln Asp Val Ser Thr Val
    50                  55                  60

Val Ala Trp Tyr Gln Gln Lys Pro Gly Gln Ser Pro Lys Leu Leu Ile
65                  70                  75                  80

Tyr Trp Ala Ser Thr Arg His Thr Gly Val Pro Asp Arg Phe Thr Gly
                85                  90                  95

Ser Gly Ser Gly Thr Asp Tyr Thr Leu Thr Ile Ser Ser Val Gln Ala
            100                 105                 110

Glu Asp Leu Ala Leu Tyr Tyr Cys Gln Gln His Tyr Thr Thr Pro Phe
        115                 120                 125

Thr Phe Gly Ser Gly Thr Lys Leu Glu Ile Lys Arg Ala Asp Ala Ala
    130                 135                 140

Pro Thr Val Ser Ile Phe Pro Pro Ser Ser Glu Gln Leu Thr Ser Gly
145                 150                 155                 160

Gly Ala Ser Val Val Cys Phe Leu Asn Asn Phe Tyr Pro Arg Asp Ile
                165                 170                 175

Asn Val Lys Trp Lys Ile Asp Gly Ser Glu Arg Gln Asn Gly Val Leu
            180                 185                 190

Asn Ser Trp Thr Asp Gln Asp Ser Lys Asp Ser Thr Tyr Ser Met Ser
        195                 200                 205

Ser Thr Leu Thr Leu Thr Lys Asp Glu Tyr Glu Arg His Asn Ser Tyr
    210                 215                 220

Thr Cys Glu Ala Thr His Lys Thr Ser Thr Ser Pro Ile Val Lys Ser
225                 230                 235                 240

Phe Asn Arg Asn Glu Cys Asn His
                245
```

<210> SEQ ID NO 23
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Ser Ser Pro Gln Thr Leu Asn Thr Leu Thr Pro Thr Met Gly Trp
1               5                   10                  15

Ser Trp Ile Phe Leu Phe Leu Leu Ser Gly Thr Gly Gly Val Leu Ser
```

-continued

```
            20                  25                  30
Glu Val Gln Leu Gln Gln Ser Gly Pro Glu Leu Val Lys Pro Gly Ala
            35                  40                  45
Ser Val Lys Met Ser Cys Lys Ala Ser Gly Tyr Thr Phe Thr Asp Tyr
        50                  55                  60
Tyr Met Lys Trp Val Lys Gln Ser His Gly Lys Ser Leu Glu Trp Ile
 65                  70                  75                  80
Gly Asp Leu Asn Pro Asn Asn Gly Asp Thr Phe Tyr Asn Gln Lys Phe
                85                  90                  95
Lys Gly Lys Ala Thr Leu Thr Val Asp Lys Ser Ser Thr Ala Tyr
            100                 105                 110
Ile Gln Leu Asn Ser Leu Thr Ser Glu Asp Ser Ala Val Tyr Tyr Cys
            115                 120                 125
Ala Arg Glu Ala Gly Ser Ser Phe Gly Ser Ser Cys Asn Tyr Trp Gly
            130                 135                 140
Gln Gly Thr Thr Leu Thr Val Ser Ala Ser Thr Lys Gly Pro Ser Val
145                 150                 155                 160
Phe Pro Leu Ala Pro Ser Ser Lys Ser Thr Ser Gly Gly Thr Ala Ala
                165                 170                 175
Leu Gly Cys Leu Val Lys Asp Tyr Phe Pro Glu Pro Val Thr Val Ser
            180                 185                 190
Trp Asn Ser Gly Ala Leu Thr Ser Gly Val His Thr Phe Pro Ala Val
            195                 200                 205
Leu Gln Ser Ser Gly Leu Tyr Ser Leu Ser Ser Val Val Thr Val Pro
            210                 215                 220
Ser Ser Ser Leu Gly Thr Gln Thr Tyr Ile Cys Asn Val Asn His Lys
225                 230                 235                 240
Pro Ser Asn Thr Lys Val Asp Lys Lys Val Glu Pro Lys Ser Cys Asp
                245                 250                 255
Lys Thr His Thr Cys Pro Pro Cys Pro Ala Pro Glu Leu Leu Gly Gly
            260                 265                 270
Pro Ser Val Phe Leu Phe Pro Pro Lys Pro Lys Asp Thr Leu Met Ile
            275                 280                 285
Ser Arg Thr Pro Glu Val Thr Cys Val Val Val Asp Val Ser His Glu
            290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
            340                 345                 350
Glu Tyr Lys Cys Lys Val Ser Asn Lys Ala Leu Pro Ala Pro Ile Glu
            355                 360                 365
Lys Thr Ile Ser Lys Ala Lys Gly Gln Pro Arg Glu Pro Gln Val Tyr
            370                 375                 380
Thr Leu Pro Pro Ser Arg Glu Glu Met Thr Lys Asn Gln Val Ser Leu
385                 390                 395                 400
Thr Cys Leu Val Lys Gly Phe Tyr Pro Ser Asp Ile Ala Val Glu Trp
                405                 410                 415
Glu Ser Asn Gly Gln Pro Glu Asn Asn Tyr Lys Thr Thr Pro Pro Val
            420                 425                 430
Leu Asp Ser Asp Gly Ser Phe Phe Leu Tyr Ser Lys Leu Thr Val Asp
            435                 440                 445
```

```
Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys

<210> SEQ ID NO 24
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ser Ser Pro Gln Thr Leu Asn Thr Leu Thr Pro Thr Met Gly Trp
1               5                   10                  15

Ser Trp Ile Phe Leu Phe Leu Leu Ser Gly Thr Gly Gly Val Leu Ser
            20                  25                  30

Glu Val Gln Leu Gln Gln Ser Gly Pro Glu Leu Val Lys Pro Gly Ala
        35                  40                  45

Ser Val Lys Met Ser Cys Lys Ala Ser Gly Tyr Thr Phe Thr Asp Tyr
    50                  55                  60

Tyr Met Lys Trp Val Lys Gln Ser His Gly Lys Ser Leu Glu Trp Ile
65                  70                  75                  80

Gly Asp Leu Asn Pro Asn Asn Gly Asp Thr Phe Tyr Asn Gln Lys Phe
                85                  90                  95

Lys Gly Lys Ala Thr Leu Thr Val Asp Lys Ser Ser Ser Thr Ala Tyr
            100                 105                 110

Ile Gln Leu Asn Ser Leu Thr Ser Glu Asp Ser Ala Val Tyr Tyr Cys
        115                 120                 125

Ala Arg Glu Ala Gly Ser Ser Phe Gly Ser Ser Cys Asn Tyr Trp Gly
    130                 135                 140

Gln Gly Thr Thr Leu Thr Val Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Asn Phe Gly Thr Gln Thr Tyr Thr Cys Asn Val Asp His Lys
225                 230                 235                 240

Pro Ser Asn Thr Lys Val Asp Lys Thr Val Glu Arg Lys Cys Cys Val
                245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Gln Phe Asn Trp Tyr Val Asp Gly Val Glu Val His Asn Ala Lys Thr
305                 310                 315                 320
```

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
        355                 360                 365

Lys Thr Lys Gly Gln Pro Arg Glu Pro Gln Val Tyr Thr Leu Pro Pro
    370                 375                 380

Ser Arg Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Met Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 25
<211> LENGTH: 529
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ser Ser Pro Gln Thr Leu Asn Thr Leu Thr Pro Thr Met Gly Trp
1               5                   10                  15

Ser Trp Ile Phe Leu Phe Leu Leu Ser Gly Thr Gly Gly Val Leu Ser
            20                  25                  30

Glu Val Gln Leu Gln Gln Ser Gly Pro Glu Leu Val Lys Pro Gly Ala
        35                  40                  45

Ser Val Lys Met Ser Cys Lys Ala Ser Gly Tyr Thr Phe Thr Asp Tyr
    50                  55                  60

Tyr Met Lys Trp Val Lys Gln Ser His Gly Lys Ser Leu Glu Trp Ile
65                  70                  75                  80

Gly Asp Leu Asn Pro Asn Asn Gly Asp Thr Phe Tyr Asn Gln Lys Phe
                85                  90                  95

Lys Gly Lys Ala Thr Leu Thr Val Asp Lys Ser Ser Ser Thr Ala Tyr
            100                 105                 110

Ile Gln Leu Asn Ser Leu Thr Ser Glu Asp Ser Ala Val Tyr Tyr Cys
        115                 120                 125

Ala Arg Glu Ala Gly Ser Ser Phe Gly Ser Ser Cys Asn Tyr Trp Gly
    130                 135                 140

Gln Gly Thr Thr Leu Thr Val Ser Ala Ser Thr Lys Gly Pro Ser Val
145                 150                 155                 160

Phe Pro Leu Ala Pro Cys Ser Arg Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val

```
            195                 200                 205
Leu Gln Ser Ser Gly Leu Tyr Ser Leu Ser Val Thr Val Pro
    210                 215                 220
Ser Ser Ser Leu Gly Thr Gln Thr Tyr Thr Cys Asn Val Asn His Lys
225                 230                 235                 240
Pro Ser Asn Thr Lys Val Asp Lys Arg Val Glu Leu Lys Thr Pro Leu
                245                 250                 255
Gly Asp Thr Thr His Thr Cys Pro Arg Cys Pro Glu Pro Lys Ser Cys
                260                 265                 270
Asp Thr Pro Pro Pro Cys Pro Arg Cys Pro Glu Pro Lys Ser Cys Asp
            275                 280                 285
Thr Pro Pro Pro Cys Pro Arg Cys Pro Glu Pro Lys Ser Cys Asp Thr
        290                 295                 300
Pro Pro Pro Cys Pro Arg Cys Pro Ala Pro Glu Leu Leu Gly Gly Pro
305                 310                 315                 320
Ser Val Phe Leu Phe Pro Pro Lys Pro Lys Asp Thr Leu Met Ile Ser
                325                 330                 335
Arg Thr Pro Glu Val Thr Cys Val Val Val Asp Val Ser His Glu Asp
                340                 345                 350
Pro Glu Val Gln Phe Lys Trp Tyr Val Asp Gly Val Glu Val His Asn
            355                 360                 365
Ala Lys Thr Lys Pro Arg Glu Glu Gln Tyr Asn Ser Thr Phe Arg Val
        370                 375                 380
Val Ser Val Leu Thr Val Leu His Gln Asp Trp Leu Asn Gly Lys Glu
385                 390                 395                 400
Tyr Lys Cys Lys Val Ser Asn Lys Ala Leu Pro Ala Pro Ile Glu Lys
                405                 410                 415
Thr Ile Ser Lys Thr Lys Gly Gln Pro Arg Glu Pro Gln Val Tyr Thr
                420                 425                 430
Leu Pro Pro Ser Arg Glu Glu Met Thr Lys Asn Gln Val Ser Leu Thr
            435                 440                 445
Cys Leu Val Lys Gly Phe Tyr Pro Ser Asp Ile Ala Val Glu Trp Glu
        450                 455                 460
Ser Ser Gly Gln Pro Glu Asn Asn Tyr Asn Thr Thr Pro Pro Met Leu
465                 470                 475                 480
Asp Ser Asp Gly Ser Phe Phe Leu Tyr Ser Lys Leu Thr Val Asp Lys
                485                 490                 495
Ser Arg Trp Gln Gln Gly Asn Ile Phe Ser Cys Ser Val Met His Glu
                500                 505                 510
Ala Leu His Asn Arg Phe Thr Gln Lys Ser Leu Ser Leu Ser Pro Gly
            515                 520                 525
Lys

<210> SEQ ID NO 26
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ser Ser Pro Gln Thr Leu Asn Thr Leu Thr Pro Thr Met Gly Trp
1               5                   10                  15

Ser Trp Ile Phe Leu Phe Leu Leu Ser Gly Thr Gly Gly Val Leu Ser
```

```
                20                  25                  30
Glu Val Gln Leu Gln Gln Ser Gly Pro Glu Leu Val Lys Pro Gly Ala
            35                  40                  45

Ser Val Lys Met Ser Cys Lys Ala Ser Gly Tyr Thr Phe Thr Asp Tyr
    50                  55                  60

Tyr Met Lys Trp Val Lys Gln Ser His Gly Lys Ser Leu Glu Trp Ile
65                  70                  75                  80

Gly Asp Leu Asn Pro Asn Asn Gly Asp Thr Phe Tyr Asn Gln Lys Phe
                85                  90                  95

Lys Gly Lys Ala Thr Leu Thr Val Asp Lys Ser Ser Ser Thr Ala Tyr
            100                 105                 110

Ile Gln Leu Asn Ser Leu Thr Ser Glu Asp Ser Ala Val Tyr Tyr Cys
            115                 120                 125

Ala Arg Glu Ala Gly Ser Ser Phe Gly Ser Ser Cys Asn Tyr Trp Gly
        130                 135                 140

Gln Gly Thr Thr Leu Thr Val Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
        180                 185                 190

Trp Asn Ser Gly Ala Leu Thr Ser Gly Val His Thr Phe Pro Ala Val
            195                 200                 205

Leu Gln Ser Ser Gly Leu Tyr Ser Leu Ser Ser Val Val Thr Val Pro
        210                 215                 220

Ser Ser Ser Leu Gly Thr Lys Thr Tyr Thr Cys Asn Val Asp His Lys
225                 230                 235                 240

Pro Ser Asn Thr Lys Val Asp Lys Arg Val Glu Ser Lys Tyr Gly Pro
                245                 250                 255

Pro Cys Pro Ser Cys Pro Ala Pro Glu Phe Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445
```

Trp Gln Glu Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Lys Gly Gly Ser Pro Ser Leu Gln Ile Asn Lys
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Leu Leu Gly His Lys Asn Val Pro Arg Tyr Tyr Leu Ala Ala Pro
1               5                   10                  15

Ala

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Asp Leu Ala Val Asn Lys Val Lys Gln Val Ala His Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Lys Gly Gly Ser Pro Ser Leu Gln Ile Asn Arg
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Leu Leu Gly His Lys Asn Val Pro Arg Tyr Tyr Leu Ala Ala Pro
1               5                   10                  15

-continued

Ala

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Glu Met Ala Val Asn Lys Val Lys Gln Val Ala His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Lys Gly Gly Ser Pro Ser Leu Gln Ile Asn Lys
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Leu Leu Gly His Lys Asn Val Pro Arg Tyr Tyr Leu Ala Ala Pro
1               5                   10                  15

Ala

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Asp Leu Ala Val Asn Lys Val Lys Gln Ile Ala His Tyr
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Lys Gly Gly Ser Pro Ser Leu Gln Ile Asn Lys
1               5                   10

<210> SEQ ID NO 37
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 37

Glu Leu Leu Gly His Lys Asn Val Pro Arg Tyr Tyr Leu Ala Ala Pro
1               5                   10                  15

Ala

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Asp Leu Ala Val Asn Lys Val Lys Gln Val Gly His Tyr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Lys Gly Gly Ser Pro Ser Leu Gln Ile Asn Arg
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Leu Leu Gly His Lys Asn Val Pro Arg Tyr Tyr Leu Ala Ala Pro
1               5                   10                  15

Ala

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Asp Leu Ala Val Asn Lys Val Lys Gln Val Ala His Tyr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

Ser Lys Gly Gly Ser Pro Ser Leu Gln Ile Asn Lys
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Leu Leu Gly His Lys Asn Val Pro Arg Tyr Tyr Leu Ala Ala Pro
1               5                   10                  15

Ala

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Asp Leu Ala Val Asn Lys Val Lys Gln Val Ala Arg Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Lys Gly Gly Ser Pro Ser Leu Gln Ile Asn Lys
1               5                   10

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Leu Leu Gly His Lys Asn Val Pro Arg Tyr Tyr Leu Ala Ala Pro
1               5                   10                  15

Ala

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Asp Leu Ala Val Asn Lys Val Lys Gln Ile Ala Arg Tyr
1               5                   10

```
<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Arg Glu Ser Ser Pro Asn Phe Gln Thr Asp Thr
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Val Ala His Gln Asn Val Pro Arg Phe Phe Val Gly Ala Pro Thr
1               5                   10                  15

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Glu Met Ala Val Asn Lys Met Lys Gln Val Ala His Tyr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Cys Arg Glu Ser Ser Thr Asn Phe Gln Thr Asp Thr
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Val Ala His Gln Asn Met Pro Arg Phe Phe Val Gly Ala Pro Thr
1               5                   10                  15

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53
```

Arg Glu Met Ala Val Asn Lys Met Lys Gln Val Ala His Tyr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Arg Glu Ser Ser Pro Ser Leu Gln Thr Asp Thr
1               5                   10

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Val Ala His Gln Asn Val Pro Arg Phe Phe Val Gly Ala Pro Thr
1               5                   10                  15

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Glu Met Ala Val Asn Lys Met Lys Gln Val Ala His Tyr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Arg Glu Ser Ser Pro Asn Phe Gln Thr Asp Thr
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Pro Val Ala His Gln Asn Val Pro Arg Phe Phe Val Gly Ala Pro Thr
1               5                   10                  15

<210> SEQ ID NO 59
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 59

Arg Glu Met Ser Val Asn Lys Met Lys Gln Val Ala His Tyr
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Arg Gly Gly Ser Pro Ser Leu Gln Thr Asn Arg
1               5                   10

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Leu Leu Gly His Gln Lys Val Pro Arg Tyr Phe Leu Ala Ala Pro
1               5                   10                  15

Thr

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Glu Met Ala Val Ser Asn Met Lys Gln Ile Ala Arg Phe
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Arg Gly Gly Ser Pro Ser Leu Gln Thr Asn Arg
1               5                   10

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Leu Leu Gly His Gln Lys Val Pro Arg Tyr Phe Leu Ala Ala Pro
```

Thr

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Glu Met Ala Val Ser Asn Val Arg Glu Val Ala Arg Phe
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Arg Gly Gly Ser Pro Ser Leu Gln Thr Asn Arg
1               5                   10

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Leu Leu Gly His Gln Lys Val Pro Arg Tyr Phe Leu Ala Ala Pro
1               5                   10                  15

Thr

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Glu Met Ala Val Ser Asn Met Lys Gln Ile Ala Arg Phe
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Cys Arg Gly Gly Ser Pro Ser Leu Gln Thr Asn Arg
1               5                   10

<210> SEQ ID NO 70
<211> LENGTH: 17

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Leu Leu Gly His Gln Lys Val Pro Arg Tyr Phe Leu Ala Ala Pro
1               5                   10                  15

Thr

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Glu Met Ala Val Ser Lys Met Lys Gln Ile Ala Arg Phe
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Arg Gly Gly Ser Pro Ser Leu Gln Thr Asn Arg
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Glu Leu Leu Gly His Gln Lys Val Pro Arg Tyr Phe Leu Ala Ala Pro
1               5                   10                  15

Thr

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Glu Met Ala Val Asn Asn Met Lys Gln Ile Ala Arg Phe
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 75

Cys Arg Gly Gly Ser Pro Ser Leu Gln Thr Asn Arg
1               5                   10

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Leu Leu Gly His Gln Lys Val Pro Arg Tyr Phe Val Ala Ala Pro
1               5                   10                  15

Thr

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Glu Met Ala Val Ser Asn Met Lys Gln Ile Ala Arg Phe
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Arg Gly Gly Ser Pro Ser Leu Gln Thr Asn Arg
1               5                   10

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Leu Leu Gly His Gln Lys Val Pro Arg Phe Phe Leu Ala Ala Pro
1               5                   10                  15

Thr

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Glu Met Ala Val Ser Asn Met Lys Gln Ile Ala Arg Phe
1               5                   10
```

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Arg Gly Gly Ser Pro Ser Leu Gln Thr Asn Arg
1               5                   10

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Leu Leu Gly His Gln Lys Val Pro Arg Phe Phe Leu Ala Ala Pro
1               5                   10                  15

Thr

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Glu Met Ala Val Ser Asn Met Lys Gln Ile Ala Arg Phe
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Arg Gly Gly Ser Pro Ser Leu Gln Thr Asn Arg
1               5                   10

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Glu Leu Leu Gly His Gln Lys Val Pro Arg Tyr Phe Leu Ala Ala Pro
1               5                   10                  15

Thr

<210> SEQ ID NO 86
<211> LENGTH: 14
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 86

Arg Glu Met Ala Val Ser Lys Met Lys Glu Ile Ala Arg Phe
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Arg Gly Gly Ser Pro Ser Leu Gln Thr Asn Arg
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Leu Leu Gly His Gln Lys Val Leu Arg Tyr Phe Leu Ala Ala Pro
1               5                   10                  15

Thr

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Glu Met Ala Val Asn Asn Met Lys Gln Ile Ala Arg Tyr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Arg Gly Gly Ser Pro Ser Leu Gln Thr Asn Arg
1               5                   10

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Glu Leu Leu Gly His Gln Lys Val Leu Arg Tyr Phe Leu Ala Ala Pro
1               5                   10                  15

Thr

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Glu Met Ala Val Asn Lys Met Lys Gln Ile Ala Arg Tyr
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Cys Arg Gly Gly Ser Pro Ser Leu Gln Thr Asn Arg
1               5                   10

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Leu Leu Gly His Gln Lys Val Leu Arg Tyr Phe Leu Ala Ala Pro
1               5                   10                  15

Ala

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Glu Met Ala Val Asn Asn Met Lys Gln Ile Ala Arg Tyr
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Arg Gly Gly Ser Pro Asn Phe Gln Thr Asn Arg
1               5                   10

<210> SEQ ID NO 97

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu Leu Leu Gly His Gln Lys Val Pro Arg Tyr Phe Leu Ala Ala Pro
1               5                   10                  15
Thr

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Glu Met Ala Met Ser Lys Val Lys Gln Ile Ala His Tyr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Cys Arg Gly Gly Tyr Pro Ser Leu Gln Thr Asn Arg
1               5                   10

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Leu Leu Gly His Gln Lys Val Pro Trp Tyr Phe Leu Ala Ala Pro
1               5                   10                  15
Thr

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Glu Met Ala Met Ser Lys Val Lys Gln Ile Ala His Tyr
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 102

Cys Arg Gly Gly Ser Pro Ser Leu Gln Thr Asn Arg
1               5                   10

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Glu Leu Leu Gly His Gln Lys Val Pro Trp Tyr Phe Leu Ala Ala Pro
1               5                   10                  15

Thr

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Glu Met Ala Met Ser Lys Val Lys Gln Ile Ala His Tyr
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Arg Glu Ser Ser Pro Ser Leu Lys Thr Asp Arg
1               5                   10

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Glu Phe Leu Gly Gln Gln Asn Val Pro Arg Phe Tyr Leu Gly Ser Ser
1               5                   10                  15

Ala

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Glu Met Ala Val Asn Lys Val Arg Glu Val Ala His Tyr

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Cys Arg Glu Ser Ser Pro Ser Leu Lys Thr Asp Arg
1               5                   10

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Glu Phe Leu Gly Gln Gln Asn Val Pro Arg Phe Tyr Val Gly Ser Ser
1               5                   10                  15

Ala

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Glu Met Ala Val Asn Lys Val Arg Glu Val Ala His Tyr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Cys Arg Glu Ser Ser Pro Ser Leu Lys Thr Asp Arg
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Glu Phe Leu Gly Gln Gln Asn Val Pro Arg Phe Tyr Leu Gly Ser Ser
1               5                   10                  15

Ala

<210> SEQ ID NO 113
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Glu Met Ala Val Asn Lys Val Lys Glu Val Ala His Tyr
1               5                   10

<210> SEQ ID NO 114
<211> LENGTH: 5
<212> TYPE: PRT
<213> ORGANISM: Artificial Sequence
<220> FEATURE:
<223> OTHER INFORMATION: CDRH1 of Puma 1 and 2 directed to KEL1

<400> SEQUENCE: 114

Asp Tyr Tyr Met Lys
1               5

<210> SEQ ID NO 115
<211> LENGTH: 17
<212> TYPE: PRT
<213> ORGANISM: Artificial Sequence
<220> FEATURE:
<223> OTHER INFORMATION: CDRH2 of Puma 1 and 2 directed to KEL1

<400> SEQUENCE: 115

Asp Leu Asn Pro Asn Asn Gly Asp Thr Phe Tyr Asn Gln Lys Phe Lys
1               5                   10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: CDRH3 of Puma 1 and 2 directed to KEL1

<400> SEQUENCE: 116

Cys Ala Arg Glu Ala Gly Ser Ser Phe Gly Ser Ser Cys Asn Tyr Trp
1               5                   10                  15

Gly

<210> SEQ ID NO 117
<211> LENGTH: 11
<212> TYPE: PRT
<213> ORGANISM: Artificial Sequence
<220> FEATURE:
<223> OTHER INFORMATION: CDRL1 of Puma 1 and 2 directed to KEL1

<400> SEQUENCE: 117

Lys Ala Ser Gln Thr Val Ser Lys Asp Val Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: CDRL2 of Puma 1 and 2 directed to KEL1

<400> SEQUENCE: 118

Tyr Ala Ser Asn Arg Tyr Thr
1               5
```

<210> SEQ ID NO 119
<211> LENGTH: 6
<212> TYPE: PRT
<213> ORGANISM: Artificial Sequence
<220> FEATURE:
<223> OTHER INFORMATION: CDRL3 of Puma 1 and 2 directed to KEL1

<400> SEQUENCE: 119

Gln Gln Asp Tyr Ser Ser
1               5

<210> SEQ ID NO 120
<211> LENGTH: 5
<212> TYPE: PRT
<213> ORGANISM: Artificial Sequence
<220> FEATURE:
<223> OTHER INFORMATION: CDRH1 of Puma 3

<400> SEQUENCE: 120

Ser Tyr Gly Val Tyr
1               5

<210> SEQ ID NO 121
<211> LENGTH: 16
<212> TYPE: PRT
<213> ORGANISM: Artificial Sequence
<220> FEATURE:
<223> OTHER INFORMATION: CDRH2 of Puma 3

<400> SEQUENCE: 121

Ile Ile Trp Gly Asp Gly Ser Thr Asn Tyr Gln Ser Val Leu Arg Ser
1               5                   10                  15

<210> SEQ ID NO 122
<211> LENGTH: 7
<212> TYPE: PRT
<213> ORGANISM: Artificial Sequence
<220> FEATURE:
<223> OTHER INFORMATION: CDRH3 of Puma 3

<400> SEQUENCE: 122

Arg Gly Asp Tyr Asp Val Ala
1               5

<210> SEQ ID NO 123
<211> LENGTH: 15
<212> TYPE: PRT
<213> ORGANISM: Artificial Sequence
<220> FEATURE:
<223> OTHER INFORMATION: CDRL1 of Puma 3 antibody

<400> SEQUENCE: 123

Lys Ala Ser Gln Thr Val Ser Glu Val Gly Thr Ser Leu Met His
1               5                   10                  15

<210> SEQ ID NO 124
<211> LENGTH: 7
<212> TYPE: PRT
<213> ORGANISM: Artificial Sequence
<220> FEATURE:
<223> OTHER INFORMATION: CDRL2 of Puma 3 antibody

<400> SEQUENCE: 124

Arg Thr Ser Asn Leu Glu Ala
1               5

<210> SEQ ID NO 125
<211> LENGTH: 5
<212> TYPE: PRT
<213> ORGANISM: Artificial Sequence
<220> FEATURE:
<223> OTHER INFORMATION: CDRH1 of PUMA 4 antibody

<400> SEQUENCE: 125

Asn Tyr Trp Met Asn
1               5

<210> SEQ ID NO 126
<211> LENGTH: 19
<212> TYPE: PRT
<213> ORGANISM: Artificial Sequence
<220> FEATURE:
<223> OTHER INFORMATION: CDRH2 of PUMA 4 antibody

<400> SEQUENCE: 126

Glu Ile Arg Leu Asn Ser Asn Asn Tyr Ala Thr His Tyr Ala Glu Ser
1               5                   10                  15

Val Lys Gly

<210> SEQ ID NO 127
<211> LENGTH: 6
<212> TYPE: PRT
<213> ORGANISM: Artificial Sequence
<220> FEATURE:
<223> OTHER INFORMATION: CDRH3 of PUMA 4 antibody

<400> SEQUENCE: 127

Asn Trp Asp Phe Ala Trp
1               5

<210> SEQ ID NO 128
<211> LENGTH: 11
<212> TYPE: PRT
<213> ORGANISM: Artificial Sequence
<220> FEATURE:
<223> OTHER INFORMATION: CDRL1 of PUMA 4 antibody

<400> SEQUENCE: 128

Lys Ala Ser Gln Asp Val Ser Thr Val Val Ala
1               5                   10

<210> SEQ ID NO 129
<211> LENGTH: 7
<212> TYPE: PRT
<213> ORGANISM: Artificial Sequence
<220> FEATURE:
<223> OTHER INFORMATION: CDRL2 of PUMA 4 antibody

<400> SEQUENCE: 129

Trp Ala Ser Thr Arg His Thr
1               5

<210> SEQ ID NO 130
<211> LENGTH: 5
<212> TYPE: PRT
<213> ORGANISM: Artificial Sequence

```
<220> FEATURE:
<223> OTHER INFORMATION: CDRL3 of PUMA 4 antibody

<400> SEQUENCE: 130

Gln Gln His Tyr Thr
1               5
```